(12) United States Patent
Weingarten et al.

(10) Patent No.: US 12,319,647 B2
(45) Date of Patent: Jun. 3, 2025

(54) 2-(2,4,5-TRIMETHYLCYCLOHEX-2-EN-1-YL) ACETALDEHYDE AND DERIVATIVES AND THEIR USE AS AROMA CHEMICALS

(71) Applicant: BASF SE, Ludwigshafen am Rhein (DE)

(72) Inventors: Melanie Weingarten, Ludwigshafen am Rhein (DE); Wolfgang Siegel, Ludwigshafen am Rhein (DE); Silke Weyland, Lampertheim (DE); Ralf Pelzer, Lampertheim (DE)

(73) Assignee: BASF SE, Ludwigshafen am Rhein (DE)

( * ) Notice: Subject to any disclaimer, the term of this patent is extended or adjusted under 35 U.S.C. 154(b) by 661 days.

(21) Appl. No.: 17/625,167

(22) PCT Filed: Jul. 8, 2020

(86) PCT No.: PCT/EP2020/069251
§ 371 (c)(1),
(2) Date: Jan. 6, 2022

(87) PCT Pub. No.: WO2021/005109
PCT Pub. Date: Jan. 14, 2021

(65) Prior Publication Data
US 2022/0274904 A1    Sep. 1, 2022

(30) Foreign Application Priority Data
Jul. 9, 2019  (EP) ..................... 19185187

(51) Int. Cl.
| | |
|---|---|
| *C07C 43/162* | (2006.01) |
| *A61K 8/33* | (2006.01) |
| *A61Q 19/10* | (2006.01) |
| *C07C 33/14* | (2006.01) |
| *C07C 43/188* | (2006.01) |
| *C07C 43/303* | (2006.01) |
| *C07C 69/145* | (2006.01) |
| *C11D 3/20* | (2006.01) |
| *C11D 3/50* | (2006.01) |

(52) U.S. Cl.
CPC ............. *C07C 43/162* (2013.01); *A61K 8/33* (2013.01); *A61Q 19/10* (2013.01); *C07C 33/14* (2013.01); *C07C 43/188* (2013.01); *C07C 43/303* (2013.01); *C07C 69/145* (2013.01); *C11D 3/2068* (2013.01); *C11D 3/2072* (2013.01); *C11D 3/2093* (2013.01); *C11D 3/50* (2013.01)

(58) Field of Classification Search
CPC .......... A61Q 5/02; A61Q 19/00; A61Q 19/10; A61Q 13/00; A61K 8/33; A61K 8/44; C11B 9/0034; C11D 3/2068; C11D 3/2072; C11D 3/50; C11D 3/2093; C07C 43/303; C07C 43/162; C07C 43/188; C07C 33/14; C07C 69/145; C07C 2601/16

USPC ........................................... 512/27, 26, 25, 1
See application file for complete search history.

(56) References Cited

U.S. PATENT DOCUMENTS

| | | | |
|---|---|---|---|
| 5,268,356 A | 12/1993 | Decorzant et al. | |
| 2021/0127719 A1* | 5/2021 | Kiefl | A23L 5/27 |

FOREIGN PATENT DOCUMENTS

| | | |
|---|---|---|
| DE | 2659149 A1 | 7/1978 |
| EP | 0071787 A2 | 2/1983 |

OTHER PUBLICATIONS

International Search Report and Written Opinion received for PCT Patent Application No. PCT/EP20/069251, mailed on Sep. 30, 2020, 11 pages.
Maurer et al., "156. New Irone-Related Constituents from the Essential Oil of *Iris germanica* L." Helv. Chim. Acta 1989, vol. 72 No. 6, pp. 1400-1415.
Monnier-Benoit et al., "Synthesis of, 2,4-dimethyl-cyclohex-3-ene carboxaldehyde derivatives with olfactory properties", Comptes Rendus—Chimie, vol. 10, No. 3, 2007, pp. 259-267.
Ohtsuka, Y., et al., "Synthesis of (+)- and (−)-cis-a-Irones" Chem. Pharm Bull. 1991, vol. 39 Issue 10, pp. 2540-2544.
Schulte-Elte et al., "Diastereoselektivitaet Der Geruchswahrnehmung Von Alkoholen Der Iononreihe//Diastereoselective Odor Perception of Alcohols in the Ionone Series", Helvetica Chimica Acta, vol. 68, 1985, pp. 1961-1985.

* cited by examiner

*Primary Examiner* — Jessica Whiteley
(74) *Attorney, Agent, or Firm* — Faegre Drinker Biddle & Reath LLP

(57) ABSTRACT

The present invention relates to 2-(2,4,5-trimethylcyclohex-2-en-1-yl)acetaldehyde and derivatives thereof, to a process for preparing said compounds, to the use of 2-(2,4,5-trimethylcyclohex-2-en-1-yl)acetaldehyde or a specific derivative thereof or of mixtures of said compounds or of a stereoisomer thereof or of a mixture of two or more stereoisomers thereof as aroma chemicals; to the use of 2-(2,4,5-trimethylcyclohex-2-en-1-yl)acetaldehyde or a specific derivative thereof for modifying the scent character of a fragranced composition; to compositions containing 2-(2,4,5-trimethylcyclohex-2-en-1-yl)acetaldehyde or a specific derivative thereof or a mixture of said compounds or a stereoisomer thereof or a mixture of two or more stereoisomers thereof; and to a method of preparing a fragranced composition or for modifying the scent character of a fragranced composition, comprising incorporating 2-(2,4,5-trimethylcyclohex-2-en-1-yl)-acetaldehyde or a specific derivative thereof or a mixture of said compounds or a stereoisomer thereof or a mixture of two or more stereoisomers thereof into said composition.

17 Claims, No Drawings

2-(2,4,5-TRIMETHYLCYCLOHEX-2-EN-1-YL) ACETALDEHYDE AND DERIVATIVES AND THEIR USE AS AROMA CHEMICALS

CROSS-REFERENCE TO RELATED APPLICATIONS

This application is a national stage application (under 35 U.S.C. § 371) of PCT/EP2020/069251, filed Jul. 8, 2020, which claims benefit of European Application No. 19185187.2, filed Jul. 9, 2019, both of which are incorporated herein by reference in their entirety.

The present invention relates to 2-(2,4,5-trimethylcyclohex-2-en-1-yl)acetaldehyde and derivatives thereof, to a process for preparing said compounds, to the use of 2-(2,4,5-trimethylcyclohex-2-en-1-yl)acetaldehyde or a specific derivative thereof or of mixtures of said compounds or of a stereoisomer thereof or of a mixture of two or more stereoisomers thereof as aroma chemicals, in particular as fragrances; to the use of 2-(2,4,5-trimethylcyclohex-2-en-1-yl) acetaldehyde or a specific derivative thereof for modifying the scent character of a fragranced composition; to compositions containing 2-(2,4,5-trimethylcyclohex-2-en-1-yl)acetaldehyde or a specific derivative thereof or a mixture of said compounds or a stereoisomer thereof or a mixture of two or more stereoisomers thereof; and to a method of preparing a fragranced composition or for modifying the scent character of a fragranced composition, comprising incorporating 2-(2,4,5-trimethylcyclohex-2-en-1-yl)acetaldehyde or a specific derivative thereof or a mixture of said compounds or a stereoisomer thereof or a mixture of two or more stereoisomers thereof into said composition.

TECHNICAL BACKGROUND

Aroma chemicals, especially fragrances, are of great interest especially in the field of cosmetics and cleaning and laundry compositions. Fragrances of natural origin are mostly expensive, often limited in their available amount and, on account of fluctuations in environmental conditions, are also subject to variations in their content, purity etc. To circumvent these undesirable factors, it is therefore of great interest to create synthetic substances which have organoleptic properties that resemble more expensive natural fragrances or which have novel and interesting organoleptic profiles.

Despite a large number of already existing synthetic aroma chemicals (fragrances and flavorings), there is a constant need for new components in order to be able to satisfy the multitude of properties desired for extremely diverse areas of application. These include, firstly, the organoleptic properties, i.e. the compounds should have advantageous odiferous (olfactory) or gustatory properties. Furthermore, aroma chemicals should also have additional positive secondary properties, such as e.g. an efficient preparation method, the possibility of providing better sensory profiles as a result of synergistic effects with other fragrances, a higher stability under certain application conditions, a higher extendability, a better substantivity, etc.

However, since even small changes in chemical structure bring about massive changes in the sensory properties such as odor and also taste, the targeted search for substances with certain sensory properties such as a certain odor is extremely difficult. The search for new fragrances and flavorings is therefore in most cases difficult and laborious without knowing whether a substance with the desired odor and/or taste will even actually be found.

Ohtsuka et al., Chem. Pharm. Bull. (1991), 39(10), pp. 2540-2544, describe the preparation of 2-[(1R,5S)-2,5,6,6-tetramethylcyclohex-2-en-1-yl]acetaldehyde and 2-[(1S,5R)-2,5,6,6-tetramethylcyclohex-2-en-1-yl]acetaldehyde. Ohtsuka et al. further mention that these compounds have a characteristic aroma.

Maurer et al., Helv. Chim. Acta (1989), 72(6), pp. 1400-1415, describe the isolation and olfactory properties of 2-[(1R,5S)-2,5,6,6-tetramethylcyclohex-2-en-1-yl]acetaldehyde.

Monnier-Benoit et al., Comptes Rendus Chimie (2007), 10(23), pp. 259-267, describe the preparation and olfactory properties of 2-(2,4-dimethylcyclohex-3-en-1-yl)acetaldehyde.

It was the object of the present invention to provide new aroma chemicals. More specifically, it was the object of the present invention to prepare new aroma chemicals having pleasant organoleptic properties from malodorous 2,5,6-trimethylcyclohex-2-en1-one. Furthermore, odor-intensive substances are sought, which can be used as aroma compositions. Besides, these substances should be combinable with other aroma chemicals, allowing the creation of novel advantageous sensory profiles. In addition, the process for the preparation of these new aroma chemicals should be easy and efficient to allow their fast, economic and environmentally friendly manufacturing.

These and further objects are achieved by the compound of formulae (I), (II), (III) and (IV) or mixtures thereof or stereoisomers thereof, as shown below.

SUMMARY OF THE INVENTION

The invention relates to a compound of the general formula (I)

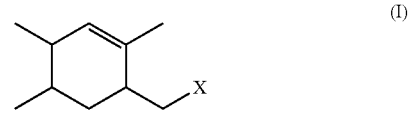

wherein
X represents a group of the formulae $X_1$ to $X_4$

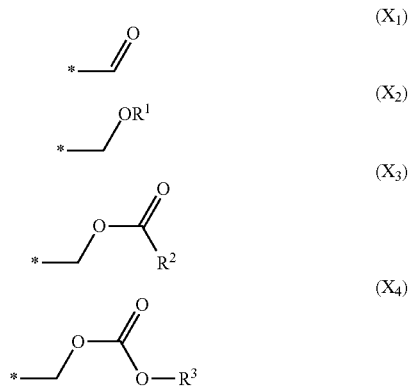

wherein the asterisk denotes the point of attachment to the rest of the molecule, and
$R^1$ and $R^2$ are, independently of each other, selected from hydrogen, methyl and ethyl, and
$R^3$ is selected from hydrogen, methyl, ethyl and phenyl, a stereoisomer thereof or a mixture of stereoisomers thereof or a mixture of different compounds (I).

Another aspect of the present invention relates to a compound of the general formula (II)

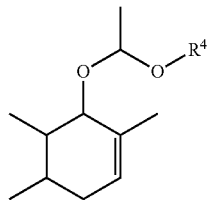

(II)

wherein
R⁴ is $C_2$-$C_4$-alkyl or a group *—[Z—O]$_n$—CH=CH$_2$, wherein the asterisk denotes the point of attachment to the oxygen atom, Z is $C_2$-$C_4$-alkylene and n is 0, 1, 2, 3, 4 or 5,
a stereoisomer thereof or a mixture of stereoisomers thereof.

Another aspect of the invention relates to a compound of the general formula (III)

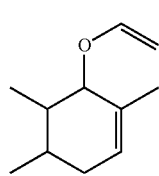

(III)

a stereoisomer thereof or a mixture of stereoisomers thereof.

Yet another aspect of the invention relates to a process for preparing a compound of the general formula (I), or a mixture of two or more different compounds of the general formula (I) or a stereoisomer of a compound (I) or a mixture of two or more stereoisomers of a compound (I) or a mixture of two or more stereoisomers of two or more different compounds (I), which process comprises:
(i) providing 2,5,6-trimethylcyclohex-2-en-1-ol (IV),

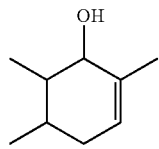

(IV)

(ii) reacting the 2,5,6-trimethylcyclohex-2-en-1-ol (IV) provided in step (i) with an vinylether of the general formula (V)

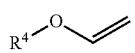

(V)

wherein
R⁴ is $C_2$-$C_4$-alkyl, or is a group *—[Z—O]$_n$—CH=CH$_2$, wherein the asterisk denotes the point of attachment to the oxygen atom, Z is $C_2$-$C_4$-alkylene and n is 0, 1, 2, 3, 4 or 5, in the presence of one or more than one catalyst,
to yield a compound of the general formula (I), wherein X represents the group $X_1$,
and optionally one or two of the following steps:
(iii) subjecting the compound obtained in step (ii) to a reduction reaction of the carbonyl group to a hydroxyl group, to obtain a compound of the general formula (I), wherein X represents a group $X_2$ where R¹ is hydrogen,
(iv.a) subjecting the compound obtained in step (iii) to an etherification reaction to obtain a compound of the general formula (I), wherein X represents a group $X_2$ where R¹ is methyl or ethyl,
or
(iv.b) subjecting the compound obtained in step (iii) to an esterification reaction to obtain a compound of the general formula (I), wherein X represents a group $X_3$,
or
(iv.c) reacting the compound obtained in step (iii) with a carbonate ($R_3$—O)$_2$—(C=O), wherein R³ is selected from hydrogen, methyl, ethyl and phenyl, where at least one of R³ is different from hydrogen, in the presence of a catalyst or a reagent $R_3$—O—C=O—Y¹, wherein R³ is selected from hydrogen, methyl, ethyl and phenyl and Y¹ represents a leaving group, selected from —O-(tert.-butoxycarbonyl) and Cl, in the presence of a catalyst or a base,
to obtain a compound of the general formula (I), wherein X represents a group $X_4$.

Another aspect of the invention relates to the use of a compound of formula (I), (II), (III) or (IV) or of a mixture of two or more different compounds of the general formulae (I), (II), (III) and/or (IV), or of a stereoisomer thereof or of a mixture of two or more stereoisomers thereof as an aroma chemical.

Another aspect of the invention relates to the use of a compound of formula (I), (II), (III) or (IV) or of a mixture of two or more different compounds of the general formulae (I), (II), (III) and/or (IV), or of a stereoisomer thereof or of a mixture of two or more stereoisomers thereof for modifying the scent character of a fragranced composition.

Yet another aspect of the invention relates to a composition comprising a compound of formula (I), (II), (III) or (IV) or a mixture of two or more different compounds of the general formulae (I), (II), (III) and/or (IV), or of a stereoisomer thereof or of a mixture of two or more stereoisomers thereof, and at least one further component selected from the group consisting of aroma chemicals, non-aroma chemical carriers, anti-oxidants and deodorant-active agents.

The invention also relates to a method for preparing a fragranced composition, in particular a fragranced ready-to-use composition, or for modifying the scent character of a fragranced composition, comprising incorporating a compound of formula (I), (II), (III) or (IV) or a mixture of two or more different compounds of the general formulae (I), (II), (III) and/or (IV), or a stereoisomer thereof or a mixture of two or more stereoisomers thereof into said composition, in particular into a ready-to-use composition.

The compounds of formulae (I), (II), (III) and (IV) as well as mixtures of two or more different compounds of the general formulae (I), (II), (III) and/or (IV), their stereoisomers and the mixtures of their stereoisomers possess advantageous organoleptic properties, in particular a pleasant odor. Therefore, they can be favorably used as an aroma chemical for example in perfume compositions, body care compositions (including cosmetic compositions), products for oral and dental hygiene, hygiene articles, cleaning compositions (including dishwashing compositions), textile detergent compositions, compositions for scent dispensers, foods, food supplements, pharmaceutical compositions and crop protection compositions.

By virtue of their physical properties, the compounds of formulae (I), (II), (III) and (IV) as well as mixtures of two or more different compounds of the general formulae (I), (II), (III) and/or (IV), their stereoisomers and the mixtures of their stereoisomers have particularly good, virtually universal solvent properties for and in aroma chemicals and other customary ingredients in compositions such as, in particular, fragrance compositions. Therefore, the compounds of formulae (I), (II), (III) and (IV) as well as mixtures of two or more different compounds of the general formulae (I), (II), (III) and/or (IV), their stereoisomers and the mixtures of their stereoisomers are favorably combinable with aroma chemicals, allowing, in particular, the creation of aroma compositions, in particular fragrance compositions, having novel advantageous sensory profiles.

Furthermore, the compounds of formulae (I), (II), (III) and (IV) as well as mixtures of two or more different compounds of the general formulae (I), (II), (III) and/or (IV), their stereoisomers and the mixtures of their stereoisomers can be produced in good yields and purities by a simple and economic synthesis, starting from readily available malodorous 2,5,6-trimethylcyclohex-2-en-1-one. Thus, the compounds of formulae (I), (II), (III) and (IV) as well as mixtures of two or more different compounds of the general formulae (I), (II), (III) and/or (IV), their stereoisomers and the mixtures of their stereoisomers can be produced in large scales in a simple and cost-efficient manner.

DETAILED DESCRIPTION OF THE INVENTION

Definitions

In the context of the present invention, the term "$C_2$-$C_4$-alkyl" as used herein refers to a linear or branched saturated aliphatic hydrocarbon radical having 2 to 4 carbon atoms. $C_2$-$C_4$-Alkyl is ethyl, propyl, isopropyl, n-butyl, 1-methylpropyl (sec-butyl), 2-methylpropyl (isobutyl) or 1,1-dimethylethyl (tert-butyl).

In the context of the present invention, the term "$C_2$-$C_4$-alkylene" as used herein refers to a linear or branched divalent alkanediyl radical having 2 to 4 carbon atoms. $C_2$-$C_2$-Alkylene is for example 1,2-ethylene, 1,1-ethylene, 1,3-propylene, 1,2-propylene, 1,4-butylene, 1,3-butylene, 1,2-butylene or 2,3-butylene.

Depending on the isomeric purity of the starting materials and method of manufacturing, e.g. the applied reaction conditions and applied workup/purification procedures, the compounds of the formula (I) can be present in the form of the pure stereoisomers or in the form of stereoisomer mixtures.

Accordingly, the present invention relates to the single pure stereoisomers of the compounds of the general formula (I) as well as to mixtures of two or more stereoisomers thereof.

The term "stereoisomers" encompasses optical isomers, such as enantiomers or diastereomers, the latter existing due to more than one stereogenic center in the molecule. The compounds of the formula (I) have 3 stereogenic centers, i.e. the carbon-atoms in the 1-, 4- and 5-position of the cyclohexene ring (the 1-position being that to which the $CH_2$—X group is bound). The invention provides both the pure enantiomers or diastereomers of the compounds (I) and mixtures thereof and the use according to the invention of the pure enantiomers or pure diastereomers of the compounds (I) or mixtures thereof.

In terms of the present invention, the term "pure enantiomer" has to be understood as a non-racemic mixture of a specific compound, where the desired enantiomer is present in an enantiomeric excess of >90% ee.

In terms of the present invention, the term "pure diastereomer" has to be understood as a mixture of the diastereomers of a specific compound, where the desired diastereomer is present in an amount of >90%, based on the total amount of diastereomers of said compound.

In the present context, the term "compound (I)" or "compound of formula (I)", when not defined as a specific stereoisomer or a specific mixture of stereoisomers, refers to the form of the compound as it is obtained in a non-stereoselective method used for its production. The term is however also used if it is not necessary or not possible to specify in more detail the stereochemistry of the compound (I). The same applies to compounds (II), (III) and (IV) when not defined as a specific stereoisomer or a specific mixture of stereoisomers.

If in the following the compounds of formula (I), (II), (III) or (IV) are defined to be a specific, defined compound (and not to be a mixture of different compounds), this means that the compound contains less than 5% by weight, preferably less than 3% by weight and in particular preferably less than 1% by weight of other compounds (I), (II), (III) and/or (IV), relative to the overall weight of the specific, defined compound and the optionally present other compound(s) (I), (II), (III) and/or (IV).

In mixtures containing different compounds (I), these can differ in the definition of the radical X. If X is $X_2$, $X_3$ or $X_4$, different compounds (I) can additionally or alternatively differ in the meaning of $R^1$, $R^2$ and/or $R^3$. Preferably, the compounds in the mixture differ only in the definition of X, or, in case that X is $X_2$, alternatively or additionally in the definition of $R^1$. Due to the preparation method via which compounds (I) in which X is $X_2$, where $R^1$ is not H, $X_3$ or $X_4$ are prepared from compounds (I) wherein X is $X_2$, wherein $R^1$ is H, such compounds may contain compounds (I) in which X is $X_2$ wherein $R^1$ is H if the reaction is not complete and/or if no isolation/purification step is carried out or not to a sufficient extent. In such mixtures, compounds (I) in which X is $X_2$ wherein $R^1$ is H are generally contained in only minor amounts, such as at most 10% by weight, preferably at most 5% by weight, in particular at most 2% by weight, based on the total weight of all compounds (I) present in the mixture.

In mixtures containing different compounds (II), these differ in the definition of the radical $R^4$.

In mixtures containing two or more compounds (I), (II), (III) and/or (IV), these contain two or more different compounds selected from the group consisting of the various compounds (I), the various compounds (II), compound (III) and compound (IV).

Embodiments

The remarks made below concerning preferred definitions of the variables further are valid on their own as well as preferably in combination with each other concerning the compounds of formulae (I), (II), (III) and (IV), as defined herein, where applicable, as well as concerning the compositions as defined herein.

Preferably, X represents a group $X_1$, $X_2$ or $X_3$, more preferably a group $X_1$ or $X_2$.

In particular, X represents a group $X_1$.

$R^1$ is hydrogen, methyl or ethyl. Specifically, $R^1$ is hydrogen or methyl.

Preferably, $R^2$ is methyl or ethyl, specifically methyl.

Preferably, $R^3$ is methyl, ethyl or phenyl, in particular methyl or ethyl.

A preferred embodiment of the present invention relates to compounds of the general formula (I)

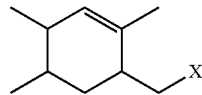
(I)

wherein
X represents a group of the formulae $X_1$ to $X_4$

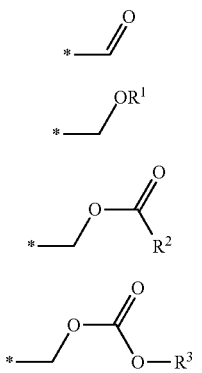

wherein the asterisk denotes the point of attachment to the rest of the molecule, and
$R^1$ is hydrogen methyl or ethyl, in particular hydrogen or methyl,
$R^2$ is methyl or ethyl, and
$R^3$ is methyl, ethyl or phenyl, in particular methyl or ethyl,
a stereoisomer thereof, a mixture of stereoisomers thereof or a mixture of different compounds (I).

Examples of such preferred compounds I are
2-(2,4,5-trimethylcyclohex-2-en-1-yl)acetaldehyde,
2-(2,4,5-trimethylcyclohex-2-en-1-yl)ethanol,
6-(2-methoxyethyl)-1,3,4-trimethyl-cyclohexene,
6-(2-ethoxyethyl)-1,3,4-trimethyl-cyclohexene,
2-(2,4,5-trimethylcyclohex-2-en-1-yl)ethyl acetate,
2-(2,4,5-trimethylcyclohex-2-en-1-yl)ethyl propanoate,
methyl 2-(2,4,5-trimethylcyclohex-2-en-1-yl)ethyl carbonate,
ethyl 2-(2,4,5-trimethylcyclohex-2-en-1-yl)ethyl carbonate,
a mixture thereof, a stereoisomer thereof or a mixture of stereoisomers thereof.

A more preferred embodiment of the present invention relates to compounds of the general formula (I)

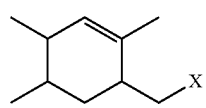
(I)

wherein
X represents a group of the formulae $X_1$ to $X_3$

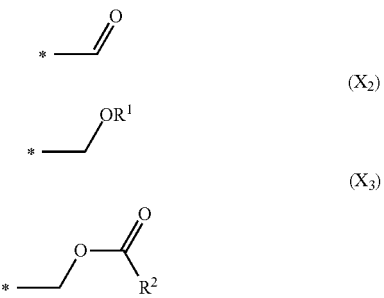

wherein the asterisk denotes the point of attachment to the rest of the molecule, and
$R^1$ is hydrogen, methyl or ethyl, in particular hydrogen or methyl,
$R^2$ is methyl or ethyl, in particular methyl,
a mixture thereof, a stereoisomer thereof or a mixture of stereoisomers thereof.

Examples of such more preferred compounds I are
2-(2,4,5-trimethylcyclohex-2-en-1-yl)acetaldehyde,
2-(2,4,5-trimethylcyclohex-2-en-1-yl)ethanol,
6-(2-methoxyethyl)-1,3,4-trimethyl-cyclohexene,
6-(2-ethoxyethyl)-1,3,4-trimethyl-cyclohexene,
2-(2,4,5-trimethylcyclohex-2-en-1-yl)ethyl acetate,
2-(2,4,5-trimethylcyclohex-2-en-1-yl)ethyl propanoate.

A particular embodiment of the present invention relates to compounds of the general formula (I)

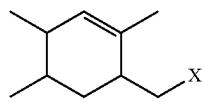
(I)

wherein
X represents a group of the formulae $X_1$ to $X_2$

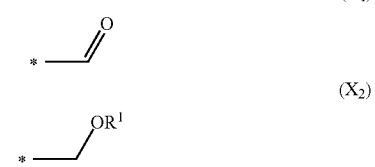

wherein the asterisk denotes the point of attachment to the rest of the molecule, and
$R^1$ is hydrogen methyl or ethyl, in particular hydrogen or methyl,
a mixture thereof, a stereoisomer thereof or a mixture of stereoisomers thereof.

Examples of such particular compounds I are
2-(2,4,5-trimethylcyclohex-2-en-1-yl)acetaldehyde,
2-(2,4,5-trimethylcyclohex-2-en-1-yl)ethanol,
6-(2-methoxyethyl)-1,3,4-trimethyl-cyclohexene,
6-(2-ethoxyethyl)-1,3,4-trimethyl-cyclohexene.

Depending on the choice and isomeric purity of the starting materials as well as the method of manufacturing, the compound (I) or the mixtures of compounds (I), as described herein, may predominantly be present in the form of a stereoisomer or mixtures of two or more stereoisomers of the general formula (I-R)

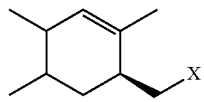

(I-R)

wherein the radical X, as well as the radicals $R^1$, $R^2$ and $R^3$, if present, have one of the meanings given above.

Alternatively, the compounds (I) or the mixtures of compounds (I), as described herein, may predominantly be present in the form of a stereoisomer or mixtures of two or more stereoisomers of the general formula (I-S)

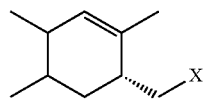

(I-S)

wherein the radical X, as well as the radicals $R^1$, $R^2$ and $R^3$, if present, have one of the meanings given above.

The term "predominantly" as used in connection with the stereoisomers of the general formula (I-R) or (I-S) means that at least 70% by weight, preferably at least 80% by weight, more preferably at least 90% by weight, even more preferably at least 95% by weight, in particular at least 98% by weight of the compounds (I), are present in the form of its stereoisomers (I-R) or (I-S).

A particular embodiment of the present invention relates to a compound of the formula (I.a)

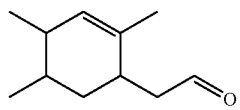

(I.a)

a stereoisomer thereof or a mixture of stereoisomers thereof.

In a specific embodiment of the present invention, the compound I.a, as described herein, is predominantly present in the form of a stereoisomer or mixtures of two or more stereoisomers of the general formula (I.a-R)

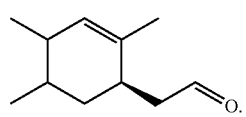

(I.a-R)

Specific compounds of the formulae (I.a-R) are
2-[(1R,4R,5R)-2,4,5-trimethylcyclohex-2-en-1-yl]acetaldehyde,
2-[(1R,4R,5S)-2,4,5-trimethylcyclohex-2-en-1-yl]acetaldehyde,
2-[(1R,4S,5R)-2,4,5-trimethylcyclohex-2-en-1-yl]acetaldehyde,
2-[(1R,4S,5S)-2,4,5-trimethylcyclohex-2-en-1-yl]acetaldehyde,
or a mixture thereof.

In an alternative specific embodiment of the present invention, the compound I.a, as described herein, is predominantly present in the form of a stereoisomer or mixtures of two or more stereoisomers of the general formula (I.a-S)

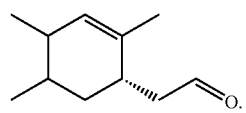

(I.a-S)

Specific compounds of the formulae (I.a-S) are
2-[(1S,4R,5R)-2,4,5-trimethylcyclohex-2-en-1-yl]acetaldehyde,
2-[(1S,4R,5S)-2,4,5-trimethylcyclohex-2-en-1-yl]acetaldehyde,
2-[(1S,4S,5R)-2,4,5-trimethylcyclohex-2-en-1-yl]acetaldehyde,
2-[(1S,4S,5S)-2,4,5-trimethylcyclohex-2-en-1-yl]acetaldehyde,
or a mixture thereof.

The term "predominantly" as used in connection with the stereoisomers of the general formula (I.a-R) or (I.a-S) means, that at least 70% by weight, preferably at least 80% by weight, more preferably at least 90% by weight, even more preferably at least 95% by weight, in particular at least 98% by weight of the compounds (I.a), are present in the form of its stereoisomers (I.a-R) or (I.s-S).

Similar to the compounds of the general formula (I), also the compounds of the general formula (II) can be present in the form of the pure stereoisomers or in the form of stereoisomer mixtures, depending on the isomeric purity of the starting materials and method of manufacturing, e.g. the applied reaction conditions and applied workup/purification procedures.

Accordingly, the present invention relates to the single pure stereoisomers of the compounds of the general formula (II) as well as to mixtures of two or more stereoisomers thereof.

The compounds of the formula (II) have at least 3 stereogenic centers, i.e. the carbon-atoms in the 4- and 5-position of the cyclohexene ring carrying the methyl groups as well as the carbon atom at the 6-position of the cyclohexene ring which carries the acetal group. Furthermore, the radicals $R^4$ in compounds (II) may also have one or more stereogenic centers, for example if $R^4$ is 1-methylpropyl or if $R^4$ represents a group —[Z—O]$_n$—CH=CH$_2$, wherein Z is selected from branched $C_3$-$C_4$-alkylene. The invention provides both the pure enantiomers or diastereomers of the compounds (II) and mixtures thereof and the use according to the invention of the pure enantiomers or pure diastereomers of the compounds (II) or mixtures thereof.

Depending on the choice and isomeric purity of the starting materials as well as the method of manufacturing, the compound (II) or the mixtures of compounds (II), as described herein, may predominantly be present in the form of a stereoisomer or mixtures of two or more stereoisomers of the general formula (II-R) or in the form of a stereoisomer or mixtures of two or more stereoisomers of the general formula (II-S)

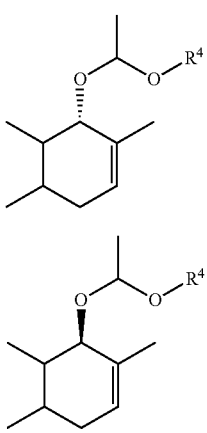

(II-R)

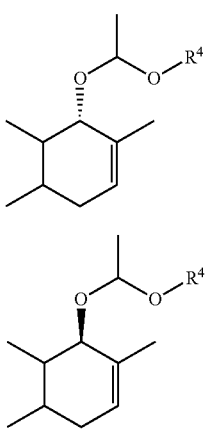

(II-S)

wherein R⁴ has one of the meanings given above or below.

The term "predominantly" as used in connection with the stereoisomers of the general formula (II-R) or (II-S) means, that at least 90% by weight, preferably at least 95% by weight, more preferably at least 98% by weight, in particular at least 99% by weight of the compounds (II), are present either in the form of its stereoisomers (II-R) or in the form of its stereoisomers (II-S).

Accordingly, in a preferred embodiment of the present invention, the compound of formula (II) is a compound of the general formulae (II-R) or (II-S)

(II-R)

(II-S)

wherein
$R^4$ is $C_2$-$C_4$-alkyl, or a group *—[Z—O]$_n$—CH=CH$_2$, wherein the asterisk denotes the point of attachment to the oxygen atom, Z is $C_2$-$C_4$-alkylene and n is 0, 1, 2, 3, 4 or 5,
a stereoisomer thereof or a mixture of stereoisomers thereof.

Preferably, in the compounds (II), (II-R) and (II-S), $R^4$ is $C_2$-$C_4$-alkyl, or a group *—[Z—O]$_n$—CH=CH$_2$, wherein the asterisk denotes the point of attachment to the oxygen atom, Z is $C_2$-$C_3$-alkylene and n is 1, 2 or 3.

More preferably, in the compounds (II), (II-R) and (II-S), $R^4$ is $C_2$-$C_4$-alkyl, or a group *—[Z—O]$_n$—CH=CH$_2$, wherein the asterisk denotes the point of attachment to the oxygen atom, Z is ethylene and n is 1, 2 or 3.

Even more preferably, in the compounds (II), (II-R) and (II-S), $R^4$ is $C_2$-$C_4$-alkyl, or 2-vinyloxyethyl.

Particularly preferably, in the compounds (II), (II-R) and (II-S), $R^4$ is $C_2$-$C_4$-alkyl, even more preferably ethyl, propyl or isobutyl, in particular ethyl or isobutyl, especially ethyl.

Preferred compounds of the general formula (II) are for example
6-(1-ethoxyethoxy)-1,4,5-trimethyl-cyclohexene,
(6R)-6-(1-ethoxyethoxy)-1,4,5-trimethyl-cyclohexene,
(6S)-6-(1-ethoxyethoxy)-1,4,5-trimethyl-cyclohexene,
6-(1-propoxyethoxy)-1,4,5-trimethyl-cyclohexene,
(6R)-6-(1-propoxyethoxy)-1,4,5-trimethyl-cyclohexene,
(6S)-6-(1-propoxyethoxy)-1,4,5-trimethyl-cyclohexene,
6-(1-isobutoxyethoxy)-1,4,5-trimethyl-cyclohexene,
(6R)-6-(1-isobutoxyethoxy)-1,4,5-trimethyl-cyclohexene,
(6S)-6-(1-isobutoxyethoxy)-1,4,5-trimethyl-cyclohexene,
1,4,5-trimethyl-6-[1-(1-methyl-2-vinyloxy-ethoxy)ethoxy]cyclohexene,
(6R)-1,4,5-trimethyl-6-[1-(1-methyl-2-vinyloxy-ethoxy)ethoxy]cyclohexene,
(6S)-1,4,5-trimethyl-6-[1-(1-methyl-2-vinyloxy-ethoxy)ethoxy]cyclohexene,
1,4,5-trimethyl-6-[1-(2-vinyloxyethoxy)ethoxy]cyclohexene,
(6R)-1,4,5-trimethyl-6-[1-(2-vinyloxyethoxy)ethoxy]cyclohexene,
(6S)-1,4,5-trimethyl-6-[1-(2-vinyloxyethoxy)ethoxy]cyclohexene,
1,4,5-trimethyl-6-[1-(2-vinyloxypropoxy)ethoxy]cyclohexene,
(6R)-1,4,5-trimethyl-6-[1-(2-vinyloxypropoxy)ethoxy]cyclohexene,
(6S)-1,4,5-trimethyl-6-[1-(2-vinyloxypropoxy)ethoxy]cyclohexene,
the stereoisomer thereof or mixtures of stereoisomers thereof.

Analogous to the compounds of the general formulae (I) and (II), also the compounds of the general formula (III) can be present in the form of the pure stereoisomers or in the form of stereoisomer mixtures, depending on the isomeric purity of the starting materials and method of manufacturing, e.g. the applied reaction conditions and applied workup/purification procedures.

Accordingly, the present invention relates to the single pure stereoisomers of the compounds of the general formula (III) as well as to mixtures of two or more stereoisomers thereof.

The compounds of the formula (III) have at least 3 stereogenic centers, i.e. the carbon-atoms in the 4- and 5-position of the cyclohexene ring carrying the methyl groups as well as the carbon atom at the 6-position of the cyclohexene ring which carries the vinyloxy group. The invention provides both the pure enantiomers or diastereomers of the compounds (III) and mixtures thereof and the use according to the invention of the pure enantiomers or pure diastereomers of the compounds (III) or mixtures thereof.

Depending on the choice and isomeric purity of the starting materials as well as the method of manufacturing, the compounds (III), as described herein, may predominantly be present in the form of a stereoisomer or mixtures of two or more stereoisomers of the general formula (III-R) or in the form of a stereoisomer or mixtures of two or more stereoisomers of the general formula (III-S)

(III-R)

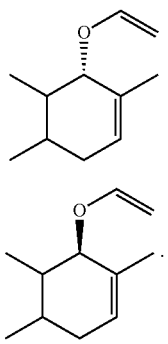

(III-S)

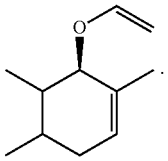

The term "predominantly" as used in connection with the stereoisomers of the general formula (III-R) or (III-S) means, that at least 90% by weight, preferably at least 95% by weight, more preferably at least 98% by weight, in particular at least 99% by weight of the compounds (III), are present either in the form of its stereoisomers (III-R) or in the form of its stereoisomers (III-S).

Accordingly, in a preferred embodiment of the present invention, the compound of formula (III) is a compound of the general formulae (III-R) or (III-S)

(III-R)

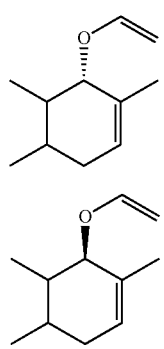

(III-S)

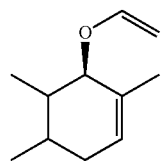

a stereoisomer thereof or a mixture of stereoisomers thereof.

Preferred compounds of the general formula (III-R) are
(4R,5R,6R)-1,4,5-trimethyl-6-vinyloxy-cyclohexene,
(4S,5R,6R)-1,4,5-trimethyl-6-vinyloxy-cyclohexene,
(4R,5S,6R)-1,4,5-trimethyl-6-vinyloxy-cyclohexene,
(4S,5S,6R)-1,4,5-trimethyl-6-vinyloxy-cyclohexene,
and mixtures thereof.

Preferred compounds of the general formula (III-S) are
(4R,5R,6S)-1,4,5-trimethyl-6-vinyloxy-cyclohexene,
(4S,5R,6S)-1,4,5-trimethyl-6-vinyloxy-cyclohexene,
(4R,5S,6S)-1,4,5-trimethyl-6-vinyloxy-cyclohexene, and
(4S,5S,6S)-1,4,5-trimethyl-6-vinyloxy-cyclohexene,
and mixtures thereof.

The compounds of the general formulae (II) and (III) are intermediates in the production process of compounds (I) as described below. Typically, in this process, the intermediates (III) are produced from the acetal precursors (II) via elimination of the alcohol $R^4$—OH. Since this elimination reaction of the acetals (II) may also occur simultaneously to the formation of the acetals (II), the intermediates (II) may comprise significant amounts of compounds (III). Furthermore, the compounds (III) may also spontaneously undergo an in situ Claisen rearrangement to the corresponding aldehyde compounds, i.e. to the compounds of the general formula (I), wherein X represents the group $X_1$.

Accordingly, the present invention relates to a mixture of compounds comprising two or three compounds selected from:
a compound of the general formula (II), a stereoisomer thereof or a mixture of stereoisomers thereof, as defined herein,
a compound of the general formula (III) a stereoisomer thereof or a mixture of stereoisomers thereof, as defined herein, and
a compound of the general formula (I), wherein X represents the group $X_1$, a stereoisomer thereof or a mixture of stereoisomers thereof, as defined herein.

A preferable embodiment of the present invention relates to mixtures of compounds comprising:
a compound of the general formula (II), a stereoisomer thereof or a mixture of stereoisomers thereof, as defined herein,
a compound of the general formula (III), a stereoisomer thereof or a mixture of stereoisomers thereof, as defined herein, and
a compound of the general formula (I), wherein X represents the group $X_1$, a stereoisomer thereof or a mixture of stereoisomers thereof, as defined herein.

An even more preferable embodiment of the present invention relates to mixtures of compounds comprising:
a compound of the general formula (III), a stereoisomer thereof or a mixture of stereoisomers thereof, as defined herein, and
a compounds of the general formula (I), wherein X represents the group $X_1$, a stereoisomer thereof or a mixture of stereoisomers thereof, as defined herein.

The total amount of the compound (II), if present, and the compounds (III) and (I), wherein X represents the group $X_1$, in the aforesaid compound mixtures is typically 70% by weight, preferably at least 80% by weight, more preferably at least 90% by weight, in particular at least 95% by weight, based on the total weight of the mixture.

In case the compounds (III) do not undergo an in situ Claisen rearrangement reaction to the corresponding aldehyde compounds, the aforesaid mixtures do not comprise significant or even no detectable amounts of compounds of the general formula (I), wherein X represents the group $X_1$.

Accordingly, a further preferred embodiment of the present invention relates to mixtures of compounds comprising:
a compound of the general formula (II), a stereoisomer thereof or a mixture of stereoisomers thereof, as defined herein, and
a compound of the general formula (III), a stereoisomer thereof or a mixture of stereoisomers thereof, as defined herein.

The total amount of the compounds (II) and (III) in the aforesaid compound mixtures is typically 70% by weight, preferably at least 80% by weight, more preferably at least 90% by weight, in particular at least 95% by weight, based on the total weight of the mixture.

In case the compounds (III) undergo immediate Claisen rearrangement reaction to the corresponding aldehyde compounds, i.e. to the compounds of the general formula (I), wherein X represents the group $X_1$, the aforesaid mixtures do not comprise significant or even no detectable amounts of a compound of the general formula (III).

Accordingly, a further preferred embodiment of the present invention relates to mixtures of compounds comprising:

a compound of the general formula (II), a stereoisomer thereof or a mixture of stereoisomers thereof, as defined herein, and a compounds of the general formula (I), wherein X represents the group X₁, a stereoisomer thereof or a mixture of stereoisomers thereof, as defined herein.

The total amount of the compounds (II) and the compounds (I), wherein X represents the group X₁, in the aforesaid compound mixtures is typically 70% by weight, preferably at least 80% by weight, more preferably at least 90% by weight, in particular at least 95% by weight, based on the total weight of the mixture.

Furthermore, according to the production process of the compounds (I), as defined below, the compounds (I) are produced from 2,5,6-trimethylcyclohex-2-en-1-one and 2,5,6-trimethylcyclohex-2-en-1-ol (IV), respectively. 2,5,6-Trimethylcyclohex-2-en-1-one is a malodorous compound, which cannot be used as an aroma chemical. The compounds (I) as well as the compounds (II), (III) and (IV), as defined herein, should therefore contain as little as possible, preferably no residual amounts of the starting material 2,5,6-trimethylcyclohex-2-en-1-one. The inventors now found that the compounds (I) as well as the compounds (II) and (III), as defined herein, can efficiently be obtained from 2,5,6-trimethylcyclohex-2-en-1-one by the process described below, without comprising detectable amounts of 2,5,6-trimethylcyclohex-2-en-1-one. Also the compounds (IV) can efficiently be obtained from 2,5,6-trimethylcyclohex-2-en-1-one by the process described below, without comprising detectable amounts or at least without comprising noticeable amounts of 2,5,6-trimethylcyclohex-2-en-1-one.

The synthesis intermediate 2,5,6-trimethylcyclohex-2-en-1-ol on the other hand smells somewhat animalic and pungent in concentrations above 1000 ppm, but at concentrations of at most 100 ppm 2,5,6-trimethylcyclohex-2-en-1-ol provides a pleasant odor profile, as outlined below.

Accordingly, a specific embodiment of the present invention relates to compounds or mixture of compounds of the general formulae (I), (II), (III) or (IV), as defined herein, comprising at most 1% by weight, preferably at most 0.5% by weight, in particular at most 0.1% by weight of 2,5,6-trimethylcyclohex-2-en-1-one, based on the total weight of the compounds or mixture of compounds. Actually, a compound of the general formula (I), (II) or (III) comprising 2,5,6-trimethylcyclohex-2-en-1-one is indeed a composition comprising the compound of the general formula (I), (II) or (III) and 2,5,6-trimethylcyclohex-2-en-1-one. In this composition, 2,5,6-trimethylcyclohex-2-en-1-one is contained in an amount of 0 to 1% by weight, preferably of 0 to 0.5% by weight, in particular 0 to 0.1% by weight, based on the total weight of the compounds (I), (II) or (III).

An even more specific embodiment of the present invention relates to compounds or mixture of compounds of the general formula (I), (II) or (III), as defined herein, comprising at most 1% by weight, preferably at most 0.5% by weight, in particular at most 0.1% by weight of 2,5,6-trimethylcyclohex-2-en-1-one and at most 5% by weight, preferably at most 3% by weight, more preferably at most 2% by weight, in particular at most 1% by weight of 2,5,6-trimethylcyclohex-2-en-1-ol, based on the total weight of the compounds or mixture of compounds. Actually, a compound of the general formula (I), (II) or (III) comprising 2,5,6-trimethylcyclohex-2-en-1-one and/or 2,5,6-trimethylcyclohex-2-en-1-ol is indeed a composition comprising the compound of the general formula (I), (II) or (III) and one or both of 2,5,6-trimethylcyclohex-2-en-1-one and 2,5,6-trimethylcyclohex-2-en-1-ol. In this composition, 2,5,6-trimethylcyclohex-2-en-1-one is contained in an amount of 0 to 1% by weight, preferably of 0 to 0.5% by weight, in particular 0 to 0.1% by weight, and 2,5,6-trimethylcyclohex-2-en-1-ol is contained in an amount of 0 to 5% by weight, preferably 0 to 3% by weight, more preferably at most 0 to 2% by weight, in particular 0 to 1% by weight, based on the total weight of the compounds (I), (II) or (III).

A further specific embodiment of the present invention relates to compounds of the general formula (IV), as defined herein, comprising at most 1% by weight, preferably at most 0.5% by weight, in particular at most 0.1% by weight, of 2,5,6-trimethylcyclohex-2-en-1-one, based on the total weight of the compounds (IV). Actually, a compound of the general formula (IV) comprising 2,5,6-trimethylcyclohex-2-en-1-one is indeed a composition comprising the compound of the formula (IV) and 2,5,6-trimethylcyclohex-2-en-1-one. In this composition, 2,5,6-trimethylcyclohex-2-en-1-one is contained in an amount of 0 to 1% by weight, preferably of 0 to 0.5% by weight, in particular 0 to 0.1% by weight, based on the total weight of the compound (IV).

An even more specific embodiment of the present invention relates to compounds or mixture of compounds of the general formula (I), (II), (III) or (IV), as defined herein, comprising no detectable amounts of 2,5,6-trimethylcyclohex-2-en-1-one.

A special embodiment of the present invention relates to compounds or mixture of compounds of the general formula (I), (II) or (III), as defined herein, comprising no detectable amounts of 2,5,6-trimethylcyclohex-2-en-1-one and 2,5,6-trimethylcyclohex-2-en-1-ol, respectively.

The present invention further relates to a process for preparing a compound of the general formula (I), or a mixture of two or more compounds of the general formula (I) or a stereoisomer thereof or a mixture of two or more stereoisomers thereof, according to any of claims 1 to 4, which process comprises:

(i) providing 2,5,6-trimethylcyclohex-2-en-1-ol (IV),

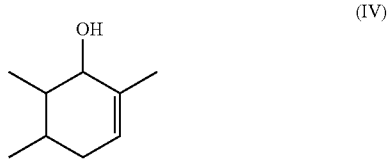

(ii) reacting the 2,5,6-trimethylcyclohex-2-en-1-ol (IV) provided in step (i) with a vinylether of the general formula (V)

wherein

R⁴ is $C_2$-$C_4$-alkyl, or is a group *—[Z—O]$_n$—CH=CH₂, wherein the asterisk denotes the point of attachment to the oxygen atom, Z is $C_2$-$C_4$-alkylene and n is 0, 1, 2, 3, 4 or 5, where R⁴ is in particular $C_2$-$C_4$-alkyl;

in the presence of one or more than one catalyst, to yield a compound of the general formula (I), wherein X represents the group X₁, and optionally one or two of the following steps:
(iii) subjecting the compound obtained in step (ii) to a reduction reaction of the carbonyl group to a hydroxyl group, to obtain a compound of the general formula (I), wherein X represents a group $X_2$ where $R^1$ is hydrogen,
(iv.a) subjecting the compound obtained in step (iii) to an etherification reaction to obtain a compound of the general formula (I), wherein X represents a group $X_2$ where $R^1$ is methyl or ethyl,
or
(iv.b) subjecting the compound obtained in step (iii) to an esterification reaction to obtain a compound of the general formula (I), wherein X represents a group $X_3$,
or
(iv.c) reacting the compound obtained in step (iii) with a carbonate $(R_3-O)_2-(C=O)$, wherein $R^3$ is selected from hydrogen methyl, ethyl and phenyl, where at least one of $R^3$ is different from hydrogen, in the presence of a catalyst; or a reagent $R_3-O-C=O-Y^1$, wherein $R^3$ is selected from hydrogen, methyl, ethyl and phenyl and $Y^1$ represents a leaving group, selected from —O-(tert.-butoxycarbonyl) and Cl, in the presence of a catalyst or a base,
to obtain a compound of the general formula (I), wherein X represents a group $X_4$.

Step (i)
In step (i) of the process of the present invention, 2,5,6-trimethylcyclohex-2-en-1-ol (IV) is provided. Typically, 2,5,6-trimethylcyclohex-2-en-1-ol can be prepared by using standard methods of organic chemistry that are known to the skilled person.

Preferably, in the process of the present invention, the 2,5,6-trimethylcyclohex-2-en-1-ol (IV) provided in step (i) is obtained by subjecting 2,5,6-trimethylcyclohex-2-en-1-one (VI)

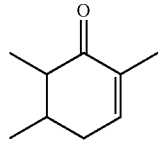

(VI)

to a selective reduction reaction of the carbonyl group to a hydroxyl group.

Generally, any method known to the skilled person for the selective reduction of the carbonyl group of α,β-unsaturated ketones to afford the corresponding α,β-unsaturated alcohols can be applied for the selective reduction of 2,5,6-trimethylcyclohex-2-en-1-one (VI) to 2,5,6-trimethylcyclohex-2-en-1-ol (IV).

For example, 2,5,6-trimethylcyclohex-2-en-1-one (VI) can be selectively reduced using heterogeneous metal catalysts, such as chromium-promoted Raney nickel in methanol, cobalt oxide or Raney cobalt, in the presence of a strong mineral base, or by using MgO or Magnesium-aluminum mixed oxide (MgO/$Al_2O_3$) in the presence of 2-propanol (Meerwein-Ponndorf-Verley type reduction), as e.g. described in the "Handbook of heterogeneous catalytic hydrogenation for organic synthesis" by S. Nishimura, chapter 5.3.5: "unsaturated ketones", pp. 198-200. Further Meerwein-Ponndorf-Verley type reductions that are suitable for the chemoselective reduction of 2,5,6-trimethylcyclohex-2-en-1-one (VI) by using organometallic reagents such as in particular diisobutylaluminum and diisopinocampheylboron derivatives, are for example described by Cha et al., Bull. Korean Chem. Soc. (2007), 28(12), pp. 2162-2190, and the references cited therein.

Alternatively, the chemoselective reduction of 2,5,6-trimethylcyclohex-2-en-1-one (VI) to 2,5,6-trimethylcyclohex-2-en-1-ol (IV) may also be performed in the presence of metal hydrides, such as $Zn(BH_4)_2$, $NaBH_4/CeCl_3$, $LiAlH_4$, Li n-BuBH$_3$ or 9-borabicyclo[3.3.1]nonane (9-BBN), as for example described by Cha et al., Bull. Korean Chem. Soc. (2007), 28(12), pp. 2162-2190, Cha et al., Bull. Korean Chem. Soc. (2011), 32(6), 1808, and Cha et al., Organic Process Research & Development (2006), 10, pp. 1032-1053, as well as the references cited therein. Suitable reduction methods by using $NaBH_4$ and $LiAlH_4$, respectively with addition of lanthanide salts are for example described by Gemal et al., J. Am. Chem. Soc. (1981), 103, pp. 5454-5459, or by Li et al., J. Org. Chem. (2007), 72, pp. 2344-2350, or in Org. Synthesis Highlights II: "Organolanthanides in Reduction and Nucleophilic Addition Methodology" by K. H. Dötz. Furthermore, 2,5,6-trimethylcyclohex-2-en-1-one (VI) can be selectively reduced to 2,5,6-trimethylcyclohex-2-en-1-ol (IV) in the presence of catalytic amounts of phosphine stabilized Cu—H complexes and stoichiometric amounts of (alkyl/aryl/alkoxy)silanes, as for example described in "Topics in Organometallic Chemistry", 2016, 58, pp. 207-220, and the references cited therein.

The chemoselective reduction of 2,5,6-trimethylcyclohex-2-en-1-one (VI) to 2,5,6-trimethylcyclohex-2-en-1-ol (IV) may also be performed enantioselective.

The enantioselective reduction of 2,5,6-trimethylcyclohex-2-en-1-one (VI) to either (1R)- or (1S)-2,5,6-trimethylcyclohex-2-en-1-ol (IV) can by way of example be performed by using chiral hydride reagents, e.g. by using lithium aluminium hydride modified with chiral alkoxide ligands such as BINOL, as for example described by Chan et al., J. Org. Chem. (1988), 53, 5584-5586, or by using chiral alkylborohydrides, as for example described by Ramachandran et al., Tetrahedron: Asymmetry (1990), 1, 433.

Furthermore, also catalytic reduction processes can be used, where a hydride donor in stoichiometric amounts is applied together with chiral transition metal catalysts (enantioselective Meerwein-Ponndorf-Verley type reduction). Suitable chiral transition metal catalysts are for example Ru, Rh, Ir or Sm complexes with chiral diamine ligands, chiral aminoalcohol ligands, chiral bisphosphine ligands or chiral bis(oxazoline) ligands. Also chiral phosphine ligands/ Cu—H complexes may be used as chiral catalysts, as for example described by Moser et al., J. Am. Chem. Soc., 2010, 132 (23), pp. 7852-7853.

Besides, the enantioselective reduction of 2,5,6-trimethylcyclohex-2-en-1-one (VI) to either (1R)- or (1S)-2,5,6-trimethylcyclohex-2-en-1-ol (IV) may also be performed enzymatically by using suitable alcoholdehydrogenases or by using microorganisms, such as specifically modified baker's yeast.

In a preferred embodiment of the present invention, the selective reduction reaction of 2,5,6-trimethylcyclohex-2-en-1-one (VI) to 2,5,6-trimethylcyclohex-2-en-1-ol (IV) is performed in the presence of metal hydrides, as defined above. Preferably, the metal hydride is selected from $NaBH_4$, $NaBH_4/CeCl_3$, $Zn(BH_4)_2$, $LiAlH_4$, Li n-BuBH$_3$ and 9-BBN.

In this preferred embodiment, the selective reduction reaction is typically carried out in an inert solvent, i.e. a solvent that does not react with the starting materials, intermediates and reagents applied in the reduction reaction or with the obtained products. Suitable solvents are for example alcohols, such as methanol, ethanol, propanol and isopropanol; aromatic and substituted aromatic hydrocarbons, such as benzene, chlorobenzene, dichlorobenzenes, toluene, xylene; and aliphatic hydrocarbons, such as pentane, hexanes, cyclohexane, heptanes, octanes, nonanes, decanes, ligroin and petrol ether, halogenated aliphatic hydrocarbons, such as dichloromethane, trichloromethane and tetrachloromethane, ethers, such as diethyl ether, dibutyl ether, THF, 1,4-dioxane, 1,2-dimethoxyethane; as well as mixtures thereof.

The metal hydride reagent is typically applied in stoichiometric amounts. However, depending on the reactivity and the number of hydride-ions (hydride equivalents) that is delivered by the hydride reagent as well as the type of solvent applied in the reduction reaction, the final amount of the added hydride reagent typically varies within a broad range. For example, whereas 0.25 to 0.35 equivalents of $LiAlH_4$ per 1 equivalent of carbonyl compound, which corresponds to 1 to 1.4 hydride equivalents per 1 equivalent of carbonyl compound, are usually enough to obtain full reduction of a ketone compound to the corresponding alcohol, 0.8 to 1.4 equivalents of $NaBH_4$ per 1 equivalent of carbonyl compound, which corresponds to 3.2 to 5.6 hydride equivalents per 1 equivalent of carbonyl compound, may be necessary to obtain the same result.

Typically, the metal hydride reagent is added in several portions, e.g. in 2, 3, 4, 5, 10, 15 or 20 portions or continuously over a time period of from 5 minutes to 5 hours, preferably over a time period of 20 minutes to 3 hours to the reaction mixture comprising 2,5,6-trimethylcyclohex-2-en-1-one (VI).

Alternatively, 2,5,6-trimethylcyclohex-2-en-1-one (VI) may be added in several portions, e.g. in 2, 3, 4, 5, 10, 15 or 20 portions or continuously over a time period of from 5 minutes to 5 hours, preferably over a time period of 20 minutes to 3 hours to the reaction mixture comprising the total amount of the metal hydride reagent.

In order to foster high selectivity, the selective reduction reaction of this preferred embodiment is typically performed at low reaction temperatures, i.e. at reaction temperatures in the range of from −20 to 20° C., preferably in the range of from −10 to 15° C., in particular in the range of from −5 to 10° C.

In a further preferred embodiment of the present invention, the selective reduction reaction of 2,5,6-trimethylcyclohex-2-en-1-one (VI) to 2,5,6-trimethylcyclohex-2-en-1-ol (IV) is performed under Meerwein-Ponndorf-Verley type conditions using organometallic reagents, preferably organo-boron and organo-aluminium reagents, in particular diisopinocampheylboron and diisobutylaluminum derivatives.

In this preferred embodiment, the selective reduction reaction is typically carried out in an inert solvent, i.e. a solvent that does not react with the starting materials, intermediates and reagents applied in the reduction reaction or with the obtained products. Suitable solvents are for example aliphatic hydrocarbons, such as pentane, hexanes, cyclohexane, heptanes, octanes, nonanes, decanes, ligroin and petrol ether; halogenated aliphatic hydrocarbons, such as dichloromethane, trichloromethane and tetrachloromethane; ethers, such as diethyl ether, dibutyl ether, THF, 1,4-dioxane, 1,2-dimethoxyethane; as well as mixtures thereof.

The organometallic reagent is typically applied in stoichiometric amounts. However, depending on the reactivity and the nature of the organometallic reagent the amount of the organometallic reagent applied in the selective reduction reaction typically varies within a broad range. Typically, the organometallic reagent is added in amounts of from 0.5 to 5 equivalents, preferably in amounts of from 0.8 to 3 equivalents, per 1 equivalent of carbonyl compound.

The reaction temperature for the selective reduction reaction of this preferred embodiment greatly varies depending on the reactivity of the applied organometallic reagent. For example, if triethylborane is used as the organometallic reagent, the reduction of carbonyl groups can only be effected at rather high reaction temperatures, e.g. at reaction temperatures in the range of from 80 to 150° C., whereas if diisopinocampheylhalo-boranes ($Ipc_2BX$) are used as the organometallic reagent, the reduction of carbonyl groups can be performed at reaction temperatures as low as −25 to 0° C. In case of the preferably used diisopinocampheylboron and diisobutylaluminum derivatives the reaction temperatures are typically in the range of from −15 to 45° C., preferably in the range of from −5 to 35° C.

2,5,6-trimethylcyclohex-2-en-1-one (VI), which is used as the preferred starting material, can typically be purchased as a mixture of stereoisomers, i.e. a mixture of cis-2,5,6-trimethylcyclohex-2-en-1-one (5R,6R-2,5,6-trimethylcyclohex-2-en-1-one and 5S,6S-2,5,6-trimethylcyclohex-2-en-1-one, hereinafter referred to as cis-VI) and trans-2,5,6-trimethylcyclohex-2-en-1-one (5R,6S-2,5,6-trimethylcyclohex-2-en-1-one and 5S,6R-2,5,6-trimethylcyclohex-2-en-1-one, hereinafter referred to as trans-VI).

Alternatively, the ketone 2,5,6-trimethylcyclohex-2-en-1-one (VI) can be prepared by using standard methods of organic chemistry that are known to the skilled person.

Typically, 2,5,6-trimethylcyclohex-2-en-1-one (VI) is applied in the reaction of step (i) either in the form of one of its pure stereoisomers or in the form of stereoisomer mixtures.

Preferably, 2,5,6-trimethylcyclohex-2-en-1-one (VI) is applied in the form of stereoisomer mixtures.

More preferably, 2,5,6-trimethylcyclohex-2-en-1-one (VI) is applied in the reaction of step (i) in the form of mixtures of all 4 stereoisomers, wherein the ratio of the trans-VI stereoisomers to the cis-VI stereoisomers is in the range of from 55:45 to 90:10, even more preferably in the range of from 60:40 to 80:20, in particular in the range of from 65:35 to 75:25.

Furthermore, depending on the commercial source/origin or the manufacturing method, 2,5,6-trimethylcyclohex-2-en-1-one (VI) may comprise lower amounts, e.g. at most 5% by weight, preferably at most 2% by weight, in particular at most 1.5% by weight of the corresponding saturated 2,3,6-trimethylcyclohexane-1-one isomers.

Step (ii):

In step (ii) of the process of the present invention, the 2,5,6-trimethylcyclohex-2-en-1-ol (IV) provided in step (i) is reacted with a vinylether of the general formula (V)

wherein $R^4$ is $C_2$-$C_4$-alkyl, or is a group *—[Z—O]$_n$—CH=$CH_2$, wherein the asterisk denotes the point of attachment to the oxygen atom, Z is $C_2$-$C_4$-alkylene and n is 0, 1, 2, 3, 4 or 5, in the presence of one or more than one catalyst, to yield a compound of the general formula (I), wherein X represents the group $X_1$.

Preferably, the catalyst applied in step (ii) is selected from Brønsted acids and Lewis acids and mixtures thereof. More preferably, the catalyst applied in step (ii) is selected from weak to moderately strong Brønsted acids and soft to moderately hard Lewis acids.

Preferable weak to moderately strong Brønsted acids are Brønsted acids, which have a pKa value in water in the range of from 6 to 0.5, preferable in the range of from 5.2 to 1, in particular in the range of from 4.9 to 1.5. Preferable Brønsted acids are for example phosphoric acid, phosphonic acids, such as methylphosphonic acid, ethylphosphonic acid, propylphosphonic acid or phenylphosphonic acid and carboxylic acids, such as oxalic acid, chloroacetic acid, citric acid, tartaric acid, formic acid, acetic acid and propionic acid.

Suitable Lewis acids that can be applied in step (ii) are for example Fe(III)acetylacetonate, Fe(III)Cl$_3$, Yb(III)triflate, Bi(III)triflate, MgCl$_2$, Fe(II)acetylacetonate, Fe(II)acetate, Fe(II)triflate, Fe(II)Cl$_2$, Ni(II)acetylacetonate, Ni(II)acetate, Ni(II)triflate, Ni(II)Cl$_2$, Co(II)acetylacetonate, Co(II)acetate, Co(II)triflate, Co(II)Cl$_2$, Cu(II)acetylacetonate, Cu(II)acetate, Cu(II)triflate, Cu(II)Cl$_2$, Hg(II)acetylacetonate, Hg(II)acetate, Hg(II)triflate, Hg(II)Cl$_2$, Pd(II)acetylacetonate, Pd(II)acetate, Pd(II)triflate, Pd(II)Cl$_2$, e.g. Pd(II)Cl$_2$(MeCN)$_2$, Pt(II)acetylacetonate, Pt(II)acetate, Pt(II)triflate, Pt(II)Cl$_2$, Cd(II)acetylacetonate, Cd(II)acetate, Cd(II)triflate, Cd(II)Cl$_2$, Cu(I)acetate, Cu(I)triflate, Cu(I)Cl, Ag(I)acetate, Ag(I)triflate, Au(I)acetate, Au(I)triflate and Ag(I)Cl.

In particular, the catalyst applied in step (ii) is selected from phosphoric acid; phosphonic acids, such as methylphosphonic acid, ethylphosphonic acid, propylphosphonic acid and phenylphosphonic acid; carboxylic acids, such as formic acid, oxalic acid, chloroacetic acid, citric acid, tartaric acid, acetic acid and propionic acid; and soft to moderately hard Lewis acids, such as Fe(III)acetylacetonate, Yb(III)triflate, Bi(III)triflate, MgCl$_2$, Fe(II)acetylacetonate, Fe(II)acetate, Fe(II)triflate, Ni(II)acetylacetonate, Ni(II)acetate, Ni(II)triflate, Co(II)acetylacetonate, Co(II)acetate, Co(II)triflate, Cu(II)acetylacetonate, Cu(II)acetate, Cu(II)triflate, Hg(II)acetylacetonate, Hg(II)acetate, Hg(II)triflate, Hg(II)Cl$_2$, Pd(II)acetylacetonate, Pd(II)acetate, Pd(II)triflate, Pd(II)Cl$_2$, e.g. Pd(II)Cl$_2$(MeCN)$_2$, Pt(II)acetylacetonate, Pt(II)acetate, Pt(II)triflate, Cd(II)acetylacetonate, Cd(II)acetate, Cd(II)triflate, Cu(I)acetate, Cu(I)triflate, Ag(I)acetate, Ag(I)triflate, Au(I)acetate and Au(I)triflate.

Especially, the catalyst applied in step (ii) is selected from phosphoric acid, phenylphosphonic acid, formic acid, acetic acid, propionic acid, Fe(III)acetylacetonate, Cu(II)acetate, Cu(I)acetate, Hg(II)acetate, Pd(II)acetate, Pd(II)triflate and Pd(II)Cl$_2$, e.g. Pd(II)Cl$_2$(MeCN)$_2$.

Typically, the reaction in step (ii) proceeds via the formation of two intermediate compounds, i.e. compounds of the general formulae (II) and (III), as depicted in scheme 1.

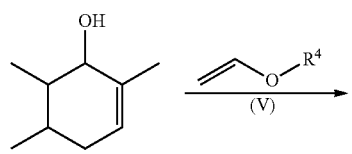

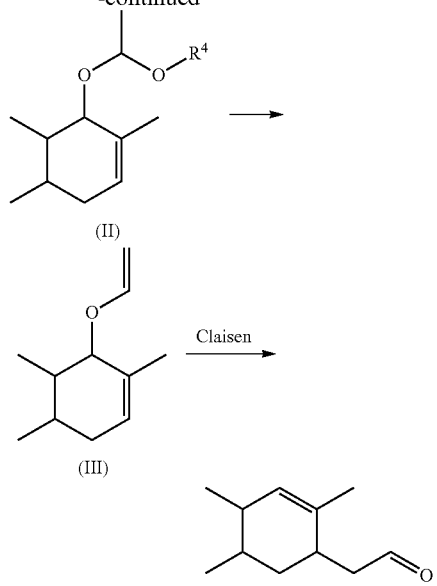

Under the reaction conditions described herein, the alcohol group of 2,5,6-trimethylcyclohex-2-en-1-ol first adds to the vinyl group of compounds (V) resulting in the formation of the acetal intermediates (II). These acetal intermediates (II) further react to the vinyl ether intermediate (III) by eliminating the alcohol $R^4$—OH. The vinyl ether intermediate (III) in turn undergoes a Claisen rearrangement to form the corresponding aldehyde compounds, i.e. the compounds of the general formula (I), wherein the group X represents the aldehyde group $X_1$.

Depending on the catalyst, the applied vinylether compound (V) and the selected reaction conditions, the reaction in step (ii) of the present invention may stop at the acetal intermediate (II) and/or the vinylether intermediate (III) (two or three step reaction) or will directly provide the desired aldehyde compounds of formula (I), wherein X represents a group $X_1$ (one step reaction).

In case of the two or three step reaction, hereinafter also referred to as the two or three step variants of step (ii), the 2,5,6-trimethylcyclohex-2-en-1-ol is first reacted with a vinylether of the general formula (V) to the first intermediate compound, i.e. the acetal of the general formula (II). The acetal intermediates (II) can be isolated, i.e. subjected to a work-up and/or purification procedure, before they are further converted to the second intermediate compound, i.e. the vinylether intermediate (III), or to the final aldehyde compounds of formula (I), wherein X represents a group $X_1$, through subsequent Claisen rearrangement. Alternatively, the obtained acetal intermediates (II) can be directly applied to the further conversion reactions. If the acetal intermediates (II) are not directly converted to the final aldehyde compound (I) but first to the vinylether intermediates (III), these vinylethers (III) may also be isolated before they are subjected to the final Claisen rearrangement reaction. Alternatively, the vinylethers (III) can also be directly applied to the final Claisen rearrangement reaction, without prior work-up and/or purification procedure.

The different sub-steps of the two or three step variants of step (ii) can be performed in the presence of the same catalyst or in the presence of different catalysts. If the same catalyst is applied in the sub-steps, the course of the reaction is typically controlled via the reaction temperature, the removal of volatile reaction products, such as the alcohol $R^4$—OH, and/or the amount of the catalyst in the reaction. If different catalysts are applied in the sub-steps, the first sub-step, i.e. the formation of the acetal intermediate (II), is typically performed with a first catalyst, e.g. a Brønsted acid, and the following sub-steps are performed with a second catalyst different from the first catalyst, e.g. a Lewis acid. If a second catalyst different from the first catalyst is applied in the following sub-steps, the first catalyst can be removed via extractive work-up and/or the second catalyst is added to the reaction mixture comprising the first catalyst.

Suitable catalysts that can be applied in the two or three step variant of step (ii) are the catalysts as defined above.

The catalyst applied in the first sub-step of the two or three step variant of step (ii) is preferably selected from weak to moderately strong Brønsted acids, as defined above.

For the further conversion of the acetal intermediate (II) obtained in the first sub-step to the vinylether compounds (III), or to the desired aldehyde compounds of formula (I), wherein X represents a group $X_1$, also Lewis acids, as defined above, may be applied.

The vinylether compounds that can suitably be applied in the two or three step variant of step (ii) are preferably selected from compounds (V), wherein $R^4$ is $C_2$-$C_4$-alkyl, or a group *—[Z—O]$_n$—CH=CH$_2$, wherein the asterisk denotes the point of attachment to the oxygen atom, Z is ethylene and n is 1, 2 or 3. More preferably, the vinylether compounds are selected from compounds (V), wherein $R^4$ is $C_2$-$C_4$-alkyl or 2-vinyloxyethyl, even more preferably ethyl, propyl, isobutyl or 2-vinyloxyethyl, even more preferably ethyl, propyl or isobutyl, in particular ethyl or isobutyl, especially ethyl. In particular, the vinylether compounds are selected from compounds (V), wherein $R^4$ is $C_2$-$C_4$-alkyl, more particularly ethyl, propyl or isobutyl, even more particularly ethyl or isobutyl, especially ethyl.

In case of the one step reaction, hereinafter also referred to as the one step variant of step (ii), the 2,5,6-trimethylcyclohex-2-en-1-ol is directly converted to the desired aldehyde compounds of formula (I), wherein X represents a group $X_1$. Suitable and preferred vinylether compounds that can suitably be applied in the one step variant of step (ii) correspond to those listed above for the two or three step variant of step (ii).

Suitable catalysts that can be applied in the one step variant of step (ii) are the catalysts as defined above.

However, the reaction rate may be increased by using moderately strong Brønsted acids and/or Lewis acids. Preferably, in this one step variant of step (ii), the catalyst is selected from moderately strong Brønsted acids, such as phosphoric acid, phosphonic acids, such as methylphosphonic acid, ethylphosphonic acid, propylphosphonic acid or phenylphosphonic acid, oxalic acid, chloroacetic acid, and Lewis acids, such as Fe(III)acetylacetonate, Fe(II)acetylacetonate, Fe(II)acetate, Fe(II)triflate, Cu(II)acetylacetonate, Cu(II)acetate or Cu(II)triflate.

The amount of catalyst used in the reaction in step (ii) is typically in the range of from 0.0001 to 0.5 equivalents, preferably in the range of from 0.0005 to 0.3 equivalents, in particular in the range of from 0.001 to 0.1 equivalents based on 1 equivalent of the compound (IV).

Dependent on whether the vinylether of the general formula (V) is used as internal solvent or an external solvent is used, the ratio of the compound (IV) to the vinylether of the general formula (V) applied in the reaction in step (ii) varies within a brought range. The ratio of the compound (IV) to the vinylether of the general formula (V) applied in the reaction in step (ii) is typically in the range of from 1:1 to 1:20, preferably in the range of from 1:1.1 to 1:15, more preferably in the range of from 1:1.2 to 1:10, in particular in the range of from 1:1.5 to 1:5.

The reaction in step (ii) can be carried out in the presence of an inert solvent, as defined above, or in the absence of any external solvent. Preferably, the reaction in step (ii) is carried out in the absence of any external solvent. In these cases, the applied vinylether compound (V) acts as internal solvent.

In case of the two or three step variant of step (ii), the first sub-step, i.e. the formation of the acetal intermediates (II) is preferably performed at a reaction temperature in the range of from 10 to 100° C., in particular in the range of from 20 to 70° C. The following sub-steps, i.e. the further conversion of the acetal intermediates (II) to the vinylether intermediates (III) and/or the compound (I), wherein X represents a group $X_1$, are preferably performed at a reaction temperature in the range of from 90 to 250° C., more preferably in the range of from 100 to 220° C., in particular in the range of from 110 to 200° C.

In case of the one step variant of step (ii), the reaction in step (ii) is preferably performed at a reaction temperature in the range of from 90 to 250° C., more preferably in the range of from 110 to 240° C., in particular in the range of from 120 to 230° C.

The reaction in step (ii) can take place in the absence of or in the presence of an inert gas. The expression "inert gas", as used herein, generally means a gas, which under the prevailing reaction conditions does not enter into any reactions with the starting materials, reagents, or solvents participating in the reaction, or with the resultant products. In case the reaction in step (ii) is conducted in the presence of an inert gas, the inert gas is preferably selected from argon and nitrogen as well as mixtures thereof, in particular the inert gas is nitrogen.

The reaction in step (ii) may be carried out at atmospheric pressure or at elevated pressures. In case the reaction in step (ii) is performed at higher reaction temperatures, e.g. at a reaction temperature in the range of from 100 to 250° C., the reaction in step (ii) is preferably carried out at elevated pressures, more preferably at a pressure in the range from 1.1 to 20 bar, in particular at a pressure in the range from 1.5 to 15 bar. In case the reaction in step (ii) is performed at lower reaction temperatures, e.g. at a reaction temperature in the range of from 10 to 100° C., the reaction in step (ii) is preferably carried out at atmospheric pressure.

In a preferred embodiment, step (ii) of the process of the present invention comprises the following steps:

(ii.a) reacting the 2,5,6-trimethylcyclohex-2-en-1-ol (IV) provided in step (i) with a vinylether of the general formula (V)

(V)

wherein
$R^4$ is $C_2$-$C_4$-alkyl, or is a group *—[Z—O]$_n$—CH=CH$_2$, wherein the asterisk denotes the point of attachment to the oxygen atom, Z is $C_2$-$C_4$-alkylene and n is 0, 1, 2, 3, 4 or 5, where $R^4$ is in particular $C_2$-$C_4$-alkyl;
in the presence of a catalyst,
to obtain a first intermediate compound of the general formula (II), as defined above, (ii.b) further reacting the intermediate compound (II) obtained in step (ii.a), at temperatures of at least 150° C.

and/or in the presence of a catalyst, to obtain a second intermediate compound of the general formula (III), as defined above, (ii.c) further reacting the intermediate compound (III) obtained in step (ii.b), at temperatures of at least 150° C. and/or in the presence of a catalyst, to yield a compound of the general formula (I), wherein X represents the group $X_1$.

The catalyst applied in step (ii.a), the preferable ratios and amounts of the reactants (IV) and (V), the preferable amount of the catalyst as well as the preferable reaction conditions applied in step (ii.a) are as defined above for the first sub-step of the two or three step variant of step (ii).

Likewise, the catalysts applied in steps (ii.b) and (ii.c), the preferable amounts of the catalysts and the preferable reaction conditions applied in steps (ii.b) and (ii.c) are as defined above for the further sub-step(s) of the two or three step variant of step (ii).

The reaction of step (ii.b) can be performed at temperatures of at least 150° C., preferably at temperatures in the range of from 150 to 300° C., in particular in the range of from 150 to 260° C., alternatively or in addition to the application of a catalyst.

Likewise, the reaction of step (ii.c) can be performed at temperatures of at least 150° C., preferably at temperatures in the range of from 150 to 280° C., in particular in the range of from 155 to 250° C., alternatively or in addition to the application of a catalyst.

As already indicated above, the first intermediate compound of the general formula (II) may also react directly to the final aldehyde compound of the general formula (I), wherein X represents the group $X_1$.

Accordingly, in an alternative preferred embodiment, step (ii) of the process of the present invention comprises the following steps:

(ii.a') reacting the 2,5,6-trimethylcyclohex-2-en-1-ol (IV) provided in step (i) with a vinylether of the general formula (V)

(V)

wherein
$R^4$ is $C_2$-$C_4$-alkyl, or is a group *—[Z—O]$_n$—CH=CH$_2$, wherein the asterisk denotes the point of attachment to the oxygen atom, Z is $C_2$-$C_4$-alkylene and n is 0, 1, 2, 3, 4 or 5, where $R^4$ is in particular $C_2$-$C_4$-alkyl;
in the presence of a catalyst,
to obtain a first intermediate compound of the general formula (II), as defined above, (ii.b') further reacting the intermediate compound (II) obtained in step (ii.a),
in the presence of a catalyst,
to yield a compound of the general formula (I), wherein X represents the group $X_1$.

Also in this preferred variant of step (ii), the catalyst applied in step (ii.a'), the preferable ratios and amounts of the reactants (IV) and (V), the preferable amount of the catalyst as well as the preferable reaction conditions applied in step (ii.a') are as defined above for the first sub-step of the two or three step variant of step (ii).

Likewise, the catalysts applied in step (ii.b'), the preferable amounts of the catalysts and the preferable reaction conditions applied in step (ii.b') are as defined above for the further sub-step(s) of the two or three step variant of step (ii).

Accordingly, also in this preferred variant, the reaction of step (ii.b') can be performed at temperatures of at least 160° C., preferably at temperatures in the range of from 160 to 300° C., in particular in the range of from 165 to 260° C., alternatively or in addition to the application of a catalyst.

In another embodiment of the process of the present invention, the reaction in step (ii) is performed in a microwave heating apparatus. In this embodiment, the catalyst is preferably selected from soft Lewis acids, in particular from Cu(II)acetate, Cu(I)acetate and Fe(III)acetylacetonate. The reaction in the microwave heating apparatus is preferably conducted at a reaction temperature in the range of from 150 to 260° C., in particular in the range of from 170 to 240° C.

Step (iii)

In step (iii) of the process of the present invention, the aldehyde compound obtained in step (ii) is subjected to a selective reduction reaction of the carbonyl group to a hydroxyl group, to obtain a compound of the general formula (I), wherein X represents a group $X_2$ where $R^1$ is hydrogen.

The reduction reaction in step (iii) is typically performed in the presence of a reducing agent that is suitable for reducing aldehydes to the corresponding alcohols, without affecting non conjugated C=C double bonds. Suitable reducing agents and reaction conditions are for example described above in connection with the chemoselective reduction of 2,5,6-trimethylcyclohex-2-en-1-one (VI) to 2,5,6-trimethylcyclohex-2-en-1-ol (IV). Alternatively, the selective reduction of the aldehyde group may also be achieved by reacting the compound obtained in step (ii) with hydrogen in the presence of a transition metal catalyst, e.g. by analogy to the method described in EP 71787.

Step (iv.a)

In step (iv.a) of the process of the present invention, the compound obtained in step (iii) is subjected to an etherification reaction to obtain a compound of the general formula (I), wherein X represents a group $X_2$ where $R^1$ is methyl or ethyl. The etherification reaction can be carried out according to known procedures for this reaction type under acidic or basic conditions using methylation or ethylation agents.

Preferably, the compound obtained in step (iii) is reacted with an alkylation reagent (to be more precise a methylation or ethylation agent) selected from compounds of formula $R^{1a}$—Y, dimethylsulfate and diethylsulfate, wherein $R^{1a}$ is methyl or ethyl and Y represents a leaving group selected from halogen, such as Cl, Br or I, and sulfonates, such as tosylate, mesylate, triflate or nonaflate; in the presence of a base.

Suitable bases are typically selected from inorganic bases and organic bases.

Suitable inorganic bases that can be used in this alkylation reaction are for example alkali metal carbonates, e.g. $Li_2CO_3$, $Na_2CO_3$, $K_2CO_3$ or $Cs_2CO_3$, alkali metal hydroxides, e.g. LiOH, NaOH or KOH, and hydride donors, e.g. NaH, $LiAlH_4$, $NaBH_4$, metallic Na or metallic K. Metallic Na and metallic K are generally used in the presence of an alcohol, such as a $C_1$-$C_4$-alkanol, e.g. methanol, ethanol, propanol, isopropanol, nbutanol or tert-butanol, or a monoether of a diol, e.g. ethyleneglycolmonomethyl ether, ethyleneglycolmonoethyl ether, diethyleneglycolmonomethyl ether, or diethyleneglycolmonoethyl ether, thus converting at least a part of the alkali metal into the alkali metal alkoxide.

Suitable organic bases that can be used in this alkylation reaction are for example tertiary amines, e.g. trimethylamine, triethylamine, tripropylamine, ethyldiisopropylamine and the like, or basic N-heterocycles, such as morpholine, pyridine, lutidine, DMAP, DABCO, DBU or DBN.

The alkylation reaction is performed under conventional alkylation reaction conditions that are well known to the skilled person.

Step (iv.b)

In step (iv.b) of the process of the present invention, the compound obtained in step (iii) is subjected to an esterification reaction to obtain a compound of the general formula (I), wherein X represents a group $X_3$. The esterification reaction can be carried out according to known procedures.

Preferably, the compound obtained in step (iii) reacted with a $C_1$-$C_3$-carboxylic acid or with an anhydride of a $C_2$-$C_3$-carboxylic acid or with a $C_2$-$C_3$-carboxylic acid halide, preferably chloride, where in case that the carboxylic acid or the anhydride is used, the reaction is preferably carried out in the presence of an esterification catalyst, and when the carboxylic acid halide is used, the reaction is preferably carried out in the presence of a base.

The $C_1$-$C_3$-carboxylic acid used in step (iv.b) of the process of the present invention is formic acid, acetic acid or propionic acid. The $C_2$-$C_3$-carboxylic acid anhydride used in step (iv.b) of the process of the present invention is acetic anhydride or propionic anhydride. The $C_2$-$C_3$-carboxylic acid halide used in step (iv.b) of the process of the present invention is an acetic acid halide or propionic acid halide, preferably acetic acid chloride or propionic acid chloride.

In case a $C_1$-$C_3$-carboxylic acid or a $C_2$-$C_3$-carboxylic acid anhydride is applied, the reaction is typically performed in the presence of an esterification catalyst. In case a $C_2$-$C_3$-carboxylic acid chloride is applied, the reaction is typically performed in the presence of a base.

Suitable bases are preferably selected from organic bases. Suitable organic bases that can be used are for example tertiary amines, e.g. trimethylamine, triethylamine, tripropylamine, ethyldiisopropylamine and the like, or basic N-heterocycles, such as morpholine, pyridine, lutidine, DMAP, DABCO, DBU or DBN.

Suitable esterification catalysts that can be applied in this reaction are well known to the skilled person. Suitable esterification catalysts are for example metal based catalysts, e.g. iron, cadmium, cobalt, lead, zinc, antimony, magnesium, titanium and tin catalysts in the form of metals, metal oxides or metal salts, such as metal alcoxylates; mineral acids, such as sulfuric acid, hydrochloric acid or phosphoric acid; or organic sulfonic acids, such as methane sulfonic acid or para-toluene sulfonic acid.

The individual reaction conditions for the preparation of the ester compounds of the general formula (I), wherein X represents a group $X_3$, are well known to the skilled person.

Step (iv.c)

In step (iv.c) of the process of the present invention, the compound obtained in step (iii) is reacted with a carbonate $(R_3$—O$)_2$—(C=O), wherein $R^3$ is selected from hydrogen methyl, ethyl and phenyl, where at least one of $R^3$ is different from hydrogen, in the presence of a catalyst; or with a reagent $R^3$—O—C=O—$Y^1$, wherein $R^3$ is selected from hydrogen, methyl, ethyl and phenyl and $Y^1$ represents a leaving group, selected from —O-(tert.-butoxycarbonyl) and Cl, in the presence of a catalyst or a base, to obtain a compound of the general formula (I), wherein X represents a group $X_4$.

Preferably, the carbonate $(R^3$—O$)_2$—(C=O) is selected from dimethylcarbonate, diethylcarbonate or diphenylcarbonate, in particular from dimethylcarbonate and diethylcarbonate.

Preferably, the reagent $R_3$—O—C=O—$Y^1$ is selected from methoxycarbonyl 2,2-dimethylpropanoate, ethoxycarbonyl 2,2-dimethylpropanoate, phenoxycarbonyl 2,2-dimethylpropanoate, methyl carbonochloridate, ethyl carbonochloridate and phenyl carbonochloridate, in particular from methoxycarbonyl 2,2-dimethylpropanoate, ethoxycarbonyl 2,2-dimethylpropanoate, methyl carbonochloridate and ethyl carbonochloridate.

In case a carbonate $(R_3$—O$)_2$—(C=O) is applied, the reaction in step (iv.c) is typically performed in the presence of a catalyst, i.e. a transesterification catalyst. Suitable trans-carbonylation catalysts are for example the catalysts mentioned above in connection with the esterification reaction in step (iv.b).

In case a reagent $R_3$—O—C=O—$Y^1$ is applied, wherein the radical $Y^1$ is —O-(tert.-butoxycarbonyl), the reaction in step (iv.c) is typically performed in the presence of a catalyst, i.e. an alkoxycarbonylation catalyst. Suitable alkoxycarbonylation catalysts are for example Lewis acids, such as $BiCl_3$ or $Zn(OAc)_2$, phosphines, such as triphenylphosphine or tetrabromomethane.

In case a reagent $R^3$—O—C=O—$Y^1$ is applied, wherein the radical $Y^1$ is Cl, the reaction in step (iv.c) is typically performed in the presence of a base. Suitable bases are preferably selected from organic bases, as defined above.

The individual reaction conditions for the preparation of the carbonate compounds of the general formula (I), wherein X represents a group $X_4$, are well known to the skilled person. Suitable reaction conditions and protocols are for example described in "Homogeneous Carbonylation Reactions in the Synthesis of Compounds of Pharmaceutical Importance", by Rita Skoda-Földes, Chapter 12: "Alkoxycarbonylation of Alcohols and Phenols", and the references cited therein.

Generally, the reaction mixtures obtained in steps (i), (ii), (ii.a), (ii.b), (ii.c), (ii.a'), (ii.b'), (iii), (iv.a), (iv.b) and/or (iv.c) are worked up in a customary manner, for example by mixing with water and neutralizing the reaction mixture, if acids, such as Lewis acids, bases and/or metal organic reagents were applied in the reactions, separating the phases, isolating the product from the organic phases and, if appropriate, purifying the crude products by usual methods, e.g. by distillative, extractive or chromatographic methods. If the reaction is run in the presence of a heterogeneous catalyst, e.g. a supported Lewis-acid catalyst or a heterogeneous hydration catalyst, the catalyst is typically filtered off prior to work up.

The compounds of formulae (I), (II), (III) or (IV) or a mixture of two or more compounds of the formulae (I), (II), (III) and (IV), or a stereoisomer thereof or a mixture of two or more stereoisomers thereof, as defined above, are useful as aroma chemicals.

Accordingly, a further aspect of the present invention is the use of a compound of formulae (I), (II), (III) or (IV) or of a mixture of two or more compounds of the formulae (I), (II), (III) and (IV), or of a stereoisomer thereof or of a mixture of two or more stereoisomers thereof, as defined above, as an aroma chemical.

Preferably, the present invention relates to the use of a compound of formula (I), (II) or (III) or of a mixture of two or more compounds of the formulae (I), (II) and (III), or of a stereoisomer thereof or of a mixture of two or more stereoisomers thereof, as defined above, as an aroma chemical.

In an alternatively preferred embodiment, the present invention relates to the use of a compound of formula (I), (II) or (IV) or of a mixture of two or more compounds of the formulae (I), (II), (III) and (IV) [preferably of the formulae (I), (II) and (IV)], or of a stereoisomer thereof or of a mixture of two or more stereoisomers thereof, as defined above, as an aroma chemical. More preferably, the present invention relates to the use of a compound of formula (I), (II) or (IV), where in compounds (I) X is $X_1$, $X_2$ or $X_3$, where in compounds (II) $R^4$ is $C_2$-$C_4$-alkyl; or of a mixture of two or more compounds of the general formulae (I), (II), (III) and (IV) [preferably of the formulae (I), (II) and (IV)], where in compounds (I) X is $X_1$, $X_2$ or $X_3$, where in compounds (II) $R^4$ is $C_2$-$C_4$-alkyl; or of a stereoisomer thereof or of a mixture of two or more stereoisomers thereof. Even more preferably, the present invention relates to the use of a compound of formula (I), (II) or (IV), where in compounds (I) X is $X_1$, $X_2$ or $X_3$, where in $X_3R^2$ is methyl or ethyl, and where in compounds (II) $R^4$ is $C_2$-$C_4$-alkyl; or of a mixture of two or more compounds of the general formulae (I), (II), (III) and (IV) [preferably of the formulae (I), (II) and (IV)], where in compounds (I) X is $X_1$, $X_2$ or $X_3$, where in $X_3R^2$ is methyl or ethyl, and where in compounds (II) $R^4$ is $C_2$-$C_4$-alkyl; or of a stereoisomer thereof or of a mixture of two or more stereoisomers thereof. In particular, the present invention relates to the use of a compound of formula (I), (II) or (IV), where in compounds (I) X is $X_1$, $X_2$ or $X_3$, where in $X_3R^2$ is methyl, and where in compounds (II) $R^4$ is ethyl, or of a mixture of two or more compounds of the general formulae (I), (II), (III) and (IV) [preferably of the formulae (I), (II) and (IV)], where in compounds (I) X is $X_1$, $X_2$ or $X_3$, where in $X_3R^2$ is methyl, and where in compounds (II) $R^4$ is ethyl, or of a stereoisomer thereof or of a mixture of two or more stereoisomers thereof.

Specifically, a compound of formula (I), (II) or (IV) or a stereoisomer thereof or a mixture of two or more stereoisomers thereof is used.

In the context of the present invention, the term "aroma" refers to a sensory property and comprises an odor and/or a flavor.

The term "aroma chemical" denotes a substance which is used to obtain a sensory impression, to be more precise an olfactory or flavor impression, in particular a fragrance or flavor impression. The term "olfactory" denotes an odor impression without any positive or negative judgement, while the term "fragrance" (also termed "perfume" or "scent") is connected to an odor impression which is generally felt as pleasant. A flavor induces a taste impression.

The term "aroma profile" denotes the overall aroma impression of an aroma chemical and is composed of the individual aroma impressions of an aroma chemical.

The term "aroma composition", as used herein, refers to a composition which induces an aroma. The term aroma composition comprises "odor composition" and/or "flavor composition". An odor composition being a composition, which predominately induces an odor impression, a flavor composition being a composition, which predominantly induces a taste impression.

The term odor composition comprises "fragrance composition" or "scent composition" (used interchangeably herein), which predominately induce an odor impression which is generally felt as pleasant.

The terms "compound" and "substance" are used synonymously throughout the invention.

The term "substantivity" describes the interaction of an aroma chemical with a surface, such as for example the skin or a textile, especially after subsequent treatment of the surface, such as for example washing. The substantivity can for example be determined by washing a textile with a textile detergent composition comprising the aroma chemical and subsequent olfactory evaluation of the textile directly after washing (wet textile) as well as evaluation of the dry textile after prolonged storage.

The term "stability" describes the behavior of an aroma chemical upon contact with oxygen, light and/or other substances. An aroma chemical with high stability maintains its aroma profile over a long period in time, preferably in a large variety of compositions and under various storage conditions.

"Pleasant odor", "pleasant odor impression", "pleasant odiferous properties" are hedonistic expressions which describe the niceness and conciseness of an odor impression conveyed by an aroma chemical. The more general hedonistic expressions "advantageous sensory properties" or "advantageous organoleptic properties" describe the niceness and conciseness of an organoleptic impression conveyed by an aroma chemical. "Niceness" and "conciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also be the odor of musk or sandalwood. "Conciseness" generally refers to a spontaneously brought about sensory impression which—for the same test panel—brings about a reproducibly identical reminder of something specific. For example, a substance can have an odor which is spontaneously reminiscent of that of an "apple": the odor would then be concisely of "apples". If this apple odor were very pleasant because the odor is reminiscent, for example, of a sweet, fully ripe apple, the odor would be termed "nice". However, the odor of a typically tart apple can also be concise. If both reactions arise upon smelling the substance, in the example thus a nice and concise apple odor, then this substance has particularly advantageous sensory properties.

The term "odor-intensive substances" refers to substances or aroma chemicals exhibiting intense odor impressions. Intense odor impressions are to be understood as meaning those properties of aroma chemicals which permit a striking perception even in very low gas space concentrations. The intensity can be determined via a threshold value determination. A threshold value is the concentration of a substance in the relevant gas space at which an odor impression can just still be perceived by a representative test panel, although it no longer has to be defined. A substance class which probably belongs to the most odor-intensive known substance classes, i.e. has very low odor threshold values, are thiols, whose threshold value is often in the ppb/m$^3$ range.

Preferably, the compounds of formulae (I), (II), (III) or (IV) or a mixture of two or more compounds of the formulae (I), (II), (III) and (IV), or a stereoisomer thereof or a mixture of two or more stereoisomers thereof, as defined above, are used as a fragrance.

More preferably, the compounds of formulae (I), (II) or (III) or a mixture of two or more compounds of the formulae (I), (II) and (III), or a stereoisomer thereof or a mixture of two or more stereoisomers thereof, as defined above, are used as a fragrance.

In an alternatively more preferred embodiment, the compounds of formulae (I), (II) or (IV) or a mixture of two or more compounds of the formulae (I), (II), (III) and (IV) [preferably of the formulae (I), (II) and (IV)], or a stereoisomer thereof or a mixture of two or more stereoisomers thereof, as defined above, are used as a fragrance. Even more preferably, the compounds of formula (I), (II) or (IV), where in compounds (I) X is $X_1$, $X_2$ or $X_3$, where in compounds (II) $R^4$ is $C_2$-$C_4$-alkyl; or a mixture of two or more compounds of the general formulae (I), (II), (III) and (IV) [preferably of the formulae (I), (II) and (IV)], where in compounds (I) X is $X_1$, $X_2$ or $X_3$, where in compounds (II) $R^4$ is $C_2$-$C_4$-alkyl; or a stereoisomer thereof or a mixture of two or more stereoisomers thereof are used as a fragrance. Particularly preferably, the compounds of formula (I), (II) or (IV), where in compounds (I) X is $X_1$, $X_2$ or $X_3$, where in $X_3R^2$ is methyl or ethyl, and where in compounds (II) $R^4$ is $C_2$-$C_4$-alkyl; or a mixture of two or more compounds of the general formulae (I), (II), (III) and (IV) [preferably of the formulae (I), (II) and (IV)], where in compounds (I) X is $X_1$, $X_2$ or $X_3$, where in $X_3R^2$ is methyl or ethyl, and where in compounds (II) $R^4$ is $C_2$-$C_4$-alkyl; or a stereoisomer thereof or a mixture of two or more stereoisomers thereof are used as a fragrance. In particular, the compounds of formula (I), (II) or (IV), where in compounds (I) X is $X_1$, $X_2$ or $X_3$, where in $X_3R^2$ is methyl, and where in compounds (II) $R^4$ is ethyl, or a mixture of two or more compounds of the general formulae (I), (II), (III) and (IV) [preferably of the formulae (I), (II) and (IV)], here in compounds (I) X is $X_1$, $X_2$ or $X_3$, where in $X_3R^2$ is methyl, and where in compounds (II) $R^4$ is ethyl, or a stereoisomer thereof or a mixture of two or more stereoisomers thereof are used as a fragrance.

Specifically, a compound of formula (I), (II) or (IV) or a stereoisomer thereof or a mixture of two or more stereoisomers thereof is used.

In particular, 2-(2,4,5-trimethylcyclohex-2-en-1-yl)acetaldehyde is used to impart a green, watery, chrysanthema, grassy, aldehydic, lily of the valley, leathery, terpenic, and/or natural note. Since 2-(2,4,5-trimethylcyclohex-2-en-1-yl)acetaldehyde has a prominent lily of the valley odor note, 2-(2,4,5-trimethylcyclohex-2-en-1-yl)acetaldehyde can especially be used to impart a lily of the valley note. Thus, a particular embodiment of the invention relates to the use of 2-(2,4,5-trimethylcyclohex-2-en-1-yl)acetaldehyde to impart a lily of the valley note.

In particular, 6-(1-ethoxyethoxy)-1,4,5-trimethylcyclohex-1-ene is used to impart a watermelon, watery, green, almond, foodlike and technical note.

In particular, 2-(2,4,5-trimethylcyclohex-2-en-1-yl)ethan-1-ol is used to impart a crysantheme, green, herbal, dusty, diesel note.

In particular, 2-(2,4,5-trimethylcyclohex-2-en-1-yl)ethyl acetate is used to impart a floral, muguet note.

In particular, 6-(2-methoxyethyl)-1,3,4-trimethylcyclohex-1-ene is used to impart a moldy, sweet, leathery, agrumic, fresh, nutmeg note.

In particular, 6-(2-ethoxyethyl)-1,3,4-trimethylcyclohex-1-ene is used to impart a fruity note.

At concentrations of 1000 ppm or more, the intermediate (IV), i.e. 2,5,6-trimethylcyclohex-2-en-1-ol, is used to impart an animalic, indole, technical, solvent, pungent and/or phenolic note. At concentrations of 100 ppm in ethanol, however, 2,5,6-trimethylcyclohex-2-en-1-ol, imparts a phenolic, green banana, nutty, milky and/or warm note.

Accordingly, at concentrations in the range of from 0.1 to 400 ppm, preferably in the range of from 0.2 to 300 ppm, in particular in the range of from 0.5 to 200 ppm, 2,5,6-trimethylcyclohex-2-en-1-ol is used to imparts a phenolic, green banana, nutty, milky and/or warm note.

Preferably, the compounds of formulae (I), (II), (III) or (IV) or a mixture of two or more compounds of the formulae (I), (II), (III) and (IV), or a stereoisomer thereof or a mixture of two or more stereoisomers thereof, as defined above, are used in a composition selected from the group consisting of perfume compositions, body care compositions (including cosmetic compositions), products for oral and dental hygiene, hygiene articles, cleaning compositions (including dishwashing compositions), textile detergent compositions, compositions for scent dispensers, foods, food supplements, pharmaceutical compositions and crop protection compositions. The compounds of formulae (I), (II), (III) or (IV) or a mixture of two or more compounds of the formulae (I), (II), (III) and (IV), or a stereoisomer thereof or a mixture of two or more stereoisomers thereof are used as an aroma chemical, preferably as a fragrance, in the above compositions.

In particular, 2-(2,4,5-trimethylcyclohex-2-en-1-yl)acetaldehyde is used to impart a green, watery, chrysanthema, grassy, aldehydic, lily of the valley, leathery, terpenic, and/or natural note, especially a lily of the valley note, to the above-listed compositions.

In particular, 6-(1-ethoxyethoxy)-1,4,5-trimethylcyclohex-1-ene is used to impart a watermelon, watery, green, almond, foodlike and technical note to the above-listed compositions.

In particular, 2-(2,4,5-trimethylcyclohex-2-en-1-yl)ethan-1-ol is used to impart a crysantheme, green, herbal, dusty, diesel note to the above-listed compositions.

In particular, 2-(2,4,5-trimethylcyclohex-2-en-1-yl)ethyl acetate is used to impart a floral, muguet note to the above-listed compositions.

In particular, 6-(2-methoxyethyl)-1,3,4-trimethylcyclohex-1-ene is used to impart a moldy, sweet, leathery, agrumic, fresh, nutmeg note to the above-listed compositions.

In particular, 6-(2-ethoxyethyl)-1,3,4-trimethylcyclohex-1-ene is used to impart a fruity note to the above-listed compositions.

In particular, at concentrations of 1000 ppm or more, 2,5,6-trimethylcyclohex-2-en-1-ol is used to impart an animalic, indole, technical, solvent, pungent and/or phenolic note to the above-listed compositions.

In particular, at concentrations in the range of from 0.1 to 400 ppm, preferably in the range of from 0.2 to 300 ppm, in particular in the range of from 0.5 to 200 ppm, 2,5,6-trimethylcyclohex-2-en-1-ol imparts a phenolic, green banana, nutty, milky and/or warm note to the above-listed compositions.

Details to the above-listed compositions are given below.

Another aspect of the invention relates to the use of a compound of formulae (I), (II), (III) or (IV) or of a mixture of two or more compounds of the formulae (I), (II), (III) and (IV), or of a stereoisomer thereof or of a mixture of two or more stereoisomers thereof, as defined above, for modifying the scent character of a fragranced composition. Preferred compounds (I), (II), (III) and (IV), mixtures thereof and stereoisomers thereof to be used for this purpose correspond to those described above.

In addition to the olfactory properties, the compounds of formulae (I), (II), (III) or (IV) or a mixture of two or more compounds of the general formulae (I), (II), (III) and (IV), or a stereoisomer thereof or a mixture of two or more stereoisomers thereof exhibit advantageous secondary properties.

For example, they can provide better sensory profiles as a result of synergistic effects with other fragrances, which means that they can provide a booster effect for other fragrances. They can therefore be used as boosters for other fragrances.

Accordingly, another aspect of the invention relates to the use of a compound of formulae (I), (II), (III) or (IV) or mixtures of two or more compounds of formulae (I), (II), (III) and (IV), or a stereoisomer thereof or a mixtures of stereoisomers thereof as a booster for other fragrances.

Booster effect means that the substances enhance and intensify in perfumery formulations the overall impression of the mixture. In the mint range, for example, it is known that menthyl methyl ether intensifies the perfumery or taste mixtures of peppermint oils and particularly in top notes brings about a considerably more intensive and more complex perception although the ether itself, being a pure substance, develops no particular intensive odor at all. In fragrance applications, Hedione® (methyl dihydrojasmonate), which as a pure substance only exhibits a light floral jasmin-note, reinforces diffusion, freshness and volume of a perfume composition as an odor booster. Booster effects are particularly desired when top-note-characterized applications are required, in which the odor impression is to be conveyed particularly quickly and intensively, for example in deodorants, air fresheners or in the taste sector in chewing gums.

To achieve such a booster effect, the compounds of formulae (I), (II), (III) or (IV) or a mixture of two or more compounds of the formulae (I), (II), (III) and (IV), or a stereoisomer thereof or a mixture of two or more stereoisomers thereof are generally used in an overall amount of 0.1 to 20% by weight, preferably in an amount of 0.5 to 5% by weight, in particular in an amount of from 0.6 to 3% by weight, based on the total weight of the fragrance mixture.

Furthermore, the compounds of formulae (I), (II), (III) or (IV) or a mixture of two or more compounds of the formulae (I), (II), (III) and (IV), or a stereoisomer thereof or a mixture of two or more stereoisomers thereof can have further positive effects on the composition in which they are used. For example, they can enhance the overall performance of the composition into which they are incorporated, such as the stability, e.g. the formulation stability, the extendability or the substantivity of the composition.

In another aspect, the present invention relates to a composition comprising a compound of formulae (I), (II), (III) or (IV) or a mixture of two or more compounds of the formulae (I), (II), (III) and (IV), or of a stereoisomer thereof or of a mixture of two or more stereoisomers thereof.

Preferably, the composition comprises
a compound of formulae (I), (II), (III) or (IV) or a mixture of two or more compounds of the formulae (I), (II), (III) and (IV), or of a stereoisomer thereof or of a mixture of two or more stereoisomers thereof, as defined above; and
at least one further component selected from the group consisting of aroma chemicals, non-aroma chemical carriers, anti-oxidants and deodorant-active agents.

Preferably, the composition describe herein comprises a compound of formulae (I), (II) or (III) or a mixture of two or more compounds of the formulae (I), (II) and (III), or of a stereoisomer thereof or of a mixture of two or more stereoisomers thereof.

Accordingly, a preferred embodiment of the invention relates to a composition comprising
a compound of formulae (I), (II) or (III) or a mixture of two or more compounds of the formulae (I), (II) and (III), or a stereoisomer thereof or a mixture of two or more stereoisomers thereof, as defined above; and
at least one further component selected from the group consisting of aroma chemicals, non-aroma chemical carriers, anti-oxidants and deodorant-active agents.

In an alternatively preferred embodiment, the composition comprises a compound of formula (I), (II) or (IV) or a mixture of two or more compounds of the formulae (I), (II), (III) and (IV) [preferably of the formulae (I), (II) and (IV)], or a stereoisomer thereof or a mixture of two or more stereoisomers thereof.

Accordingly, an alternative preferred embodiment of the invention relates to a composition comprising
a compound of formula (I), (II) or (IV) or a mixture of two or more compounds of the formulae (I), (II), (III) and (IV) [preferably of the formulae (I), (II) and (IV)], or a stereoisomer thereof or a mixture of two or more stereoisomers thereof, as defined above; and
at least one further component selected from the group consisting of aroma chemicals, non-aroma chemical carriers, anti-oxidants and deodorant-active agents.

More preferably, the composition comprises a compound of formula (I), (II) or (IV), where in compounds (I) X is $X_1$, $X_2$ or $X_3$, where in compounds (II) $R^4$ is $C_2$-$C_4$-alkyl; or a mixture of two or more compounds of the general formulae (I), (II), (III) and (IV) [preferably of the formulae (I), (II) and (IV)], where in compounds (I) X is $X_1$, $X_2$ or $X_3$, where in compounds (II) $R^4$ is $C_2$-$C_4$-alkyl; or a stereoisomer thereof or a mixture of two or more stereoisomers thereof.

Accordingly, a more preferred embodiment of the invention relates to a composition comprising
a compound of formula (I), (II) or (IV), where in compounds (I) X is $X_1$, $X_2$ or $X_3$, where in compounds (II) $R^4$ is $C_2$-$C_4$-alkyl; or a mixture of two or more compounds of the formulae (I), (II), (III) and (IV) [preferably of the formulae (I), (II) and (IV)], where in compounds (I) X is $X_1$, $X_2$ or $X_3$, where in compounds (II) $R^4$ is $C_2$-$C_4$-alkyl; or a stereoisomer thereof or a mixture of two or more stereoisomers thereof, as defined above; and
at least one further component selected from the group consisting of aroma chemicals, non-aroma chemical carriers, anti-oxidants and deodorant-active agents.

Even more preferably, the composition comprises a compound of formula (I), (II) or (IV), where in compounds (I) X is $X_1$, $X_2$ or $X_3$, where in $X_3R^2$ is methyl or ethyl, and where in compounds (II) $R^4$ is $C_2$-$C_4$-alkyl; or a mixture of two or more compounds of the general formulae (I), (II), (III) and (IV) [preferably of the formulae (I), (II) and (IV)], where in compounds (I) X is $X_1$, $X_2$ or $X_3$, where in $X_3R^2$ is methyl or ethyl, and where in compounds (II) $R^4$ is $C_2$-$C_4$-alkyl; or a stereoisomer thereof or a mixture of two or more stereoisomers thereof.

Accordingly, an even more preferred embodiment of the invention relates to a composition comprising
a compound of formula (I), (II) or (IV), where in compounds (I) X is $X_1$, $X_2$ or $X_3$, where in $X_3R^2$ is methyl or ethyl, and where in compounds (II) $R^4$ is $C_2$-$C_4$-alkyl; or a mixture of two or more compounds of the formulae (I), (II), (III) and (IV) [preferably of the formulae (I), (II) and (IV)], where in compounds (I) X is $X_1$, $X_2$ or $X_3$, where in $X_3R^2$ is methyl or ethyl, and where in compounds (II) $R^4$ is $C_2$-$C_4$-alkyl; or a stereoisomer thereof or a mixture of two or more stereoisomers thereof, as defined above; and
at least one further component selected from the group consisting of aroma chemicals, non-aroma chemical carriers, anti-oxidants and deodorant-active agents.

In particular, the composition comprises a compound of formula (I), (II) or (IV), where in compounds (I) X is $X_1$, $X_2$ or $X_3$, where in $X_3R^2$ is methyl, and where in compounds (II) $R^4$ is ethyl, or a mixture of two or more compounds of the general formulae (I), (II), (III) and (IV) [preferably of the formulae (I), (II) and (IV)], where in compounds (I) X is $X_1$, $X_2$ or $X_3$, where in $X_3R^2$ is methyl, and where in compounds (II) R⁴ is ethyl, or a stereoisomer thereof or of a mixture of two or more stereoisomers thereof.

Accordingly, a particularly preferred embodiment of the invention relates to a composition comprising a compound of formula (I), (II) or (IV), where in compounds (I) X is $X_1$, $X_2$ or $X_3$, where in $X_3R^2$ is methyl, and where in compounds (II) R⁴ is ethyl; or a mixture of two or more compounds of the formulae (I), (II), (III) and (IV) [preferably of the formulae (I), (II) and (IV)], where in compounds (I) X is $X_1$, $X_2$ or $X_3$, where in $X_3R^2$ is methyl, and where in compounds (II) R⁴ is ethyl, or a stereoisomer thereof or a mixture of two or more stereoisomers thereof, as defined above; and at least one further component selected from the group consisting of aroma chemicals, non-aroma chemical carriers, anti-oxidants and deodorant-active agents.

Specifically, the composition comprises a compound of formula (I), (II) or (IV), a stereoisomer thereof or a mixture of two or more stereoisomers thereof.

The further aroma chemical is of course different from the compounds of formulae (I), (II), (III) or (IV), if present, or the stereoisomers thereof.

By virtue of their physical properties, the compounds of formulae (I), (II), (III) or (IV) or a mixture of two or more compounds of the formulae (I), (II), (III) and (IV), or a stereoisomer thereof or a mixture of two or more stereoisomers thereof have particularly good, virtually universal solvent properties for and in aroma chemicals and other customary ingredients in compositions such as, in particular, fragrance compositions. Therefore, they are well combinable with aroma chemicals, allowing, in particular, the creation of aroma compositions, in particular fragrance compositions, having novel advantageous sensory profiles. Furthermore, as already explained above, they can provide a booster effect for other fragrances.

Accordingly, in one preferred embodiment, the composition comprises a compound of formulae (I), (II), (III) or (IV) or a mixture of two or more compounds of the formulae (I), (II), (III) and (IV), or of a stereoisomer thereof or of a mixture of two or more stereoisomers thereof, as defined above; and at least one further aroma chemical.

The further aroma chemical can for example be one, preferably 2, 3, 4, 5, 6, 7, 8 or further aroma chemicals, selected from the group consisting of:

Geranyl acetate (3,7-Dimethyl-2,6 octadien-1yl acetate), alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60% by weight) (Hedione[9], Hedione HC[9]), 4,6,6,7,8,8-hexamethyl-1,3,4,6,7,8-hexahydrocyclopenta[g]benzopyran (Galaxolid[3]), tetrahydrolinalool (3,7-dimethyloctan-3-ol), ethyllinalool, benzyl salicylate, 2-methyl-3-(4-tert-butylphenyl)propanal (Lysmeral[2]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral[3]), alpha-amylcinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitral[1]), 2,4,4,7-tetramethyloct-6-en-3-one (Claritone[1]), 2,6-dimethyl-5-hepten-1-al (Melonal[2]), borneol, 3-(3-isopropylphenyl) butanal (Florhydral[2]), 2-methyl-3-(3,4-methylenedioxyphenyl)propanal (Helional[3]), 3-(4-ethylphenyl)-2,2-dimethylpropanal (Florazon[1]), 7-methyl-2H-1,5-benzodioxepin-3(4H)-one (Calone), 3,3,5-trimethylcyclohexyl acetate (preferably with a content of cis isomers of 70% by weight) or more and 2,5,5-trimethyl-1,2,3,4,4a,5,6,7-octahydronaphthalen-2-ol (Ambrinol S[1]), 3-(4-tert-butylphenyl)propanal (Bourgeonal[4]), ethyl 2-methylpentanoate (Manzanate[4]), ethoxymethoxycyclododecane (Amberwood[1]), 2,4-dimethyl-4,4a,5,9b-tetrahydroindeno[1,2-d][1,3]dioxine (Magnolan[1]), (2-tert-butylcyclohexyl) acetate (Verdox[3]) and 3-[5,5,6-trimethylbicyclo[2.2.1]hept-2-yl]cyclohexan-1-ol (Sandela[4]). Within the context of the present invention, the aforementioned aroma chemical(s) are accordingly preferably combined with the compound of formulae (I), (II), (III) or (IV) or a mixture of two or more compounds of formulae (I), (II), (III), and (IV), or a stereoisomer thereof or a mixture of stereoisomers thereof, as defined above.

Where trade names are given above, these refer to the following sources:
[1] trade name of Symrise GmbH, Germany;
[2] trade name of BASF SE;
[3] trade name of International Flavors & Fragrances Inc., USA;
[9] trade name of Firmenich S. A., Switzerland;
[10] trade name of PFW Aroma Chemicals B. V., the Netherlands.

A preferred embodiment of the invention relates to a composition comprising a compound of formulae (I), (II), (III) or (IV) or a mixture of two or more compounds of the formulae (I), (II), (III) and (IV), or a stereoisomer thereof or a mixture of two or more stereoisomers thereof, as defined above, and at least one further aroma chemical selected from the group consisting of methyl benzoate, benzyl acetate, geranyl acetate, 2-isobutyl-4-methyltetrahydro-2H-pyran-4-ol, linalool, 2-isobutyl-4-methyltetrahydro-2H-pyran-4-ol and methyl benzoate.

A preferred embodiment of the invention relates to a composition comprising a compound of formulae (I), (II), (III) or (IV) or a mixture of two or more compounds of the formulae (I), (II), (III) and (IV), or a stereoisomer thereof or a mixture of two or more stereoisomers thereof, as defined above, and at least one further aroma chemical selected from the group consisting of ethylvanillin, vanillin, 2,5-dimethyl-4-hydroxy-2H-furan-3-one (furaneol) or 3-hydroxy-2-methyl-4H-pyran-4-one (maltol).

Further aroma chemicals with which the compounds of formulae (I), (II), (III) or (IV) or a mixture of two or more compounds of the formulae (I), (II), (III) and (IV), or a stereoisomer thereof or a mixture of two or more stereoisomers thereof, as defined above, can be combined, e.g. to give a composition according to the invention, can be found e.g. in S. Arctander, Perfume and Flavor Chemicals, Vol. I and II, Montclair, N.J., 1969, self-published or K. Bauer, D. Garbe and H. Surburg, Common Fragrance and Flavor Materials, 4th Ed., Wiley-VCH, Weinheim 2001. Specifically, mention may be made of:

extracts from natural raw materials such as essential oils, concretes, absolutes, resins, resinoids, balsams, tinctures such as e.g.

ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; eucalyptus citriodora oil; eucalyptus oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea cubeba oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; wintergreen oil; hyssop oil; civet absolute; cinnamon leaf oil; cinnamon bark oil, and fractions thereof, or ingredients isolated therefrom;

individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-ylacetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethylacetals of geranial, neral, 7-hydroxy-3,7-dimethyloctanal; the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alphasinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethyl-cyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo-[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cycloheptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-methyl benzaldehyde; 4-methylphenylacetaldehyde; 3-(4-ethylphenyl)-2,2-dimethylpropanal; 2-methyl-3-(4-isopropyl phenyl)propanal; 2-methyl-3-(4-tert-butylphenyl)propanal; 2-methyl-3-(4-isobutyl phenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

The at least one non-aroma chemical carrier can be a compound, a mixture of compounds or other additives, which have no or no noteworthy sensory properties. Typically, the at least one non-aroma chemical carrier, if present in the compositions according to the present invention, is a compound, a mixture of compounds or other additives, which have no or no noteworthy sensory properties. The non-aroma chemical carrier serves for the dilution and/or the fixing of the aroma chemical(s), i.e. the compounds of formulae (I), (II), (III) or (IV) and optionally one or more further aroma chemical different from compounds (I), (II), (III) and (IV), as defined above, comprised in the composition.

Suitable carrier materials can be liquid or oil-like carrier materials as well as wax-like or solid carrier materials.

Preferably, the non-aroma chemical carrier, if present in the compositions according to the present invention, is selected from the group consisting of surfactants, oil components and solvents.

Accordingly, a further aspect of the invention is directed to a composition comprising the compounds of formulae (I), (II), (III) or (IV) or a mixture of two or more compounds of the formulae (I), (II), (III) and (IV), or a stereoisomer thereof or a mixture of two or more stereoisomers thereof, as defined above, and at least one further component selected from the group consisting of aroma chemicals, as defined above, surfactants, emollients (oil component), solvents, anti-oxidants and deodorant-active agents.

Another embodiment of the invention is directed to a composition comprising a compound of formulae (I), (II), (III) or (IV) or a mixture of two or more compounds of the formulae (I), (II), (III) and (IV), or a stereoisomer thereof or a mixture of two or more stereoisomers thereof, as defined above, and at least one further component selected from the group consisting of surfactants, emollients (oil component), solvents, anti-oxidants and deodorant-active agents.

Another embodiment of the invention is directed to a composition comprising a compound of formulae (I), (II), (III) or (IV) or a mixture of two or more compounds of the formulae (I), (II), (III) and (IV), or a stereoisomer thereof or a mixture of two or more stereoisomers thereof, as defined above, and at least one further component selected from the group consisting of emollients (oil component), solvents, anti-oxidants and deodorant-active agents.

Preferably, the compositions described above and below comprise a compound of formulae (I), (II) or (III) or a mixture of two or more compounds of the formulae (I), (II) and (III), or of a stereoisomer thereof or of a mixture of two or more stereoisomers thereof.

One embodiment of the invention is directed to a composition comprising a compound of formulae (I), (II), (III) or (IV) or a mixture of two or more compounds of the formulae (I), (II), (III) and (IV), or a stereoisomer thereof or a mixture of two or more stereoisomers thereof, as defined above, and at least one solvent.

In the context of the present invention, a "solvent" serves for the dilution of the compounds of formulae (I), (II), (III) or (IV) or a mixture of two or more compounds of the formulae (I), (II), (III) and (IV), or a stereoisomer thereof or a mixture of two or more stereoisomers thereof, as defined above, to be used according to the invention and/or any further component of the composition without having its own aroma.

The one or more solvent(s) can be present in the composition from 0.01 to 99% by weight based on the composition. In a preferred embodiment of the invention, the composition comprise 0.1 to 90 weight %, preferably 0.5 to 80 weight % of solvent(s) based on the composition. The amount of solvent(s) can be chosen depending on the composition. In one embodiment of the invention, the composition comprises 0.05 to 10 weight %, preferably 0.1 to 5 weight %, more preferably 0.2 to 3 weight % based on the composition. In one embodiment of the invention, the composition comprises 20 to 70 weight %, preferably 25 to 50 weight % of solvent(s) based on the composition.

Preferred solvents are ethanol, isopropanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), and benzyl benzoate (BB).

In a more preferred embodiment of the invention, the solvent is selected from the group consisting of ethanol, isopropanol, diethylene glycol monoethyl ether, glycerol, propylene glycol, 1,2-butylene glycol, dipropylene glycol, triethyl citrate, benzyl benzoate and isopropyl myristate.

Especially preferred solvents are selected from the group consisting of ethanol, propylene glycol, dipropylene glycol, triethyl citrate, benzyl benzoate and isopropyl myristate.

One embodiment of the invention is directed to a composition comprising a compound of formulae (I), (II), (III) or (IV) or a mixture of two or more compounds of formulae (I), (II), (III) and (IV), or a stereoisomer thereof or a mixture of stereoisomers thereof, as defined above, and at least one anti-oxidant.

Anti-oxidants are able to inhibit or prevent the undesired changes in the compositions to be protected caused by oxygen effects and other oxidative processes. The effect of the anti-oxidants consists in most cases in them acting as free-radical scavengers for the free radicals which arise during autoxidation.

Anti-oxidants can for example be selected from the group consisting of
- amino acids (for example glycine, alanine, arginine, serine, threonine, histidine, tyrosine, tryptophan) and derivatives thereof,
- imidazoles (e.g. urocanic acid) and derivatives thereof,
- peptides, such as D,L-carnosine, D-carnosine, L-carnosine (=β-Alanyl-L-histidin) and derivatives thereof,
- carotenoids, carotenes (e.g. alpha-carotene, beta-carotene, lycopene, lutein) or derivatives thereof,
- chlorogenic acid and derivatives thereof,
- lipoic acid and derivatives thereof (for example dihydrolipoic acid),
- auro-thioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, gamma-linoleyl, cholesteryl and glyceryl esters thereof) and salts thereof,
- dilauryl thiodipropionate, distearyl thiodipropionate, thiodipropionic acid and derivatives thereof (esters, ethers, peptides, lipids, nucleotides, nucleosides and salts),
- sulfoximine compounds (for example buthionine sulfoximines, homocysteine sulfoximine, buthionine sulfones, penta-, hexa-, heptathionine sulfoximine),
- (metal) chelating agents (e.g. alpha-hydroxy fatty acids, palmitic acid, phytic acid, lactoferrin),
- alpha-hydroxy acids (for example citric acid, lactic acid, malic acid),
- humic acid, bile acid, bile extracts, bilirubin, biliverdin, boldin (=alkaloid from the plant Peumus boldus, boldo extract,
- EDTA, EGTA and derivatives thereof,
- unsaturated fatty acids and derivatives thereof (e.g. gamma-linolenic acid, linoleic acid, oleic acid),
- folic acid and derivatives thereof,
- ubiquinone and ubiquinol and derivatives thereof,
- vitamin C and derivatives (for example ascorbyl palmitate, Mg ascorbyl phosphate, ascorbyl acetate),
- tocopherols and derivatives (for example vitamin E acetate),
- vitamin A and derivatives (for example vitamin A palmitate),
- coniferyl benzoate of gum benzoin, rutic acid and derivatives thereof, alpha-glycosylrutin, ferulic acid, furfurylideneglucitol,
- butylhydroxytoluene (BHT), butylhydroxyanisole (BHA),
- nordihydroguaiacic acid, nordihydroguaiaretic acid, trihydroxybutyrophenone, uric acid and derivatives thereof, mannose and derivatives thereof,
- superoxide dismutase,
- zinc and derivatives thereof (for example ZnO, $ZnSO_4$),
- selenium and derivatives thereof (for example selenomethionine) and
- stilbenes and derivatives thereof (e.g. stilbene oxide, trans-stilbene oxide).

In a preferred embodiment, the anti-oxidant is selected from the group consisting of pentaerythrityl, tetra-di-t-butyl hydroxyhydrocinnamate, nordihydroguaiaretic acid, ferulic acid, resveratrol, propyl gallate, butylhydroxytoluene (BHT), butylhydroxyanisole (BHA), ascorbyl palmitate and tocopherol.

The compositions according to the invention can comprise the anti-oxidants in an amount of 0.001 to 25 wt.-%, preferably 0.005 to 10 wt.-%, preferably 0.01 to 8 wt.-%, preferably 0.025 to 7 wt.-%, preferably 0.05 to 5 wt.-%, based on the total weight of the composition.

The compounds of formulae (I), (II), (III) or (IV) or a mixture of two or more compounds of the formulae (I), (II), (III) and (IV), or a stereoisomer thereof or a mixture of two or more stereoisomers thereof, as defined above, can also be used together with deodorizing compositions.

Deodorizing compositions (deodorants and antiperspirants) counteract, mask or eliminate body odors. Body odors are formed through the action of skin bacteria on apocrine perspiration which results in the formation of unpleasant-smelling degradation products.

One embodiment of the invention is therefore directed to a composition comprising a compound of formulae (I), (II), (III) or (IV) or a mixture of two or more compounds of the formulae (I), (II), (III) and (IV), or a stereoisomer thereof or a mixture of two or more stereoisomers thereof, as defined above, and at least one deodorant-active agent.

In a preferred embodiment of the invention, the at least one deodorant-active agent is selected from the groups consisting of anti-perspirants, esterase inhibitors and anti-bacterial agents.

Suitable antiperspirants can be selected from the group consisting of salts of aluminium, zirconium or zinc. Examples are aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Aluminium chlorohydrate, aluminium zirconium tetrachlorohydrate, aluminium zirconium pentachlorohydrate and complex compounds thereof are preferably used.

In a preferred embodiment of the invention the compositions comprise at least one antiperspirant selected from the group consisting aluminium chloride, aluminium chlorohydrate, aluminium dichlorohydrate, aluminium sesquichlorohydrate, aluminium hydroxyallantoinate, aluminium chloride tartrate, aluminium zirconium trichlorohydrate, aluminium zirconium tetrachlorohydrate and aluminium zirconium pentachlorohydrate The compositions according to the invention can comprise the antiperspirants in an amount of 1 to 50, preferably 5 to 30 and more particularly 10 to 25 wt.-%, based on the solids content of the composition.

Where perspiration is present in the underarm region, extracellular enzymes-esterases, mainly proteases and/or lipases are formed by bacteria and split the esters present in the perspiration, releasing odors in the process. Suitable esterase inhibitors are for example trialkyl citrates, such as trimethyl citrate, tripropyl citrate, triisopropyl citrate, tributyl citrate and, in particular, triethyl citrate. Esterase inhibitors inhibit enzyme activity and thus reduce odor formation. The free acid is probably released by the cleavage of the citric acid ester and reduces the pH value of the skin to such an extent that the enzymes are inactivated by acylation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

In a preferred embodiment of the invention the compositions comprise at least one esterase inhibitor selected from the group consisting of trimethyl citrate, tripropyl citrate, triisopropyl citrate, tributyl citrate triethyl citrate, lanosterol, cholesterol, campesterol, stigmasterol, sitosterol sulfate, sitosterol phosphate, glutaric acid, glutaric acid monoethyl ester, glutaric acid diethyl ester, adipic acid, adipic acid monoethyl ester, adipic acid diethyl ester, malonic acid, malonic acid diethyl ester, citric acid, malic acid, tartaric acid, tartaric acid diethyl ester and zinc glycinate.

The compositions according to the invention can comprise the esterase inhibitors in amounts of 0.01 to 20, preferably 0.1 to 10 and more particularly 0.5 to 5 wt.-%, based on the solids content of the composition.

The term "anti-bacterial agents" as used herein encompasses substances which have bactericidal and/or bacteriostatic properties. Typically these substances act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acidN-alkylamides such as, for example, salicylic acid-n-octyl amide or salicylic acid-n-decyl amide.

In a preferred embodiment the antibacterial agent is selected from the group consisting of chitosan, phenoxyethanol, 5-Chloro-2-(2,4-dichlorophenoxy)-phenol, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), phenoxyethanol, glycerol monocaprate, glycerol monocaprylate, glycerol monolaurate (GML), diglycerol monocaprate (DMC), salicylic acid-N-alkylamides.

The compositions according to the invention can comprise the antibacterial agents in amounts of 0.01 to 5 wt. % and preferably 0.1 to 2 wt.-%, based on the solids content of the composition.

According to a further aspect, the compounds of formulae (I), (II), (III) or (IV) or a mixture of two or more compounds of the formulae (I), (II), (III) and (IV), or a stereoisomer thereof or a mixture of two or more stereoisomers thereof are suitable for use in surfactant-containing compositions. According to their characteristic scent profiles, they can especially be used for the perfuming of surfactant-containing compositions such as, for example, cleaners (in particular laundry care products and all-purpose cleaners).

The compositions according to the invention can thus preferably comprise at least one surfactant. The surfactant(s) may be selected from anionic, non-ionic, cationic and/or amphoteric or zwitterionic surfactants. Surfactant-containing compositions, such as for example shower gels, foam baths, shampoos, etc., preferably contain at least one anionic surfactant.

The compositions according to the invention usually contain the surfactant(s), in the aggregate, in a quantity of 0 to 40% by weight, preferably 0 to 20% by weight, more preferably 0.1 to 15% by weight, and particularly 0.1 to 10% by weight, based on the total weight of the composition. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en) yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a $C_8$ to $C_{18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalk-ylaminopropionate, cocoacylaminoethyl aminopropionate and acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear $C_{12}$-$C_{18}$ alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trim ethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

One embodiment of the invention is directed to a composition comprising a compound of formulae (I), (II), (III) or (IV) or a mixture of two or more compounds of formulae (I), (II), (III) and (IV), or a stereoisomer thereof or a mixture of stereoisomers thereof, as defined above, and at least one oil component.

The oil components are typically present in a total quantity of 0.1 to 80, preferably 0.5 to 70, more preferably 1 to 60, even more preferably 1 to 50% by weight, in particular 1 to 40% by weight, more particularly 5 to 25% by weight and specifically 5 to 15% by weight based on the composition.

The oil components may be selected, for example, from Guerbet alcohols based on fatty alcohols containing 6 to 18 and preferably 8 to 10 carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl ole-ate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$-alkyl-hydroxycarboxylic acids with linear or branched $C_6$-$C_{22}$-fatty alcohols, more especially dioctyl malate, esters of linear and/or branched fatty acids with polyhydric alcohols (for example propylene glycol, dimer dial or trimer triol), triglycerides based on $C_6$-$C_{10}$-fatty acids, liquid mono-, di- and triglyceride mixtures based on $C_6$-$C_{18}$-fatty acids, esters of $C_6$-$C_{22}$-fatty alcohols and/or Guerbet alcohols with aromatic carboxylic acids, more particularly benzoic acid, esters of dicarboxylic acids with polyols containing 2 to 10 car-bon atoms and 2 to 6 hydroxyl groups, vegetable oils, branched primary alcohols, substituted cyclohexanes, linear and branched $C_6$-$C_{22}$-fatty alcohol carbonates such as, for example, dicaprylyl carbonate (Cetiol® CC), Guerbet carbonates based on fatty alcohols containing 6 to 18 and preferably 8 to 10 carbon atoms, esters of benzoic acid with linear and/or branched $C_6$ to $C_{22}$-alcohols (for example Finsolv® TN), linear or branched, symmetrical or non-symmetrical dialkyl ethers containing 6 to 22 carbon atoms per alkyl group such as, for example, dicaprylyl ether (Cetiol® OE), ring opening products of epoxidized fatty acid esters with polyols and hydrocarbons or mixtures thereof.

The compounds of formulae (I), (II), (III) or (IV) or a mixture of two or more compounds of the formulae (I), (II), (III) and (IV), or a stereoisomer thereof or a mixture of two or more stereoisomers thereof, as defined above, can be used in a wide range of aroma compositions. The olfactory properties, the substance properties (such as solubility in customary solvents and compatibility with further customary constituents of such compositions), as well as the toxicological acceptability of the compounds of formulae (I), (II), (III) or (IV) or a mixture of two or more compounds of the formulae (I), (II), (III) and (IV), or a stereoisomer thereof or a mixture of two or more stereoisomers thereof underline their particular suitability for the stated use purposes and compositions.

Accordingly, in a preferred embodiment of the invention, the composition is an aroma composition, more preferably an odor composition, more preferably a fragrance composition.

The composition according to the invention can be selected from, but is not limited to, the group consisting of perfume compositions, body care compositions, products for oral and dental hygiene, hygiene articles, cleaning compositions, textile detergent compositions, composition for scent dispensers, foods, food supplements, pharmaceutical compositions and crop protection compositions.

Non-limiting examples for body care composition are cosmetic compositions. Non-limiting examples for cleaning composition are dishwashing compositions.

Perfume compositions can be selected from fine fragrances, air fresheners in liquid form, gel-like form or a form applied to a solid carrier, aerosol sprays, scented cleaners, perfume candles and oils, such as lamp oils or oils for massage.

Examples for fine fragrances are perfume extracts, Eau de Parfums, Eau de Toilettes, Eau de Colognes, Eau de Solide and Extrait Partum.

Body care compositions include cosmetic compositions, and can be selected from after-shaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, after-sun creams and lotions, hand creams and lotions, foot creams and lotions, hair removal creams and lotions, after-shave creams and lotions, tanning creams and lotions, hair care products, such as e.g. hairsprays, hair gels, setting hair lotions, hair conditioners, hair shampoo, permanent and semi-permanent hair colorants, hair shaping compositions, such as cold waves and hair smoothing compositions, hair tonics, hair creams and hair lotions, deodorants and antiperspirants, such as e.g. underarm sprays, roll-ons, deodorant sticks and deodorant creams, products of decorative cosmetics, such as e.g. eye-liners, eye-shadows, nail varnishes, make-ups, lipsticks and mascara.

Products for oral and dental hygiene include toothpaste, dental floss, mouth wash, breath fresheners, dental foam, dental gels and dental strips.

Hygiene articles can be selected from joss sticks, insecticides, repellents, propellants, rust removers, perfumed freshening wipes, armpit pads, baby diapers, sanitary towels, toilet paper, cosmetic wipes, pocket tissues, dishwasher and deodorizer.

Cleaning compositions, such as e.g. cleaners for solid surfaces, can be selected from perfumed acidic, alkaline and neutral cleaners, such as e.g. floor cleaners, window cleaners, dishwashing detergents both for handwashing and machine washing use, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners.

Textile detergent compositions can be selected from liquid detergents, powder detergents, laundry pretreatments such as bleaches, soaking agents and stain removers, fabric softeners, washing soaps and washing tablets.

Food means a raw, cooked, or processed edible substance, ice, beverage or ingredient used or intended for use in whole or in part for human consumption, or chewing gum, gummies, jellies, and confectionaries.

A food supplement is a product intended for ingestion that contains a dietary ingredient intended to add further nutritional value to the diet. A dietary ingredient may be one, or any combination, of the following substances: a vitamin, a mineral, an herb or other botanical, an amino acid, a dietary substance for use by people to supplement the diet by increasing the total dietary intake, a concentrate, metabolite, constituent, or extract. Food supplements may be found in many forms such as tablets, capsules, softgels, gelcaps, liquids, or powders.

Pharmaceutical compositions comprise compositions which are intended for use in the diagnosis, cure, mitigation, treatment, or prevention of disease as well as articles (other than food) intended to affect the structure or any function of the body of man or other animals.

Crop protection compositions comprise compositions which are intended for the managing of plant diseases, weeds and other pests (both vertebrate and invertebrate) that damage agricultural crops and forestry.

The compositions according to the invention can further comprise one or more substances, such as, for example: preservatives, abrasives, anti-acne agents, agents to combat skin aging, antibacterial agents, anti-cellulite agents, anti-dandruff agents, anti-inflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, oils, waxes, fats, phospholipids, saturated fatty acids, mono- or polyunsaturated fatty acids, α-hydroxy acids, polyhydroxy fatty acids, liquefiers, dyes, color-protection agents, pigments, anticorrosives, polyols, surfactants, electrolytes, organic solvents or silicone derivatives.

The compounds of formulae (I), (II), (III) or (IV) or a mixture of two or more compounds of the formulae (I), (II), (III) and (IV), or a stereoisomer thereof or a mixture of two or more stereoisomers thereof, as defined above, as well as the compositions according to the invention comprising them can also be in microencapsulated form, spray-dried form, in the form of inclusion complexes or in the form of extrusion products. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising the compounds of formulae (I), (II), (III) or (IV) or a mixture of two or more compounds of the formulae (I), (II), (III) and (IV), or a stereoisomer thereof or a mixture of two or more stereoisomers thereof, as defined above, and composition obtainable by the above method of the invention, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting the compounds of formulae (I), (II), (III) or (IV) or a mixture of two or more compounds of the formulae (I), (II), (III) and (IV), or a stereoisomer thereof or a mixture of two or more stereoisomers thereof, as defined above, or the composition obtainable by the above method of the invention with a suitable wax-like substance and by extrusion with subsequent solidification, optionally in a suitable solvent, e.g. isopropanol.

Generally, the total amount of the compounds of formulae (I), (II), (III) or (IV) or a mixture of two or more compounds of the formulae (I), (II), (III) and (IV), or a stereoisomer thereof or a mixture of two or more stereoisomers thereof, in the compositions according to the present invention is typically adapted to the particular intended use or the intended application and can, thus, vary over a wide range. As a rule, the customary standard commercial amounts for scents are used.

The compositions according to the invention can comprise the compounds of formulae (I), (II), (III) or (IV) or a mixture of two or more compounds of the formulae (I), (II), (III) and (IV), or a stereoisomer thereof or a mixture of two or more stereoisomers thereof, as defined above, in an overall amount of from 0.001 to 99.9% by weight, preferably from 0.01 to 90% by weight, more preferably from 0.05 to 80%, in particular from 0.1 to 60% by weight, more particularly from 0.1 to 40% by weight, e.g. from 0.1 to 10% by weight or 0.1 to 15% by weight, based on the total weight of the composition.

In one embodiment of the invention, the compositions comprise the compounds of formulae (I), (II), (III) or (IV) or a mixture of two or more compounds of the formulae (I), (II), (III) and (IV), or a stereoisomer thereof or a mixture of two or more stereoisomers thereof, as defined above, in an overall amount of from 0.001 to 5 weight %, preferably from 0.01 to 2 weight % based on the total weight of the composition.

A further aspect of the invention is directed to a method of preparing a composition, in particular an aroma composition, especially a fragranced composition, specifically a ready-to-use fragranced composition, or for modifying the scent character of a composition, in particular of an aroma composition, in particular of a fragranced composition, specifically of a ready-to-use fragranced composition, comprising incorporating a compound of formula (I), (II), (III) or (IV) or a mixture of two or more compounds of the general formulae (I), (II), (III) and (IV), or a stereoisomer thereof or a mixture of two or more stereoisomers thereof as defined above, into said composition, to be more precise into the target composition, resulting in an aroma composition, in particular in a fragranced composition, specifically in a ready-to-use fragranced composition.

Alternatively, the invention is directed to a method of preparing an aroma chemical composition, in particular a fragranced composition, especially a fragranced ready-to-use composition, comprising mixing a compound of formula (I), (II), (III) or (IV) or a mixture of two or more compounds of the general formulae (I), (II), (III) and (IV), or of a stereoisomer thereof or of a mixture of two or more stereoisomers thereof as defined above with at least one aroma chemical different from these compounds and/or with at least one non-aroma chemical carrier and/or with at least one antioxidant and/or with at least one deodorant-active agent. Suitable and preferred aroma chemicals different from these compounds, non-aroma chemical carriers, antioxidants and deodorant-active agents are described above. For example, the method can be carried out by mixing a compound of formula (I), (II), (III) or (IV) or a mixture of two or more compounds of the general formulae (I), (II), (III) and (IV), or a stereoisomer thereof or a mixture of two or more stereoisomers thereof as defined above and at least one further component selected from the group consisting of aroma chemicals different from these compounds, non-aroma chemical carriers, antioxidants and deodorant-active agents.

Preferably, the invention is directed to a method of preparing a composition, in particular an aroma composition, especially a fragranced composition, specifically a ready-to-use fragranced composition, or for modifying the scent character of a composition, in particular of an aroma composition, especially of a fragranced composition, comprising incorporating a compound of formulae (I), (II) or (III), preferably a compound (I) or (II), or a mixture of two or more compounds of the general formulae (I), (II) and (III), preferably a compound (I) or (II), or of a stereoisomer thereof or of a mixture of two or more stereoisomers thereof as defined above, into said composition, to be more precise into the target composition, resulting in an aroma composition, in particular in a fragranced composition, specifically in a ready-to-use fragranced composition.

In an alternative preferred embodiment, the invention is directed to a method of preparing a composition, in particular an aroma composition, especially a fragranced composition, specifically a ready-to-use fragranced composition, or for modifying the scent character of a composition, in particular of an aroma composition, especially of a fragranced composition, comprising incorporating a compound of formulae (I), (II) or (IV), preferably a compound (I) or (II), or a mixture of two or more compounds of the general formulae (I), (II) and (IV), preferably a compound (I) or (II), or of a stereoisomer thereof or of a mixture of two or more stereoisomers thereof as defined above, into said composition, to be more precise into the target composition, resulting in an aroma composition, in particular in a fragranced composition, specifically in a ready-to-use fragranced composition.

In particular, the invention is directed to a method of preparing a perfume composition, body care composition, product for oral and dental hygiene, hygiene article, cleaning composition, textile detergent composition, food, food supplement, pharmaceutical composition or crop protection composition, comprising incorporating a compound of formulae (I), (II), (III) or (IV) or a mixture of two or more compounds of the general formulae (I), (II), (III) and (IV), or of a stereoisomer thereof or of a mixture of two or more stereoisomers thereof, as defined above, into said perfume composition, body care composition, product for oral and dental hygiene, hygiene article, cleaning composition, textile detergent composition, food, food supplement, pharmaceutical composition or crop protection composition.

Especially, the invention is directed to a method of preparing a perfume composition, body care composition, product for oral and dental hygiene, hygiene article, cleaning composition, textile detergent composition, food, food supplement, pharmaceutical composition or crop protection composition, comprising incorporating a compound of formulae (I), (II) or (III), preferably a compound (I) or (II), or a mixture of two or more compounds of the general formulae (I), (II) and (III), preferably a compound (I) or (II), or of a stereoisomer thereof or of a mixture of two or more stereoisomers thereof, as defined above, into said perfume composition, body care composition, product for oral and dental hygiene, hygiene article, cleaning composition, textile detergent composition, food, food supplement, pharmaceutical composition or crop protection composition.

In an alternative specific embodiment, the invention is directed to a method of preparing a perfume composition, body care composition, product for oral and dental hygiene, hygiene article, cleaning composition, textile detergent composition, food, food supplement, pharmaceutical composition or crop protection composition, comprising incorporating a compound of formulae (I), (II) or (IV), preferably a compound (I) or (II), or a mixture of two or more compounds of the general formulae (I), (II) and (IV), preferably a compound (I) or (II), or of a stereoisomer thereof or of a mixture of two or more stereoisomers thereof, as defined above, into said perfume composition, body care composition, product for oral and dental hygiene, hygiene article, cleaning composition, textile detergent composition, food, food supplement, pharmaceutical composition or crop protection composition.

In particular, 2-(2,4,5-trimethylcyclohex-2-en-1-yl)acetaldehyde is used to impart a green, watery, chrysanthema, grassy, aldehydic, lily of the valley, leathery, terpenic and/or natural note, especially a lily of the valley note, to the above-listed compositions.

In particular, 6-(1-ethoxyethoxy)-1,4,5-trimethylcyclohex-1-ene is used to impart a watermelon, watery, green, almond, foodlike and technical note to the above-listed compositions.

In particular, 2-(2,4,5-trimethylcyclohex-2-en-1-yl)ethan-1-ol is used to impart a crysantheme, green, herbal, dusty, diesel note to the above-listed compositions.

In particular, 2-(2,4,5-trimethylcyclohex-2-en-1-yl)ethyl acetate is used to impart a floral, muguet note to the above-listed compositions.

In particular, 6-(2-methoxyethyl)-1,3,4-trimethylcyclohex-1-ene is used to impart a moldy, sweet, leathery, agrumic, fresh, nutmeg note to the above-listed compositions.

In particular, 6-(2-ethoxyethyl)-1,3,4-trimethylcyclohex-1-ene is used to impart a fruity note to the above-listed compositions.

In particular, at concentrations of 1000 ppm or more, 2,5,6-trimethylcyclohex-2-en-1-ol is used to impart an animalic, indole, technical, solvent, pungent and/or phenolic note to the above-listed compositions.

In particular, at concentrations in the range of from 0.1 to 400 ppm, preferably in the range of from 0.2 to 300 ppm, in particular in the range of from 0.5 to 200 ppm, 2,5,6-trimethylcyclohex-2-en-1-ol is used to imparts a phenolic, green banana, nutty, milky and/or warm note to the above-listed compositions.

Accordingly, one embodiment of the invention is directed to a method for imparting a green, watery, chrysanthema, grassy, aldehydic, lily of the valley note, leathery, terpenic and/or natural note, especially a lily of the valley note, to a perfume composition, body care composition, product for oral and dental hygiene, hygiene article, cleaning composition, textile detergent composition, food, food supplement, pharmaceutical composition or crop protection composition, which comprises including 2-(2,4,5-trimethylcyclohex-2-en-1-yl)acetaldehyde in a perfume composition, body care composition, product for oral and dental hygiene, hygiene article, cleaning composition, textile detergent composition, food, food supplement, pharmaceutical composition or crop protection composition.

Another embodiment of the invention is directed to a method for imparting a watermelon, watery, green, almond, foodlike and technical note to a perfume composition, body care composition, product for oral and dental hygiene, hygiene article, cleaning composition, textile detergent composition, food, food supplement, pharmaceutical composition or crop protection composition, which comprises including 6-(1-ethoxyethoxy)-1,4,5-trimethylcyclohex-1-ene in a perfume composition, body care composition, product for oral and dental hygiene, hygiene article, cleaning composition, textile detergent composition, food, food supplement, pharmaceutical composition or crop protection composition.

Another embodiment of the invention is directed to a method for imparting a crysantheme, green, herbal, dusty, diesel note to a perfume composition, body care composition, product for oral and dental hygiene, hygiene article, cleaning composition, textile detergent composition, food, food supplement, pharmaceutical composition or crop protection composition, which comprises including 2-(2,4,5-trimethylcyclohex-2-en-1-yl)ethan-1-ol in a perfume composition, body care composition, product for oral and dental hygiene, hygiene article, cleaning composition, textile detergent composition, food, food supplement, pharmaceutical composition or crop protection composition.

Another embodiment of the invention is directed to a method for imparting a floral, muguet note to a perfume composition, body care composition, product for oral and dental hygiene, hygiene article, cleaning composition, textile detergent composition, food, food supplement, pharmaceutical composition or crop protection composition, which comprises including 2-(2,4,5-trimethylcyclohex-2-en-1-yl) ethyl acetate in a perfume composition, body care composition, product for oral and dental hygiene, hygiene article, cleaning composition, textile detergent composition, food, food supplement, pharmaceutical composition or crop protection composition.

Another embodiment of the invention is directed to a method for imparting a moldy, sweet, leathery, agrumic, fresh, nutmeg note to a perfume composition, body care composition, product for oral and dental hygiene, hygiene article, cleaning composition, textile detergent composition, food, food supplement, pharmaceutical composition or crop protection composition, which comprises including 6-(2-methoxyethyl)-1,3,4-trimethylcyclohex-1-ene in a perfume composition, body care composition, product for oral and dental hygiene, hygiene article, cleaning composition, textile detergent composition, food, food supplement, pharmaceutical composition or crop protection composition.

Another embodiment of the invention is directed to a method for imparting a fruity note to a perfume composition, body care composition, product for oral and dental hygiene, hygiene article, cleaning composition, textile detergent composition, food, food supplement, pharmaceutical composition or crop protection composition, which comprises including 6-(2-ethoxyethyl)-1,3,4-trimethylcyclohex-1-ene in a perfume composition, body care composition, product for oral and dental hygiene, hygiene article, cleaning composition, textile detergent composition, food, food supplement, pharmaceutical composition or crop protection composition.

Another embodiment of the invention is directed to a method for imparting an animalic, indole, technical, solvent, pungent and/or phenolic note to a perfume composition, body care composition, product for oral and dental hygiene, hygiene article, cleaning composition, textile detergent composition, food, food supplement, pharmaceutical composition or crop protection composition, which comprises including 2,5,6-trimethylcyclohex-2-en-1-ol at concentrations of 1000 ppm or more in said perfume composition, body care composition, product for oral and dental hygiene, hygiene article, cleaning composition, textile detergent composition, food, food supplement, pharmaceutical composition or crop protection composition.

Another embodiment of the invention is directed to a method for imparting a phenolic, green banana, nutty, milky and/or warm note to a perfume composition, body care composition, product for oral and dental hygiene, hygiene article, cleaning composition, textile detergent composition, food, food supplement, pharmaceutical composition or crop protection composition, which comprises including 2,5,6-trimethylcyclohex-2-en-1-ol at concentrations in the range of from 0.1 to 400 ppm, preferably in the range of from 0.2 to 300 ppm, in particular in the range of from 0.5 to 200 ppm, in said perfume composition, body care composition, product for oral and dental hygiene, hygiene article, cleaning composition, textile detergent composition, food, food supplement, pharmaceutical composition or crop protection composition.

The invention is illustrated by the following examples.

EXAMPLES

Abbreviations:
GC: gas chromatography
GC-a %: GC area-%
HPLC: high performance liquid chromatography
MTBE: methyl tert.-butyl ether
cis-VI stands for an isomer mixture of (5R,6R)-2,5,6-trimethylcyclohex-2-en-1-one and (5S,6S)-2,5,6-trimethylcyclohex-2-en-1-one.
trans-VI stands for an isomer mixture of (5R,6S)-2,5,6-trimethylcyclohex-2-en-1-one and (5S,6R)-2,5,6-trimethylcyclohex-2-en-1-one.
2,5-trans-6-trimethyl-2-cyclohexen-1-one stands for an isomer mixture of (5R,6S)-2,5,6-trimethylcyclohex-2-en-1-one and (5S,6R)-2,5,6-trimethylcyclohex-2-en-1-one (trans-IV).
2,5-cis-6-trimethyl-2-cyclohexen-1-one stands for an isomer mixture of (5R,6R)-2,5,6-trimethylcyclohex-2-en-1-one and (5S,6S)-2,5,6-trimethylcyclohex-2-en-1-one (cis-IV).

2, cis-5, cis-6-trimethyl-2-cyclohexen-1-ol stands for an isomer mixture of (1R,5R,6R)-2,5,6-trimethylcyclohex-2-en-1-ol and (1S,5S,6S)-2,5,6-trimethylcyclohex-2-en-1-ol.

2, trans-5, cis-6-trimethyl-2-cyclohexen-1-ol stands for an isomer mixture of (1R,5S,6R)-2,5,6-trimethylcyclohex-2-en-1-ol and (1S,5R,6S)-2,5,6-trimethylcyclohex-2-en-1-ol.

2, cis-5, trans-6-trimethyl-2-cyclohexen-1-ol stands for an isomer mixture of (1R,5R,6S)-2,5,6-trimethylcyclohex-2-en-1-ol and (1S,5S,6R)-2,5,6-trimethylcyclohex-2-en-1-ol.

2-(2, trans-4, cis-5-trimethyl-2-cyclohexen-1-yl)acetaldehyde stands for an isomer mixture of 2-((1R,4S,5R)-2,4,5-trimethylcyclohex-2-en-1-yl)acetaldehyde and 2-((1S,4R,5S)-2,4,5-trimethylcyclohex-2-en-1-yl)acetaldehyde.

Analytics:

The purity and identity of the products was determined by GC (area-%), $^1$H-NMR (CDCl$_3$, 500 MHz or 700 MHz) and/or $^{13}$C-NMR (CDCl$_3$, 125 MHz or 176 MHz).

NMR Method:

A DPX500US (Bruker) 500 MHz NMR spectrometer was used for all NMR measurements. About 20 mg of the material to be investigated was dissolved in about 700 μL CDCl$_3$. $^1$HNMR spectra (500 MHz, 700 MHz) and $^{13}$CNMR spectra (125 MHz, 176 MHz) were measured on a C/H—D—05 Z or a 5 mm CPTI 1H/19F—13C/15N/D ZGRD detection probe. Mnova 9.1 was used for evaluation of the spectra. If necessary, 2D-NMR experiments were performed.

GC-Method 1:
GC-system: Agilent 6890 N;
GC-Column: Agilent DB-17 (length: 30 m, ID: 0.25 mm, film: 0.25 micrometer), flow: 0.7 mL/min;
Temperature program: 50° C. to 150° C. at 15° C./min, 150C to 180° C. at 2° C./min, 180° C. to 300° C. at 10° C./min.
Characteristic GC-retention times (+/−0.2 min):
1,2-diethoxyethane: 3.8 min;
1-(1-isobutoxyethoxy)-2-methylpropane: 5.6 min;
2,5,6-trimethylcyclohex-2-en-1-ol isomers including 1,4,5-trimethyl-6-vinyloxy-cyclohexene
isomers: 7.4-7.9 min;
2,3,6-trimethylcyclohexan-1-ol isomers: 6.8-7.3 min;
2,5,6-trimethylcyclohex-2-en-1-one (cis-VI): 8.1 min;
2,5,6-trimethylcyclohex-2-en-1-one (trans-VI): 7.9 min;
2-(2,4,5-trimethylcyclohex-2-en-1-yl)acetaldehyde isomers: 9.2-10.4 min;
6-(1-ethoxyethoxy)-1,4,5-trimethyl-cyclohexene isomers: 9.8-10.2 min;
2-(2,4,5-trimethylcyclohex-2-en-1-yl)ethan-1-ol isomers: 10.3-11.1 min;
6-(1-isobutoxyethoxy)-1,4,5-trimethyl-cyclohexene isomers: 11.6-12.1 min;
2-(2,4,5-trimethylcyclohex-2-en-1-yl)ethyl acetate isomers: 12.1-13.5 min;
6-(2,2-diisobutoxyethyl)-1,3,4-trimethylcyclohex-1-ene: 18.2 min.

GC-Method 2:
GC-system: Shimadzu Nexis GC-2030;
GC-Column: Agilent DB-17 (length: 30 m, ID: 0.25 mm, film: 0.25 micrometer), flow: 1.2 mL/min;
Temperature program: 45° C. to 150° C. at 15° C./min, 150° C. to 180° C. at 2° C./min, 180 C to 300° C. at 10° C./min, 300° C. hold for 6 min.
Characteristic GC-retention times (+/−0.2 min):
6-(2-Methoxyethyl)-1,3,4-trimethylcyclohex-1-ene isomers: 5.6-6.0 min;
2-(2,4,5-trimethylcyclohex-2-en-1-yl)ethan-1-ol isomers: 6.5-6.8 min;
Methyl (2-(2,4,5-trimethylcyclohex-2-en-1-yl)ethyl) carbonate isomers: 8.9-9.4 min;
Ethyl (2-(2,4,5-trimethylcyclohex-2-en-1-yl)ethyl) carbonate 9.9-10.8 min.

HPL C-Method:
HPLC-System: Agilent Series 1290
HPLC-column: Ascentis Express RP-Amide, 2.7 μm, 150*4.6 mm von Supelco®
Eluent:
A: Water
B: Acetonitril/2-Propanol (1:1)

| Time [min.] | % B |
|---|---|
| 0.0 | 20 |
| 8.0 | 100 |
| 10.0 | 100 |
| 10.1 | 20 |

Detector: UV-detector λ=205 nm, BW=4 nm, flow-rate: 1.0 mL/min, injection: 5 μL,
Temperature: 40° C., run-time: 14 min., pressure: about 360 bar.
Characteristic HPLC-retention times (+/−0.2 min):
2,5,6-trimethylcyclohex-2-en-1-one (cis-VI): 4.7 min;
2,5,6-trimethylcyclohex-2-en-1-one (trans-VI): 5.0 min;
2,5,6-trimethylcyclohex-2-en-1-ol isomers: 5.1-5.3 min;
2,3,6-trimethylcyclohexan-1-ol isomers: 5.7 min;
2-(2,4,5-trimethylcyclohex-2-en-1-yl)ethyl acetate isomers: 5.7 min;
2-(2,4,5-trimethylcyclohex-2-en-1-yl)ethan-1-ol isomers: 6.1 min;
2-(2,4,5-trimethylcyclohex-2-en-1-yl)ethan-1-ol isomers: 6.1-6.2 min;
2-(2,4,5-trimethylcyclohex-2-en-1-yl)acetaldehyde isomers: 6.2-6.4 min;
Methyl (2-(2,4,5-trimethylcyclohex-2-en-1-yl)ethyl) carbonate isomers: 6.9 min;
2-(2,4,5-trimethylcyclohex-2-en-1-yl)ethyl acetate isomers: 7.0 min;
Ethyl (2-(2,4,5-trimethylcyclohex-2-en-1-yl)ethyl) carbonate isomers: 7.2 min;
6-(2-Methoxyethyl)-1,3,4-trimethylcyclohex-1-ene isomers: 7.2-7.4 min;
1,4,5-trimethyl-6-vinyloxy-cyclohexene isomers: 7.1-7.4 min;
6-(1-ethoxyethoxy)-1,4,5-trimethyl-cyclohexene isomers: 7.0-7.3 min;
6-(1-isobutoxyethoxy)-1,4,5-trimethyl-cyclohexene isomers: 8.0-8.1 min;
6-(2,2-diisobutoxyethyl)-1,3,4-trimethylcyclohex-1-ene: 8.9 min.

1. Preparation Examples 1.1 Preparation of 2,5,6-trimethylcyclohex-2-en-1-ol Using LiAlH$_4$ (Addition of LiAlH$_4$ in Portions):

50 g 2,5,6-trimethyl-2-cyclohexen-1-one (purity: 98 GC-a %; isomer distribution: 67 GC-a % 2,5-trans-6-trimethyl-2-cyclohexen-1-one (trans-IV), 31 GC-a % 2,5-cis-6-trimethyl-2-cyclohexen-1-one (cis-IV); comprising 1.2 GC-a % 2,3,6-trimethylcyclohexan-1-one; 0.35 mol, 1 eq) was dissolved in 445 g diethylether (0.5 L) and brought to 0° C. During 120 min 3.78 g LiAlH$_4$ (95%, 0.1 mol, 0.27 eq) was added in 10 portions. The reaction mixture was stirred for further 20 h at 0° C. Due to residual starting material further 0.34 g LiAlH$_4$ (95%, 0.009 mol, 0.03 eq) was added in 6 portions during 30 min. The reaction mixture was stirred for further 20 h at 0° C. 6.4 mL of dist. water was subsequently added in 30 min at a temperature of 0-5° C. 6.4 mL of 15% NaOH$_{(aq)}$ was added during 15 min. Further 19.2 mL of dist. water was added and the reaction mixture was stirred for 30 min. 50 g of Na$_2$SO$_4$ was added and the reaction mixture was stirred overnight. The reaction mixture was filtered using a 500 mL G3-suction filter. The filter cake was washed 2 times with 100 mL diethylether. The organic solvent of the filtrate was removed under reduced pressure at 50° C. and 750-4 mbar. 49.5 g of crude product was obtained as a white solid (99% yield) comprising 96.8 GC-a % of the title compound 2,5,6-trimethylcyclohex-2-en-1-ol and 1.7 GC-a % of 2,3,6-trimethylcyclohexan-1-ol. The identity of the product was confirmed by GC and $^1$H-NMR/$^{13}$C-NMR.

GC Retention Times:
2,5,6-trimethylcyclohex-2-en-1-ol isomers: 7.4-7.9 min;
2,3,6-trimethylcyclohexan-1-ol isomers: 6.8-7.3 min.

NMR Experiments Showed the Presence of 3 Major Tereoisomers.

2, cis-5, trans-6-trimethyl-2-cyclohexen-1-ol:
$^{13}$C-NMR (126 MHz, CDCl$_3$): δ=136.11, 123.88, 76.54, 44.30, 34.70, 34.22, 19.56, 19.39, 15.98.
$^1$H-NMR (500 MHz, CDCl$_3$): δ=5.44 (dd, J=4.3, 2.4 Hz, 1H), 3.59 (d, J=8.4 Hz, 1H), 2.03-1.59 (m, 5H), 1.39 (s, 1H), 1.27-1.15 (m, 1H), 1.07 (d, J=6.5 Hz, 3H), 0.93 (m, 3H).

2, cis-5, cis-6-trimethyl-2-cyclohexen-1-ol:
$^{13}$C-NMR (126 MHz, CDCl$_3$): δ=134.54, 122.93, 73.46, 38.65, 31.60, 30.48, 19.56, 18.63, 6.73.
$^1$H-NMR (500 MHz, CDCl$_3$): δ=5.41-5.33 (m, 1H), 4.19 (s, 1H), 1.97-1.65 (m, 7H), 0.99-0.87 (m, 3H), 0.83 (d, J=7.0 Hz, 3H).

2, trans-5, cis-6-trimethyl-2-cyclohexen-1-ol:
$^{13}$C-NMR (126 MHz, CDCl$_3$): δ=135.40, 125.14, 72.93, 40.46, 35.19, 27.85, 21.18, 18.93, 14.80.
$^1$H-NMR (500 MHz, CDCl$_3$): δ=5.52-5.47 (m, 1H), 3.69 (dd, J=7.1, 3.3 Hz, 1H), 2.12-1.46 (m, 6H), 1.39-1.31 (m, 1H), 1.04-1.01 (d, J=6.9 Hz, 3H), 0.96-0.88 (m, 3H).

Purity and Isomeric Distribution of the Product Obtained in Example 1.1:

| 2,3,6-trimethylcyclohexan-1-ol isomers [GC-a %] | | | | 2,5,6-trimethylcyclohex-2-en-1-ol isomers [GC-a %] | | | |
|---|---|---|---|---|---|---|---|
| 0.9 | 0.2 | 0.6 | Σ: 1.7 | 6.0 | 61.4 | 29.4 | Σ: 96.8 |

1.2 Preparation of 2,5,6-trimethylcyclohex-2-en-1-ol Using LiAlH$_4$ (Inverse Addition):

Towards 17 g LiAlH$_4$ (95%, 0.43 mol, 0.3 eq) in 1778 g diethylether (2 L) at −3° C. 200 g 2,5,6-trimethyl-2-cyclohexen-1-one (purity: 98 GC-a %; isomer distribution: 67 GC-a % 2,5-trans-6-trimethyl-2-cyclohexen-1-one (trans-IV), 31 GC-a % 2,5-cis-6-trimethyl-2-cyclohexen-1-one (cis-IV); comprising 1.2 GC-a % 2,5,6-trimethyl-cyclohexan-1-one; 1.42 mol, 1 eq) was added dropwise during 180 min at 0-4° C. The reaction mixture was stirred for further 20 h at 0° C. 16.4 mL of dist. water was subsequently added in 30 min at a temperature of 5-8° C. 16.4 mL of 15% NaOH$_{(aq)}$ were added during 15 min. Further 47.2 mL of dist. water were added and the reaction mixture was stirred for 30 min. 200 g of Na$_2$SO$_4$ was added and the reaction mixture was stirred for 2 h. The reaction mixture was filtered using a G3-suction filter. The filter cake was washed 2 times with 500 mL MTBE. The organic solvent of the filtrate was removed under reduced pressure at 60° C. and 750-5 mbar. 206.2 g of crude product was obtained as a white solid (95.2 GC-a % purity, 1.8 GC-a % MTBE, 99% yield) comprising 97.7 GC-a % of the title compound 2,5,6-trimethylcyclohex-2-en-1-ol and 1.3 GC-a % of 2,3,6-trimethylcyclohexanol (calculation without MTBE). The identity of the products was confirmed by GC and $^1$H-NMR/$^{13}$C-NMR.

Purity and Isomeric Distribution of the Product Obtained in Example 1.2:

| 2,3,6-trimethylcyclohexan-1-ol isomers [GC-a %] | | | | 2,5,6-trimethylcyclohex-2-en-1-ol isomers [GC-a %] | | | |
|---|---|---|---|---|---|---|---|
| 0.9 | 0.2 | 0.2 | Σ: 1.3 | — | 68.3 | 29.4 | Σ: 97.7 |

No separation of two 2,5,6-trimethylcyclohex-2-en-1-ol isomers via GC obtained, however via $^1$H-NMR/$^{13}$C-NMR in total 3 major isomers were confirmed (see example 1.1).

1.3 Preparation of 2,5,6-trimethylcyclohex-2-en-1-ol Using NaBH$_4$:

120 g 2,5,6-trimethyl-2-cyclohexen-1-one (purity: 98 GC-a %; isomer distribution: 67 GC-a % 2,5-trans-6-trimethyl-2-cyclohexen-1-one, 31 GC-a % 2,5-cis-6-trimethyl-2-cyclohexen-1-one; comprising 1.2 GC-a % 2,5,6-trimethyl-cyclohexan-1-one; 0.85 mol, 1 eq) was dissolved in 948 g methanol (1.2 L) and brought to 0-5° C. During 120 min 35.66 g NaBH$_4$ (99%, 0.93 mol, 1.1 eq) was added in 12 portions. The reaction mixture was stirred for further 120 min at 2-8° C. 750 mL of dist. water was subsequently added in 5 min at a temperature of 0-15° C. The reaction mixture was stirred for further 30 min and after addition of 1.5 L MTBE the phases were separated. The aqueous phase was further extracted using 450 mL MTBE. The organic phases were combined, washed 2 times with 200 mL of sat. sodium chloride solution, dried over Na$_2$SO$_4$ and the solvent was removed under reduced pressure at 40° C., 250-5 mbar. 107 g of crude product was obtained as a white solid (89% yield) comprising 89.6 GC-a % of the title compound 2,5,6-trimethylcyclohex-2-en-1-ol and 9.4 GC-a % of 2,3,6-trimethylcyclohexanol. The identity of the products was confirmed by GC and $^1$H-NMR/$^{13}$C-NMR.

Purity and Isomeric Distribution of the Product Obtained in Example 1.3:

| 2,3,6-trimethylcyclohexan-1-ol isomers [GC-a %] | | | | 2,5,6-trimethylcyclohex-2-en-1-ol isomers [GC-a %] | | | |
|---|---|---|---|---|---|---|---|
| 6.8 | 1.6 | 1.0 | Σ: 9.4 | 20 | 45 | 24 | Σ: 89.6 |

1.4 Preparation of 2-(2,4,5-trimethylcyclohex-2-en-1-yl)acetaldehyde Using Isobutylvinylether in the Presence of Phosphoric Acid:

80 g 2,5,6-trimethyl-2-cyclohexen-1-ol (97 GC-a %, 0.55 mol, 1 eq) was dissolved in 121.9 g isobutylvinylether (158 mL, 1.22 mol, 2.2 eq). 0.32 g phosphoric acid (85%, 0.17 mL, 2.8 mmol, 0.005 eq) was added at 20° C. The reaction mixture was brought to 3 bar nitrogen pressure and 150° C. and stirred for 5 h at 5.3-5.0 bar. The reaction mixture was brought to room temperature and 800 mL of cyclohexane was added. The organic phase was washed with 75 mL of 5% NaHCO$_{3(aq)}$. The organic phase was dried over Na$_2$SO$_4$ and filtered over silica gel. The filter cake was washed two times with 300 mL of cyclohexane each. The solvent was removed under reduced pressure at 60° C., 110-5 mbar. 104.6 g of crude 2-(2,4,5-trimethylcyclohex-2-en-1-yl)acetaldehyde was obtained as a yellow liquid (47 GC-a % purity, 53% yield based on GC-a %). A major byproduct is the acetal compound 1-(1-isobutoxyethoxy)-2-methylpropane with 18 GC-a %. Furthermore, 15-20 GC-a % of acetal isomers 6-(1-isobutoxyethoxy)-1,4,5-trimethylcyclohex-1-ene, which are formed as intermediates, are found in the crude product and could be further converted to the product.

A by-product, which can be found in the crude product if the reaction is conducted for more than 5 hours is 6-(2,2-diisobutoxyethyl)-1,3,4-trimethyl-cyclohexene.

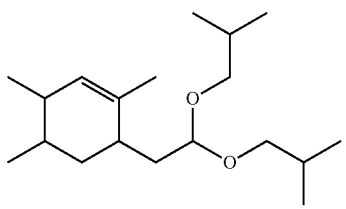 [SMILES: CC1=CC(C)C(C)CC1CC(OCC(C)C)OCC(C)C]

Also this by-product could be further converted to the desired title compound.

The identity of the products was confirmed by GC and $^1$H-NMR/$^{13}$C-NMR.

NMR data of the major stereoisomer 2-(2, trans-4, cis-5-trimethylcyclohex-2-en-1-yl-)acetaldehyde:

$^1$H-NMR (CDCl$_3$, 500 MHz): δ=9.77 (d, J=1.9 Hz, 1H), 5.25 (s, 1H), 2.74-2.58 (m, 2H), 2.36-2.22 (m, 1H), 1.79 (m, 1H), 1.75-1.58 (m, 4H), 1.21 (m, 1H), 1.18-1.01 (m, 1H), 1.05-0.88 (m, 6H).

$^{13}$C-NMR (126 MHz, CDCl$_3$): δ=203.16, 133.32, 131.45, 47.70, 39.56, 38.07, 36.16, 35.10, 21.28, 19.96, 19.91.

1.5 Purification of 2-(2,4,5-trimethylcyclohex-2-en-1-yl)acetaldehyde

The crude 2-(2,4,5-trimethylcyclohex-2-en-1-yl)acetaldehyde obtained in example 1.3 was subjected to fractionated distillation at T$_{bath}$ 124-135° C., T$_{in}$ 103-117° C., T$_{head}$ 78° C., 7-8 mbar, using a 40 cm column filled with V4A, Normag. 2-(2,4,5-trimethylcyclohex-2-en-1-yl)acetaldehyde could be obtained in a purity of >96 GC-a % as colorless to slight yellow liquid.

Using a Pilodist HRS 500 C (semi-micro distillation system with concentric tube column) at T$_{bath}$ 108-119° C., T$_{in}$ 93-98° C., T$_{mantle}$=65-67, T$_{head}$ 69-71° C., 3 mbar 2-(2,4,5-trimethylcyclohex-2-en-1-yl)acetaldehyde could be obtained in a purity of >98 GC-a % as colorless liquid.

1.6 Preparation of 2-(2,4,5-trimethylcyclohex-2-en-1-yl)acetaldehyde Using Ethylvinyl Ether in the Presence of Phosphoric Acid:

The reaction was performed as described in example 1.4, except that ethylvinylether was used instead of isobutylvinylether. After workup, 85 g of crude 2-(2,4,5-trimethylcyclohex-2-en-1-yl)acetaldehyde was obtained (57.7 HPLC-a % purity, 54% yield based on HPLC-a %). 15 HPLC-a % of the 6-(1-ethoxyethoxy)-1,4,5-trimethyl-cyclohexene isomers are found in the crude product.

1.7 Preparation of 6-(1-ethoxyethoxy)-1,4,5-trimethylcyclohex-1-ene:

50 g 2,5,6-trimethyl-2-cyclohexen-1-ol (96 GC-a %, 0.34 mol, 1 eq) was dissolved in 54.87 g ethylvinylether (73.16 mL, 0.76 mol, 2.2 eq). 0.4 g phosphoric acid (85%, 0.21 mL, 3.5 mmol, 0.01 eq) was added at 20° C. The reaction mixture was heated to 45° C. and stirred for 18 h. 750 mL of cyclohexane was added to the reaction mixture. The organic phase was washed two times with 50 mL of 5% NaHCO$_{3(aq)}$ each. The organic phase was dried over Na$_2$SO$_4$. The solvent was removed under reduced pressure at 50° C., 150-4 mbar. 74.8 g of crude product 6-(1-ethoxyethoxy)-1,4,5-trimethylcyclohex-1-ene was obtained as colorless liquid with 86 GC-a % purity and 89% yield.

After column chromatography (silica gel, n-hexane: ethyl acetate 20:1), the product 6-(1-ethoxyethoxy)-1,4,5-trimethyl-cyclohex-1-ene was obtained in a purity of 95 HPLC-a %.

The identity of the products was confirmed by GC and $^1$H-/$^{13}$C- and 2D-NMR.

NMR data of the major stereoisomers:

Isomer 1:
$^1$H-NMR (700 MHz, CDCl$_3$): δ=5.49-5.43 (m, 1H), 4.79-4.75 (m, 1H), 3.74-3.50 (m, 3H), 2.09-1.58 (m, 6H), 1.52-1.39 (m, 1H), 1.37-1.29 (m, 3H), 1.25-1.15 (m, 3H), 0.99 (d, J=6.8 Hz, 3H), 0.98-0.97 (m, 3H).
$^{13}$C-NMR (176 MHz, CDCl$_3$): δ=133.92, 124.71, 99.61, 81.56, 60.04, 40.83, 33.24, 32.89, 21.0-19.5, 21.0-19.5, 21.0-19.5, 16.70, 15.43.

Isomer 2:
$^1$H-NMR (700 MHz, CDCl$_3$): δ=5.49-5.43 (m, 1H), 4.77 (m, 1H), 3.74-3.47 (m, 3H), 2.09-1.54 (m, 5H), 1.48 (m, 2H), 1.39-1.29 (m, 3H), 1.25-1.17 (m, 3H), 1.07 (d, J=6.1 Hz, 3H), 0.98-0.95 (m, 3H).
$^{13}$C-NMR (176 MHz, CDCl$_3$): δ=134.58, 124.72, 101.41, 82.16, 60.93, 41.48, 33.88, 33.48, 21.0-19.5, 21.0-19.5, 21.0-19.5, 16.43, 15.38.

Isomer 3:
$^1$H-NMR (700 MHz, CDCl$_3$): δ=5.39 (m, 1H), 4.84 (q, J=5.5 Hz, 1H), 4.27 (m, 1H), 3.74-3.45 (m, 2H), 2.08-1.63 (m, 7H), 1.38-1.30 (m, 3H), 1.24-1.14 (m, 3H), 0.93 (m, 3H), 0.75 (d, J=6.9 Hz, 3H).
$^{13}$C-NMR (176 MHz, CDCl$_3$): δ=133.84, 123.23, 96.79, 76.72, 58.89, 35.35, 31.39, 29.79, 21.0-19.5, 21.0-19.5, 19.22, 15.47, 5.93.

Isomer 4:
$^1$H-NMR (700 MHz, CDCl$_3$): δ=5.36 (m, 1H), 4.78-4.74 (m, 1H), 4.09 (m, 1H), 3.67-3.51 (m, 2H), 2.08-1.65 (m, 7H), 1.38-1.30 (m, 3H), 1.25-1.14 (m, 3H), 0.93 (dd, J=6.7, 4.3 Hz, 3H), 0.83 (d, J=6.9 Hz, 3H).
$^{13}$C-NMR (176 MHz, CDCl$_3$): δ=134.15, 123.23, 101.41, 80.07, 59.62, 37.83, 31.77, 29.83, 21.0-19.5, 21.0-19.5, 19.16, 15.47, 6.16.

1.8 Preparation of 2-(2,4,5-trimethylcyclohex-2-en-1-yl)ethan-1-ol:

6.5 g 2-(2,4,5-trimethylcyclohex-2-en-1-yl)acetaldehyde (97.0 GC-a %, 38 mmol, 1 eq) was dissolved in 51.4 g methanol (65 mL, 1.6 mol, 43 eq) and cooled to 0-5° C. 2.7 g sodium borohydride (71 mmol, 1.9 eq) was added in portions keeping the temperature between 0-8° C. The reaction mixture was stirred for further 2 h at 2-8° C.

40 mL of water was added to the reaction mixture at a temperature of 0-15° C. during 5 min. The reaction mixture was stirred for further 30 min and afterwards extracted using 80 mL of methyl-tert-butylether (MTBE). The phases were separated and the aqueous phase was extracted with further 25 mL MTBE. The organic phases were combined, washed two times with 10 mL of sat. NaCl solution and dried over Na$_2$SO$_4$. The solvent was removed under reduced pressure at 40° C., 250-5 mbar. 6.3 g of crude product 2-(2,4,5-trimethylcyclohex-2-en-1-yl)ethan-1-ol was obtained as colorless liquid with 90.4 HPLC-a % purity and 89% yield.

After column chromatography (silica gel, cyclohexane: ethyl acetate 20:1), the product 2-(2,4,5-trimethylcyclohex-2-en-1-yl)ethan-1-ol was obtained in a purity of 99.4 HPLC-a %.

The identity of the major stereoisomer was confirmed by HPLC and $^1$H-/$^{13}$C-NMR.

NMR data of the major stereoisomer 2-(2, trans-4, cis-5-trimethylcyclohex-2-en-1-yl)ethan-1-ol:
$^1$H NMR (500 MHz, CDCl$_3$): δ=5.19 (s, 1H), 3.81-3.56 (m, 2H), 2.21 (s, 1H), 1.97 (m, 1H), 1.76 (m, 1H), 1.67 (s, 4H), 1.45-1.33 (m, 1H), 1.14 (m, 1H), 1.05-0.88 (m, 7H).
$^{13}$C NMR (126 MHz, CDCl$_3$): δ=135.41, 130.25, 60.74, 38.59, 37.99, 36.56, 36.21, 36.10, 21.22, 20.08, 20.07.

1.9 Preparation of 2-(2,4,5-trimethylcyclohex-2-en-1-yl) ethyl Acetate:

5 g 2-(2,4,5-trimethylcyclohex-2-en-1-yl)ethan-1-ol (97.8 GC-a %, 29 mmol, 1 eq) was dissolved in 43.5 g toluene (50 mL, 443 mmol, 15.3 eq) and 1.61 g pyridine (1.64 mL, 20 mmol, 0.7 eq) were added. Subsequently, 3.19 g acetyl chloride (2.9 mL, 41 mmol, 1.4 eq) were added at room temperature during 60 min. After stirring for 18 h at room temperature 50 mL of water were added and the phases were separated. The organic phase was extracted once with 50 mL water. The phases were separated. The organic phase was dried using over Na$_2$SO$_4$. The solvent was removed under reduced pressure at 50-60° C. and 200-5 mbar. 5 g of crude product 2-(2,4,5-trimethylcyclohex-2-en-1-yl)ethyl acetate was obtained as colorless liquid with 98.3 GC-a % purity and 80% yield.

The identity of the major stereoisomer was confirmed by GC and $^1$H-/$^{13}$C-NMR.

NMR data of the major stereoisomer 2-(2, trans-4, cis-5-trimethylcyclohex-2-en-1-yl)ethyl acetate:
$^1$H NMR (500 MHz, CDCl$_3$): δ=5.20 (s, 1H), 4.22-4.00 (m, 2H), 2.30-2.13 (m, 1H), 2.10-1.95 (m, 4H), 1.75 (ddd, J=12.7, 5.5, 2.5 Hz, 1H), 1.65 (s, 4H), 1.53-1.38 (m, 1H), 1.20-1.08 (m, 1H), 1.07-0.96 (m, 1H), 0.95 (m, 6H).
$^{13}$C NMR (126 MHz, CDCl$_3$): δ=171.13, 134.69, 130.64, 62.64, 38.43, 37.97, 36.72, 36.18, 31.89, 21.12, 21.03, 20.05, 20.04.

1.10 Preparation of Methyl (2-(2,4,5-trimethylcyclohex-2-en-1-yl)ethyl) Carbonate:

2.8 g 2-(2,4,5-trimethylcyclohex-2-en-1-yl)ethan-1-ol (97 GC-a %, 16 mmol, 1 eq) was dissolved in 36.4 g dimethylcarbonate (37 mL, 400 mmol, 25 eq). Subsequently, 2.9 g potassium carbonate (21 mmol, 1.3 eq) were added. The suspension was heated to reflux and stirred for 8 h. During the reaction, distillate is removed. Overnight, the reaction was run at complete reflux. After further 1 h stirring and removing of distillate, the reaction mixture was brought to 50° C. and filtered. The filter cake is washed two times with 25 mL of dimethylcarbonate each. The solvent of the filtrate was removed under reduced pressure at 60° C. and 75-3 mbar. 3.3 g of crude product methyl (2-(2,4,5-trimethylcyclohex-2-en-1-yl)ethyl) carbonate was obtained with 93.3 GC-a % purity and 84% yield.

The crude product was distilled using a "Kugelrohr" apparatus at 115-120° C. and 0.2 mbar. 2.6 g of methyl (2-(2,4,5-trimethylcyclohex-2-en-1-yl)ethyl) carbonate was obtained as colorless liquid with 96.7 GC-a % purity and residual 1.1 GC-a % of 2-(2,4,5-trimethylcyclohex-2-en-1-yl)ethan-1-ol.

The identity of the major stereoisomer was confirmed by GC and $^1$H-/$^{13}$C-NMR.

NMR data of the major stereoisomer methyl (2-(2, trans-4, cis-5-trimethylcyclohex-2-en-1-yl)ethyl) carbonate:
$^1$H NMR (500 MHz, CDCl$_3$): δ=5.20 (s, 1H), 4.18 (m, 2H), 3.77 (s, 3H), 2.35-2.13 (m, 1H), 2.08 (m, 1H), 1.77 (ddd, J=12.7, 5.5, 2.5 Hz, 1H), 1.65 (s, 4H), 1.48 (m, 1H), 1.14 (m, 1H), 1.02 (q, J=12.2 Hz, 1H), 0.95 (m, 6H).
$^{13}$C NMR (126 MHz, CDCl$_3$): δ=155.86, 134.54, 130.74, 66.22, 54.63, 38.40, 37.97, 36.46, 36.16, 31.98, 21.08, 20.05, 20.03.

1.11 Preparation of Ethyl (2-(2,4,5-trimethylcyclohex-2-en-1-yl)ethyl) Carbonate:

4.5 g 2-(2,4,5-trimethylcyclohex-2-en-1-yl)ethan-1-ol (98.6 GC-a %, 26 mmol, 1 eq) was dissolved in 77.2 g diethylcarbonate (78.8 mL, 654 mmol, 25 eq). Subsequently, 4.7 g potassium carbonate (34 mmol, 1.3 eq) were added. The suspension was heated to reflux and stirred for 8 h. During the reaction, distillate is removed. Overnight, the reaction was run at complete reflux. After further 1 h stirring and removing of distillate, the reaction mixture was brought to 50° C. and filtered. The filter cake is washed two times with 25 mL of diethylcarbonate each. The solvent of the filtrate was removed under reduced pressure at 60° C. and 75-3 mbar. 5.5 g of crude product ethyl (2-(2,4,5-trimethylcyclohex-2-en-1-yl)ethyl) carbonate was obtained with 93.2 HPLC-a % purity and 81% yield.

The crude product was distilled using a "Kugelrohr" apparatus at 80-85° C. and 0.3-0.15 mbar. 4.3 g of ethyl (2-(2,4,5-trimethylcyclohex-2-en-1-yl)ethyl) carbonate was obtained as colorless liquid with 97 HPLC-a % purity.

The identity of the major stereoisomer was confirmed by HPLC and $^1$H-/$^{13}$C-NMR.

NMR data of the major stereoisomer ethyl (2-(2, trans-4, cis-5-trimethylcyclohex-2-en1-yl)ethyl) carbonate:
$^1$H NMR (500 MHz, CDCl$_3$): δ=5.20 (s, 1H), 4.30-4.07 (m, 4H), 2.31-2.19 (m, 1H), 2.09-2.04 (m, 1H), 1.77 (ddd, J=12.7, 5.5, 2.6 Hz, 1H), 1.65 (s, 4H), 1.54-1.40 (m, 1H), 1.31 (t, J=7.2 Hz, 3H), 1.21 (m, 1H), 1.09-0.97 (m, 1H), 0.95 (m, 6H).
$^{13}$C NMR (126 MHz, CDCl$_3$): δ=155.25, 134.59, 130.70, 65.99, 63.84, 38.39, 37.96, 36.44, 36.14, 31.99, 21.08, 20.04, 20.02, 14.30.

1.12 Preparation of 6-(2-methoxyethyl)-1,3,4-trimethylcyclohex-1-ene:

1.11 g sodium (46.2 mmol, 1.65 eq) in 80 g xylenes and 0.1 g of diethylenegylcolmonomethylether (0.1 mL, 0.8 mmol, 0.03 eq) were brought to 110° C. During 3 h 5 g 2-(2,4,5-trimethylcyclohex-2-en-1-yl)ethan-1-ol (94.6 GC-a %, 28 mmol, 1 eq) in 20 g of xylenes was added dropwise at 113-118° C. and stirred overnight at 113° C. Then, the reaction mixture was brought to 131° C. and stirred at 800 rpm. 2.39 g dimethylsulfate (1.8 mL, 18.9 mmol, 0.68 eq) was added at 131-134° C. during 2 h. The reaction mixture was stirred at 250 rpm for 4 h at 130° C. and at room temperature over the weekend.

Subsequently, the reaction mixture was added towards 30 g of dist. water, brought to 80° C. and stirred for 4 h. Then, the reaction mixture was brought to 50° C., and the phases were separated. The aqueous phase was extracted once using 50 mL xylenes. The organic phase was dried using sodium sulfate and filtered. The solvent was removed at 50° C. and 40-15 mbar. 5.6 g of crude product 6-(2-methoxyethyl)-1,3,4-trimethylcyclohex-1-ene was obtained with 76 GC-a % purity and 84% yield. Further 18 GC-a % of unreacted starting material 2-(2,4,5-trimethylcyclohex-2-en-1-yl)ethan-1-ol were recovered.

The crude product was distilled using a "Kugelrohr" apparatus at 55-65° C. and 0.05 mbar. 2.7 g of 6-(2-Methoxyethyl)-1,3,4-trimethylcyclohex-1-ene was obtained as colorless liquid with 95.2 GC-a % purity—containing 2 GC-a % of starting material 2-(2,4,5-trimethylcyclohex-2-en-1-yl)ethan-1-ol.

The identity of the major stereoisomer was confirmed by GC and $^1$H-/$^{13}$C-NMR.

NMR data of the major stereoisomer 6-(2-methoxyethyl)-1,3,4-trimethylcyclohex-1-ene:

$^1$H NMR (500 MHz, CDCl$_3$): δ=5.17 (s, 1H), 3.44-3.38 (m, 2H), 3.33 (s, 3H), 2.27-2.11 (m, 1H), 2.07-1.95 (m, 1H), 1.75 (ddd, J=12.7, 5.5, 2.6 Hz, 1H), 1.65 (s, 4H), 1.41-1.27 (m, 1H), 1.13 (m, J=1H), 1.04-0.97 (m, 1H), 0.94 (dd, J=6.9, 4.0 Hz, 6H).

$^{13}$C NMR (126 MHz, CDCl$_3$): δ=135.43, 130.16, 70.70, 58.59, 38.69, 38.06, 36.77, 36.26, 33.02, 21.17, 20.11, 20.10.

1.13 Preparation of 6-(2-ethoxyethyl)-1,3,4-trimethylcyclohex-1-ene:

1.05 g of sodium (43.8 mmol, 1.65 eq) in 100 g xylenes and 0.1 g of diethylenegylcolmonomethylether (0.1 mL, 0.8 mmol, 0.03 eq) were brought to 110° C. During 3 h 4.5 g 2-(2,4,5-trimethylcyclohex-2-en-1-yl)ethan-1-ol (99.5 GC-a %, 26.6 mmol, 1 eq) in 20 g of xylenes were added dropwise at 113-118° C. and stirred overnight at 113° C. Then, the reaction mixture was brought to 131° C. and stirred at 800 rpm. 2.54 g of diethylsulfate (1.91 mL, 18.1 mmol, 0.68 eq) were added at 131-134° C. during 2 h. The reaction mixture was stirred at 250 rpm for 4 h at 130° C. and at room temperature over the weekend.

Subsequently, the reaction mixture was added to 30 g of dist. water, brought to 80° C. and stirred for 4 h. Then, the reaction mixture was brought to 50° C., and the phases were separated. The aqueous phase was extracted once using 50 mL xylenes. The organic phase was dried using sodium sulfate and filtered. The solvent was removed at 50° C. and 40-15 mbar. 4.9 g of crude product 6-(2-ethoxyethyl)-1,3,4-trimethylcyclohex-1-ene was obtained with 68 GC-a % purity and 64% yield. Further 28 GC-a % of unreacted starting material 2-(2,4,5-trimethylcyclohex-2-en-1-yl)ethan-1-ol were recovered.

The crude product was distilled using a "Kugelrohr" apparatus at 55-65° C. and 0.05 mbar. 1 g of 6-(2-ethoxyethyl)-1,3,4-trimethylcyclohex-1-ene was obtained as colorless liquid with 97.7 GC-a % purity—containing 1.3 GC-a % of starting material 2-(2,4,5-trimethylcyclohex-2-en-1-yl)ethan-1-ol.

The identity of the major stereoisomer was confirmed by GC and $^1$H-/$^{13}$C-NMR.

NMR data of the major stereoisomer 6-(2-ethoxyethyl)-1,3,4-trimethylcyclohex-1-ene:

$^1$H NMR (500 MHz, CDCl$_3$): δ=5.17 (s, 1H), 3.57-3.38 (m, 4H), 2.25-2.13 (s, 1H), 2.07-1.96 (m, 1H), 1.78-1.70 (m, 1H), 1.66 (s, 4H), 1.44-1.32 (m, 1H), 1.21 (t, J=7.0 Hz, 3H), 1.17-1.08 (m, 1H), 1.05-0.90 (m, 7H).

$^{13}$C NMR (126 MHz, CDCl$_3$): δ=135.54, 130.09, 68.64, 66.18, 38.71, 38.03, 36.89, 36.26, 33.14, 21.20, 20.11, 20.10, 15.28.

2. Olfactory Assessment

In order to test the quality and intensity of the odor of the compounds (I), (II), (III) and (IV) of the present invention, scent strip tests were performed.

For this purpose, strips of absorbent paper were dipped into solution containing 0.01 to 10% by weight solutions of the compound (I), (II), (III) or (IV) or mixtures thereof. The solutions were prepared by using triethylcitrate including 250 ppm tocopherol as solvent. Typically, 10% by weight stock-solutions of the compound (I), (II), (III) or (IV), or mixtures thereof, in triethylcitrate including 250 ppm tocopherol were prepared, unless otherwise stated. For the preparation of the higher diluted solutions, ethanol was typically used as further solvent. The scent impression was olfactively evaluated by a panel of 4 trained perfumer using freshly dipped blotter paper.

The results of the scent test are summarized in table 1.

TABLE 1

Results of the scent tests

| Example no. | Compound | Description |
|---|---|---|
| 1.1-a | OH (Mixture of stereoisomers, Purity: 96.8 GC-a %) | 10% solution Animalic, indole, technical, solvent, pungent, phenolic |
| 1.1-b | OH (Mixture of stereoisomers, Purity: 96.8 GC-a %) | 100 ppm solution Phenolic, green banana, nutty, milky and/or warm |

TABLE 1-continued

Results of the scent tests

| Example no. | Compound | Description |
|---|---|---|
| 1.5 | 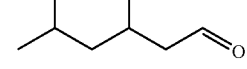<br>Mixture of stereoisomers<br>Purity: >98 GC-a % | Green, watery, chrysanthema, grassy, aldehydic, lily of the valley, leathery, terpenic and/or natural |
| 1.7 | 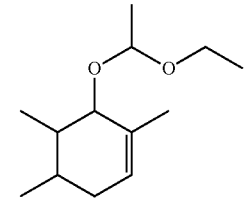<br>Mixture of stereoisomers<br>Purity: 95 HPLC-a % | Watermelon, watery, green, almond, foodlike, technical |
| 1.8 | 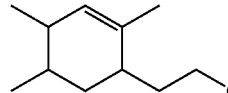<br>Mixture of stereoisomers<br>Purity: 99.4 HPLC-a % | Crysantheme, green, herbal, dusty, diesel |
| 1.9 | 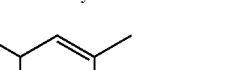<br>Mixture of stereoisomers<br>Purity: 98.3 HPLC-a % | Floral, muguet |
| 1.12 | 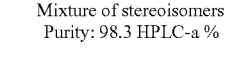<br>Mixture of stereoisomers<br>Purity: 95.2 GC-a % - containing 2 GC-a % 2-(2,4,5-trimethylcyclohex-2-en-1-yl)ethan-1-ol. | Moldy, sweet, leathery, agrumic, fresh, nutmeg |
| 1.13 | 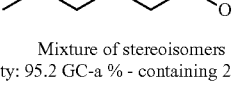<br>Mixture of stereoisomers<br>Purity: 97.7 GC-a % purity - containing 1.3 GC-a % of 2-(2,4,5-trimethylcyclohex-2-en-1-yl)ethan-1-ol | Fruity |

Sales Products and Advantageous Fragrance Compositions

Solution A is a 10% by weight solution of 2,5,6-trimethylcyclohex-2-en-1-ol, obtained from example 1.1, in triethylcitrate additionally comprising 0.025% by weight (250 ppm) tocopherol.

Solution B is 2-(2,4,5-trimethylcyclohex-2-en-1-yl)acetaldehyde obtained from example 1.5.

Solution C is 6-(1-ethoxyethoxy)-1,4,5-trimethyl-cyclohex-1-ene obtained from example 1.7.

Solution D is 2-(2,4,5-trimethylcyclohex-2-en-1-yl) ethan-1-ol obtained from example 1.8.

Solution E is 2-(2,4,5-trimethylcyclohex-2-en-1-yl)ethyl acetate, obtained from example 1.9.

Solution F is 6-(2-methoxyethyl)-1,3,4-trimethylcyclohex-1-ene obtained from example 1.12.

Solution G is 6-(2-ethoxyethyl)-1,3,4-trimethylcyclohex-1-ene obtained from example 1.13.

Advantageous Fragrance Compositions:

Solution A as described above was formulated in the compositions according to table 2. The amounts given in table 2 are weight units in grams.

TABLE 2

| Fragrance compositions 1A and 1B | | |
|---|---|---|
| | 1A | 1B |
| Lactone C10 gamma (5-hexyloxolan-2-one) | 2 | 2 |
| Bourgeonal (3-(4-tert-butylphenyl)propanal) | 2 | 2 |
| Citronellol | 3 | 3 |
| Aldehyde C-14 (5-heptyloxolan-2-one) | 3 | 3 |
| Allyl heptylate | 4 | 4 |
| Amber core (1-(2-tert-butylcyclohexyl)oxybutan-2-ol) | 4 | 4 |
| Ethyl-2-methyl butyrate | 4 | 4 |
| Geranyl acetate | 5 | 5 |
| Helional (3-(1,3-benzodioxol-5-yl)-2-methylpropanal) | 10 | 10 |
| Manzanate (ethyl 2-methylpentanoate) | 10 | 10 |
| Amberwood (ethoxymethoxycyclododecane) | 10 | 10 |
| Hexyl acetate | 11 | 11 |
| Benzyl salicylate | 12 | 12 |
| Magnolan (2,4-dimethyl-4,4a,5,9b-tetrahydroindeno[1,2-d][1,3]dioxine) | 15 | 15 |
| Verdox (2-tert-butylcyclohexyl) acetate) | 25 | 25 |
| Bergamot oil bergaptene free | 25 | 25 |
| Linalol | 30 | 30 |
| Dipropylene glycol | 45 | 45 |
| Iso E Super (Tetramethyl acetyloctahydronaphthalenes) | 110 | 110 |
| Pyranol (4-methyl-2-(2-methylpropyl)oxan-4-ol) | 170 | 170 |
| Hedione (methyl 3-oxo-2-pentylcyclopentaneacetate) | 200 | 200 |
| Galaxolide 50% IPM (1,3,4,6,7,8-hexahydro-4,6,6,7,8,8-hexamethylcyclopenta(g)-2-benzopyran 50% in isopropyl myristate) | 300 | 300 |
| Solution A | 25 | 50 |
| | 1025 | 1050 |

Solution B as described above was formulated in the compositions according to table 3. The amounts given in table 3 are weight units in grams.

TABLE 3

| Fragrance compositions 2A and 2B | | |
|---|---|---|
| | 2A | 2B |
| Raspberry ketone (4-(4-hydroxyphenyl)butan-2-one) | 4 | 4 |
| Vanitrope (2-ethoxy-5-prop-1-enylphenol) | 6 | 6 |
| Cyclamen aldehyde (at least 90% 2-methyl-3-(p-isopropylphenyl)-propionaldehyde; secondary component: 5% 3-(p-cumenyl)-2-methylpropionic acid) | 10 | 10 |
| Bicyclononalactone (3,4,4a,5,6,7,8,8a-octahydrochromen-2-one) | 10 | 10 |
| Aldehyde C-14 (5-heptyloxolan-2-one) | 14 | 14 |
| Ethylvanillin (3-ethoxy-4-hydroxybenzaldehyde) | 16 | 16 |
| Heliotropine (1,3-benzodioxole-5-carbaldehyde) | 20 | 20 |
| Iso E Super (tetramethyl acetyloctahydronaphthalenes) | 20 | 20 |
| Sandela (3-[5,5,6-trimethylbicyclo[2.2.1]hept-2-yl]cyclohexan-1-ol) | 30 | 30 |
| Vanillin isobutyrate ((4-formyl-2-methoxyphenyl) 2-methylpropanoate) | 40 | 40 |
| Aldehyde C-18 (5-pentyloxolan-2-one) | 50 | 50 |
| Benzyl salicylate | 60 | 60 |
| Hexyl cinnamic aldehyde (2-(phenylmethylidene)octanal) | 70 | 70 |
| Hedione (methyl 3-oxo-2-pentylcyclopentaneacetate) | 130 | 130 |
| Pyranol (4-methyl-2-(2-methylpropyl)oxan-4-ol) | 150 | 150 |
| Ethylene brassylate (1,4-dioxacycloheptadecane-5,17-dione) | 170 | 170 |
| Galaxolide 50% IPM (1,3,4,6,7,8-hexahydro-4,6,6,7,8,8-hexamethylcyclopenta(g)-2-benzopyran 50% in isopropyl myristate) | 200 | 200 |
| Solution B | 10 | 20 |
| | 1010 | 1020 |

Fragrance composition 3 corresponds to fragrance composition 1A, where Solution A is replaced by the same amount of Solution C. Fragrance composition 4 corresponds to fragrance composition 1B, where Solution A is replaced by the same amount of Solution D. Fragrance composition 5 corresponds to fragrance composition 2A, where Solution B is replaced by the same amount of Solution E. Fragrance composition 6 corresponds to fragrance composition 2B, where Solution B is replaced by the same amount of Solution F. Fragrance composition 7 corresponds to fragrance composition 2B, where Solution B is replaced by the same amount of Solution G.

The invention claimed is:

1. A compound of the general formula (I)

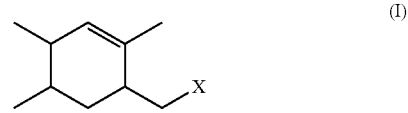

(I)

wherein

X represents a group of the formulae $X_1$ to $X_4$

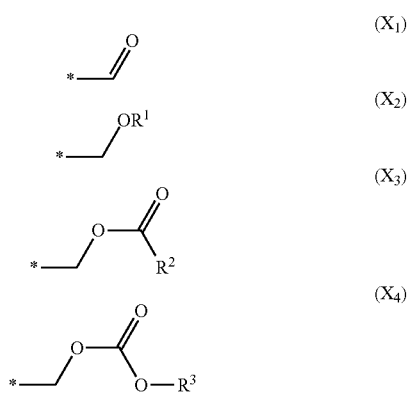

wherein the asterisk denotes the point of attachment to the rest of the molecule, and $R^1$ and $R^2$ are, independently of each other, selected from hydrogen, methyl and ethyl, and $R^3$ is selected from hydrogen, methyl, ethyl and phenyl, a mixture thereof, a stereoisomer thereof or a mixture of stereoisomers thereof.

2. The compound according to claim 1, where the compounds of formula (I) have at least one of the following features a) to c)
   a) $R^1$ is hydrogen or methyl,
   b) $R^2$ and $R^3$, independently of each other, are methyl or ethyl,
   c) X represents a group $X_1$, $X_2$ or $X_3$.

3. The compound according to claim 1, where X represents a group $X_1$, $X_2$ or $X_3$.

4. The compound according to claim 3, where in $X_2R^1$ is hydrogen, methyl or ethyl and in $X_3R^2$ is methyl or ethyl.

5. The compounds according to claim 1, comprising at most 1% by weight of 2,5,6-trimethylcyclohex-2-en-1-one and at most 1% by weight of 2,5,6-trimethylcyclohex-2-en-1-ol, based on the total weight of the compounds or of the mixture of compounds.

6. A process for preparing a compound of the general formula (I), or a mixture of two or more compounds of the general formula (I) or a stereoisomer thereof or a mixture of two or more stereoisomers thereof, according to claim 1, which process comprises:
   (i) providing 2,5,6-trimethylcyclohex-2-en-1-ol (IV),

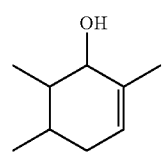

(IV)

(ii) reacting 2,5,6-trimethylcyclohex-2-en-1-ol (IV) provided in step (i) with a vinylether of the general formula (V)

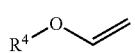

(V)

wherein
   $R^4$ is $C_2$-$C_4$-alkyl, or is a group *—[Z—O]$_n$—CH=CH$_2$, wherein the asterisk denotes the point of attachment to the oxygen atom, Z is $C_2$-$C_4$-alkylene and n is 0, 1, 2, 3, 4 or 5,
   in the presence of one or more than one catalyst,
   to yield a compound of the general formula (I), wherein X represents the group $X_1$,
   and optionally one or two of the following steps:
   (iii) subjecting the compound obtained in step (ii) to a reduction reaction of the carbonyl group to a hydroxyl group, to obtain a compound of the general formula (I), wherein X represents a group $X_2$ where $R^1$ is hydrogen,
   (iv.a) subjecting the compound obtained in step (iii) to an etherification reaction to obtain a compound of the general formula (I), wherein X represents a group $X_2$ where $R^1$ is methyl or ethyl,
   or
   (iv.b) subjecting the compound obtained in step (iii) to an esterification reaction to obtain a compound of the general formula (I), wherein X represents a group $X_3$,
   or
   (iv.c) reacting the compound obtained in step (iii) with a carbonate $(R^3$—O)$_2$—(C=O), where $R^3$ is selected from hydrogen methyl, ethyl and phenyl, where at least one of $R^3$ is different from hydrogen, in the presence of a catalyst; or with a reagent $R_3$—O—C=O—$Y^1$, wherein $R^3$ is selected from hydrogen, methyl, ethyl and phenyl and $Y^1$ represents a leaving group, selected from —O-(tert.-butoxycarbonyl) and Cl, in the presence of a catalyst or a base,
   to obtain a compound of the general formula (I), wherein X represents a group $X_4$.

7. The process according to claim 6, where
   in step (iv.a) the compound obtained in step (iii) is reacted with an alkylation reagent selected from compounds of formula $R^{1a}$—Y, dimethylsulfate and diethylsulfate, in the presence of a base, wherein $R^{1a}$ is methyl or ethyl and Y represents a leaving group selected from halogen, such as Cl, Br or I, and sulfonates, such as tosylate, mesylate, triflate or nonaflate; and
   in step (iv.b) the compound obtained in step (iii) is reacted with a $C_1$-$C_3$-carboxylic acid or an anhydride of a $C_2$-$C_3$-carboxylic acid or a $C_2$-$C_3$-carboxylic acid halide.

8. The process according to claim 6, where 2,5,6-trimethylcyclohex-2-en-1-ol (IV) provided in step (i) is obtained by subjecting 2,5,6-trimethylcyclohex-2-en-1-one (VI)

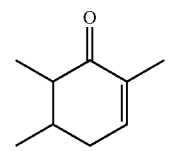

(VI)

to a selective reduction reaction of the carbonyl group to a hydroxyl group.

9. The process according to claim 6, where step (ii) comprises the following steps:
   (ii.a) reacting 2,5,6-trimethylcyclohex-2-en-1-ol (IV) provided in step (i) with a vinylether of the general formula (V)

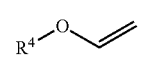

(V)

wherein
   $R^4$ is $C_2$-$C_4$-alkyl, or is a group *—[Z—O]$_n$—CH=CH$_2$, wherein the asterisk denotes the point of attachment to the oxygen atom, Z is $C_2$-$C_4$-alkylene and n is 0, 1, 2, 3, 4 or 5, in the presence of a catalyst,
   (ii.b) further reacting the intermediate compound (II) obtained in step (ii.a) at temperatures of at least 150° C. and/or in the presence of a catalyst,
   (ii.c) further reacting the intermediate compound (III) obtained in step (ii.b) at temperatures of at least 150° C. and/or in the presence of a catalyst,
   to yield a compound of the general formula (I), wherein X represents the group $X_1$.

10. A method comprising utilizing the compound of formula (I), or a stereoisomer thereof or of a mixture of two or more stereoisomers thereof, as defined claim 1, as an aroma chemical.

11. The method according to claim 10, of a compound of the formula (I), of a stereoisomer thereof or of a mixture of two or more stereoisomers thereof; where in compounds (I) X is $X_1$, $X_2$ or $X_3$, $R^4$ is $C_2$-$C_4$-alkyl.

12. A method comprising utilizing the compound of formula (I), or a stereoisomer thereof or of a mixture of two or more stereoisomers thereof, as defined in claim 1, for modifying the scent character of a fragranced composition.

13. A composition comprising
a compound of formula (I), or a stereoisomer thereof or a mixture of two or more stereoisomers thereof, as defined in claim 1, and
at least one further component selected from the group consisting of aroma chemicals, non-aroma chemical carriers, anti-oxidants and deodorant-active agents.

14. The composition according to claim 13, comprising
a compound of the formula (I), or a stereoisomer thereof or a mixture of two or more stereoisomers thereof, where in compounds (I) X is $X_1$, $X_2$ or $X_3$, where in $X_3$ $R^4$ is $C_2$-$C_4$-alkyl; and
at least one further component selected from the group consisting of aroma chemicals, non-aroma chemical carriers, anti-oxidants and deodorant-active agents.

15. The composition according to claim 13, where the non-aroma chemical carriers are selected from the group consisting of surfactants, oil components and solvents, where the solvents are selected from ethanol, isopropanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), and benzyl benzoate.

16. The composition according to claim 13, where the composition is selected from the group consisting of perfume compositions, body care compositions, products for oral and dental hygiene, hygiene articles, cleaning compositions, textile detergent compositions, compositions for scent dispensers, foods, food supplements, pharmaceutical compositions and crop protection compositions.

17. A method of preparing a fragranced composition, comprising incorporating a compound of formula (I), or a stereoisomer thereof or a mixture of two or more stereoisomers thereof, as defined in claim 1, into said composition.

* * * * *